(12) United States Patent
Herr et al.

(10) Patent No.: US 10,597,401 B2
(45) Date of Patent: Mar. 24, 2020

(54) METHODS AND INTERMEDIATES FOR THE PREPARATION OF OMACETAXINE AND CEPHALOTAXINE DERIVATIVES THEREOF

(71) Applicant: ALBANY MOLECULAR RESEARCH, INC., Albany, NY (US)

(72) Inventors: Robert Jason Herr, Voorheesville, NY (US); Brian Thomas Gregg, Altamont, NY (US); William Bert Geiss, Athens, NY (US)

(73) Assignee: Albany Molecular Research, Inc., Albany, NY (US)

(*) Notice: Subject to any disclaimer, the term of this patent is extended or adjusted under 35 U.S.C. 154(b) by 0 days.

(21) Appl. No.: 15/572,372

(22) PCT Filed: May 5, 2016

(86) PCT No.: PCT/US2016/030993
§ 371 (c)(1),
(2) Date: Nov. 7, 2017

(87) PCT Pub. No.: WO2016/182850
PCT Pub. Date: Nov. 17, 2016

(65) Prior Publication Data
US 2018/0134724 A1    May 17, 2018

Related U.S. Application Data

(60) Provisional application No. 62/159,005, filed on May 8, 2015.

(51) Int. Cl.
| | | |
|---|---|---|
| C07D 491/04 | (2006.01) | |
| C07D 491/14 | (2006.01) | |
| C07D 491/147 | (2006.01) | |
| C07D 223/14 | (2006.01) | |
| C07D 317/34 | (2006.01) | |
| C07D 305/12 | (2006.01) | |
| A61P 35/00 | (2006.01) | |
| A61K 31/55 | (2006.01) | |
| C07B 35/02 | (2006.01) | |
| C07B 51/00 | (2006.01) | |
| C07B 63/00 | (2006.01) | |

(52) U.S. Cl.
CPC .......... *C07D 491/147* (2013.01); *A61K 31/55* (2013.01); *A61P 35/00* (2018.01); *C07B 35/02* (2013.01); *C07B 51/00* (2013.01); *C07B 63/00* (2013.01); *C07D 305/12* (2013.01); *C07D 317/34* (2013.01)

(58) Field of Classification Search
CPC ............... C07D 491/04; C07D 491/14; C07D 491/147; C07D 223/14; C07C 223/14
See application file for complete search history.

(56) References Cited

U.S. PATENT DOCUMENTS

| | | |
|---|---|---|
| 6,214,865 B1 | 4/2001 | Littlefield et al. |
| 6,579,869 B1 | 6/2003 | Robin et al. |
| 6,613,900 B2 | 9/2003 | Robin et al. |
| 6,831,180 B1 | 12/2004 | Robin et al. |
| 7,169,774 B2 | 1/2007 | Robin et al. |
| 7,285,546 B2 | 10/2007 | Robin et al. |
| 7,816,476 B2 | 10/2010 | Moszner et al. |
| 7,842,685 B2 | 11/2010 | Cee et al. |
| 7,842,687 B2 | 11/2010 | Robin et al. |
| 8,008,514 B2 | 8/2011 | Ferrari et al. |
| 8,148,554 B2 | 4/2012 | Seletsky et al. |
| 8,466,142 B2 | 6/2013 | Gin et al. |
| RE45,128 E | 9/2014 | Robin et al. |
| 2004/0006064 A1 | 1/2004 | Robin et al. |
| 2012/0022250 A1 | 1/2012 | Robin et al. |
| 2014/0171416 A1 | 6/2014 | Gin et al. |

FOREIGN PATENT DOCUMENTS

| | | |
|---|---|---|
| CN | 102304132 A | 1/2012 |
| JP | 2009-132735 A | 6/2009 |
| WO | 99/48894 A1 | 9/1999 |
| WO | 2009/148654 A2 | 12/2009 |
| WO | 2010/103405 A2 | 9/2010 |

OTHER PUBLICATIONS

International Search Report and Written Opinion for corresponding Application No. PCT/US2016/030993 (dated Aug. 8, 2016).
Seebach et al., "α-Alkylation of α-Heterosubstituted Carboxylic Acids Without Racemization : EPC-Syntheses of Tertiary Alcohols and Thiols," Tetrahedron 40:1313-1324 (1984).
Hoye et al., "Preparation of 5-Alkyl-2-tert-butyl-1,3-dioxolan-4-ones by Trimethylsilyl Triflate Catalyzed Reactions Between Bis(trimethylsilyl) Derivatives of α-Hydroxycarboxylic Acids and Pivaldehyde," J. Org. Chem. 52:1351-1353 (1987).
Trost et al., "Towards the Total Synthesis of Saponaceolides: Synthesis of cis-2,4-Disubstituted 3,3-Dimethylmethylenecyclohexanes," Angew. Chem. Int. Ed 38:3662-3664 (1999).
Gockel et al., "Enantioselective Synthesis of the Predominant AB Ring System of the Schisandra Nortriterpenoid Natural Products," Org. Lett. 16:4480-4483 (2014).
Mukheijee et al., "Gold(I)-Catalyzed Enantioselective Intramolecular Dehydrative Amination of Allylic Alcohols with Carbamates," Angew. Chem. Int. Ed 51:1405-1407 (2012).
International Preliminary Report on Patentability for corresponding Application No. PCT/US2016/030993 (dated Nov. 14, 2017).
Chang et al., "Chapter 10—Chemistry, Bioactivity, and the Structure-Activity Relationship of Cephalotaxine—Type Alkaloids from *Cephalotaxus* sp." Studies in Natural Products Chemistry, 53:339-373 (2017).

*Primary Examiner* — Bruck Kifle
(74) *Attorney, Agent, or Firm* — Pepper Hamilton LLP

(57) ABSTRACT

The present invention relates to methods and intermediates for the preparation of omacetaxine and cephalotaxine derivatives thereof. The resulting products are useful in the treatment of proliferative diseases and infectious diseases.

22 Claims, 1 Drawing Sheet

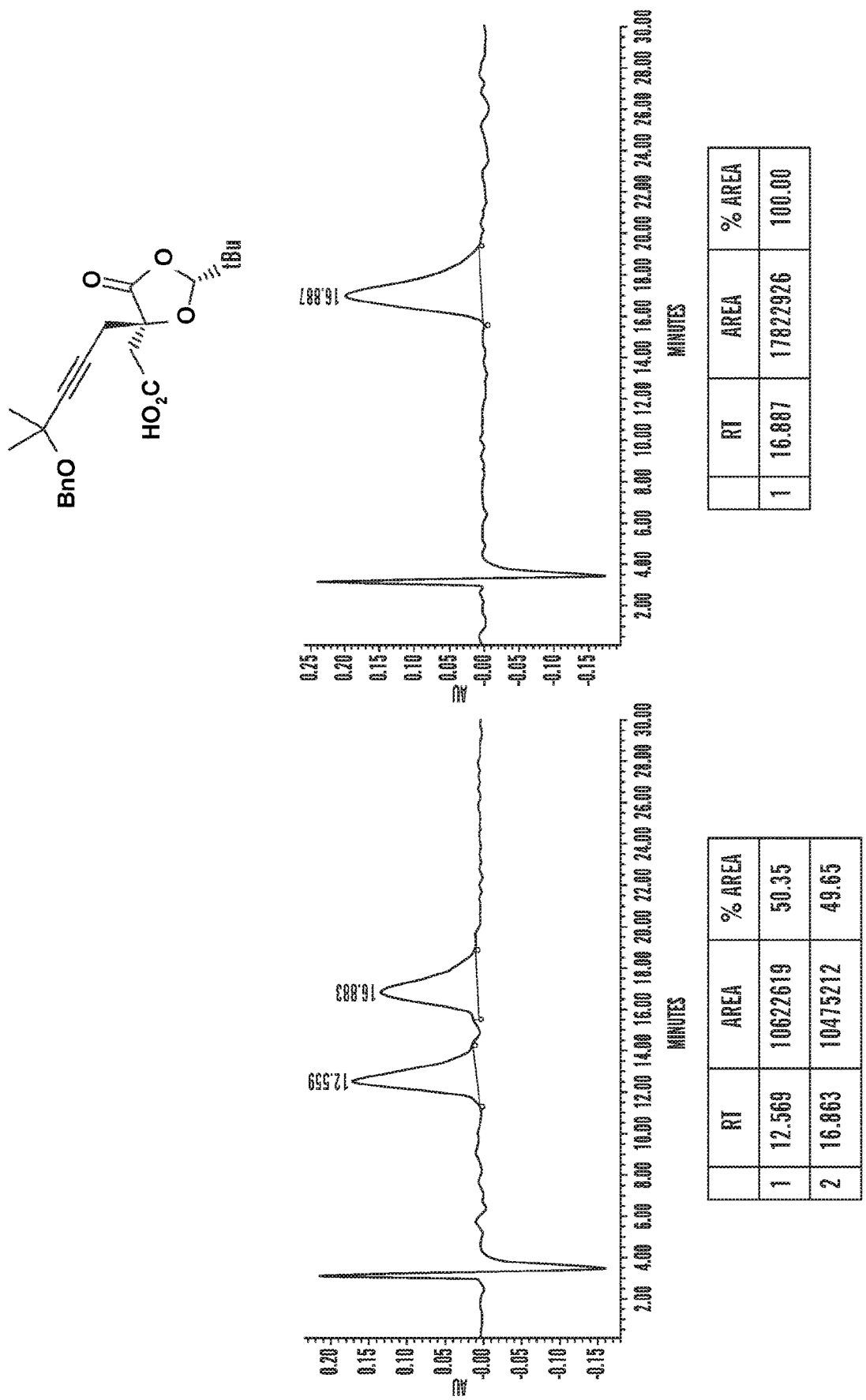

METHODS AND INTERMEDIATES FOR THE PREPARATION OF OMACETAXINE AND CEPHALOTAXINE DERIVATIVES THEREOF

This application is a national stage application under 35 U.S.C. § 371 of International Application No. PCT/US2016/030993, filed May 5, 2016, which claims the priority benefit of U.S. Provisional Patent Application Ser. No. 62/159,005, filed May 8, 2015, which are hereby incorporated by reference in their entirety.

FIELD OF THE INVENTION

The present invention relates to methods and intermediates for the preparation of omacetaxine and cephalotaxine derivatives thereof. The resulting products are useful in the treatment of proliferative diseases and infectious diseases.

BACKGROUND OF THE INVENTION

Omacetaxine mepesuccinate (SYNRIBO™) is used to treat adults with chronic or accelerated phase chronic myeloid leukemia (CML) who are no longer responding to, or who could not tolerate, two or more tyrosine kinase inhibitors. Omacetaxine mepesuccinate is a cephalotaxine ester and is a protein synthesis inhibitor. Omacetaxine mepesuccinate is typically prepared by a semi-synthetic process from cephalotaxine, an extract from the leaves of *Cephalotaxus* sp. While cephalotaxine accounts for approximately 50% of the mass of the crude alkaloid extract mixture from powdered leaves and stems of *Cephalotaxus* sp., several minor constituents have also been identified. Among these are several rare C3-ester derivatives. The ester derivatives show cytotoxic properties, but cephalotaxine itself has been found to be biologically inactive. However, the naturally occurring ester derivatives are typically attainable in only <0.1% of the plant dry weight. Certain cephalotaxus ester derivatives, namely omacetaxine mepesuccinate, are available through semisynthetic methods. The synthesis of omacetaxine mepesuccinate [aka (−)-homoharringtonine] has been achieved by semi-synthetic methods from the combination of cephalotaxine with various activated malic acid-derived precursors that make up the mepesucinate portion.

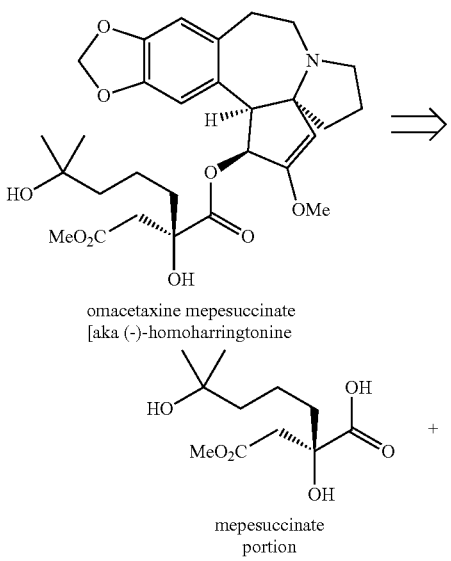

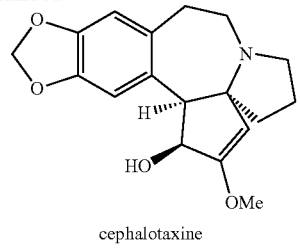
cephalotaxine

Cephalotaxine is commercially available and easily sourced, and has been the target of numerous total synthesis publications. As a result, the majority of publications and patents centers around ways to prepare the enantiopure mepesuccinate portion. Although the synthesis of both racemic and enantiopure side chain precursors have been reported as far back as the 1980s (for instance Hudlicky et al., *Tetrahedron Lett.*, 23: 3431 (1982)), the research groups of Gin and Tietze have fashioned enantiopure side chain precursors from cyclic malic acid templates as shown below:

In the case of both groups, (2R)-malic acid (A) was cyclized to the dioxolanone scaffold B, which was treated with two equivalents of base at low temperature. The resulting dianion was treated with various allylic halides to produce the C-alkylated adducts C, which were then converted to a-alkylated malic acid monoesters D. This work with allylic halides is in itself not new, as the Self-Regeneration of Stereocenters (SRS) concept was demonstrated with this same scaffold B by Seebach and coworkers in the early 1980s (Seebach et al., *Helv. Chim. Acta*, 64: 2704 (1981); see also Seebach et al., *Angew. Chem. Int. Ed.*, 35:2708 (1996)).

The Tietze group has used this chemistry to prepare homoharringtonine analogs, but not omacetaxine mepesuccinate in particular (Tietze et al., *Eur. J. Org. Chem.*, 2965 (2005)). The Gin group has reported this chemistry for the preparation of homoharringtonine analogs (Gin et al., *J. Am. Chem. Soc.*, 128:10370 (2006)) and specifically to prepare the side chain of omacetaxine mepesuccinate (Gin et al., *Chem. Eur. J.*, 14:4293 (2008); U.S. Pat. No. 8,466,142). The synthetic sequence for the process as it appears in the 2008 publication and '142 Patent is as shown below:

3   4
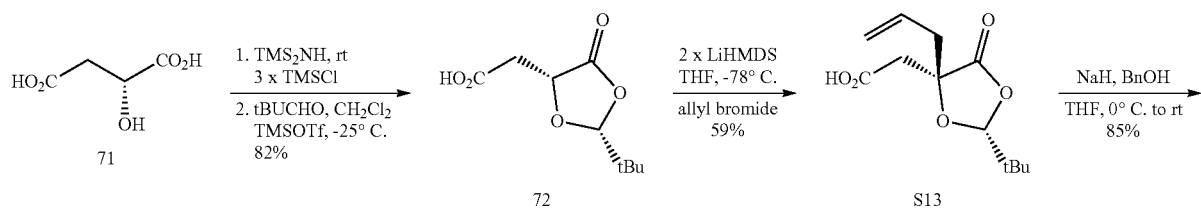
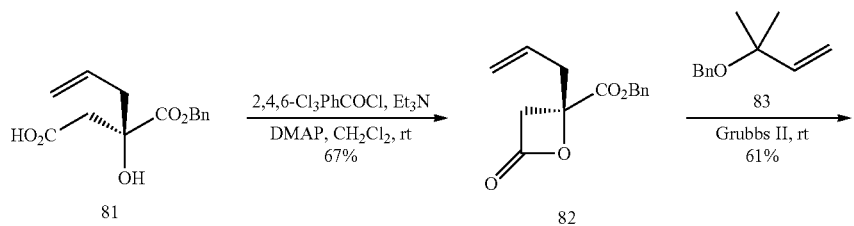
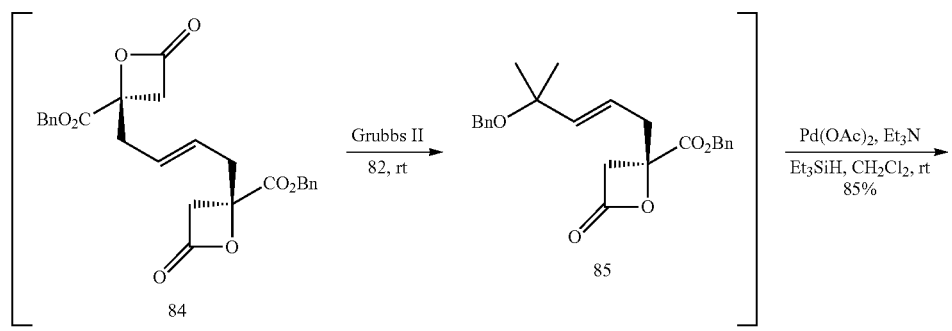
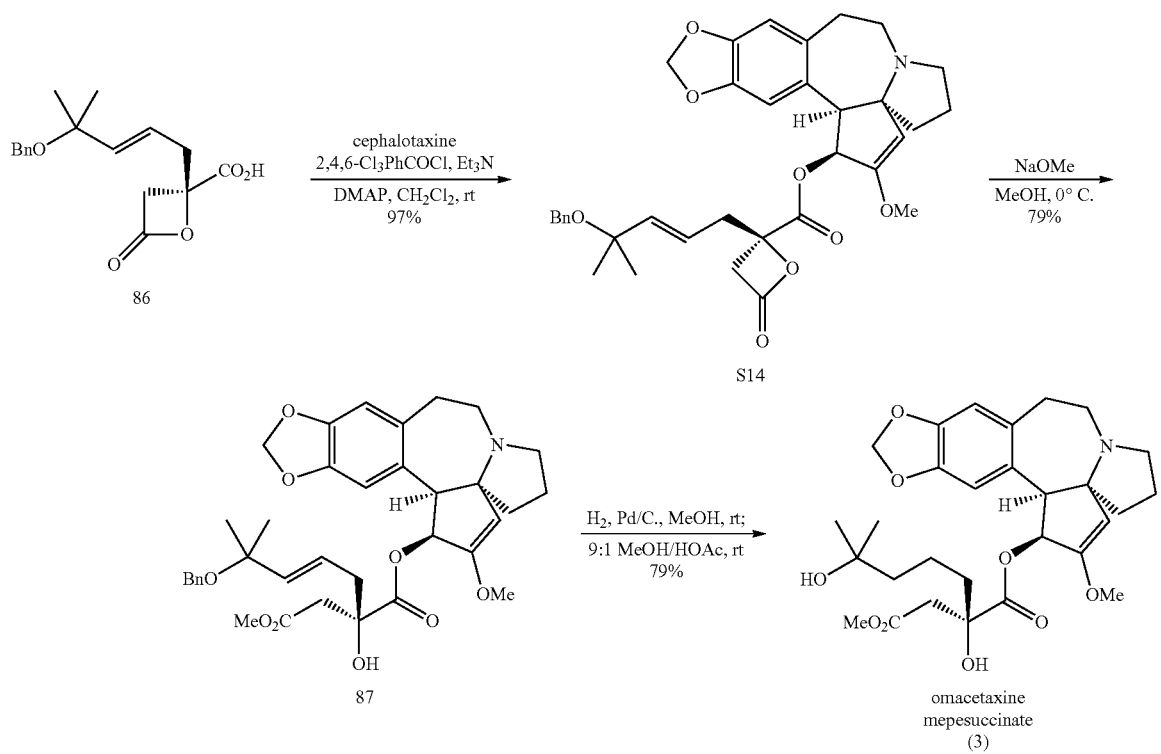

However, such approaches are not efficient and typically require careful chromatography steps to obtain the desired isomer for treatment. Moreover, such approaches are not able to produce other bioactive members of the family.

The present invention is directed to overcoming these and other deficiencies in the art.

SUMMARY OF THE INVENTION

The present invention relates to a process for preparation of a product compound of formula I:

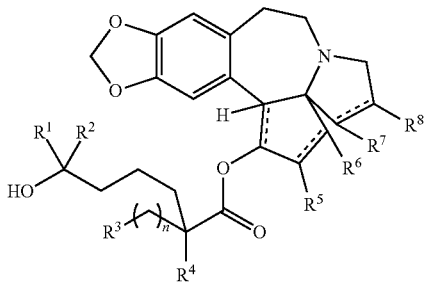

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with substituents as defined below in $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^1$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^1$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —$CN$, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

each ═ independently designates a single or double bond; and n is an integer from 0 to 9;

m is an integer from 0 to 2, or a pharmaceutically acceptable salt thereof, or a solvate thereof, said process comprising:

providing an intermediate compound II having the structure:

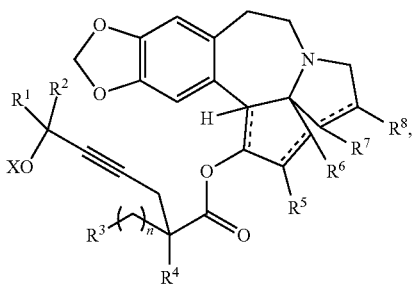

(II)

wherein X is hydrogen or a protecting group, and forming the product compound of formula I from intermediate compound II.

The present invention also relates to a process for preparation of a product compound of formula XIV:

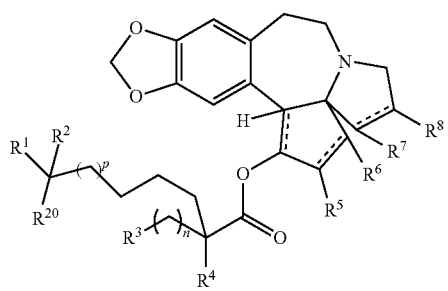

(XIV)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with substituents as defined below in $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

each ⁓ independently designates a single or double bond; and n is an integer from 0 to 9;
m is an integer from 0 to 2;
p is an integer from 0 to 3,
or a pharmaceutically acceptable salt thereof, or a solvate thereof,
said process comprising providing intermediate compound XVa having the structure:

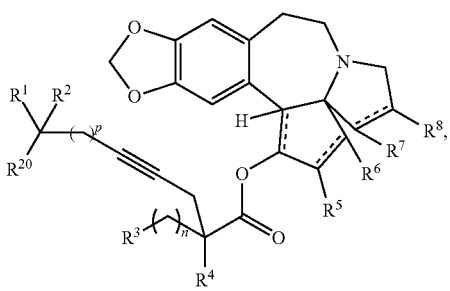

and
forming the product compound of formula XIV from intermediate compound XVa.

The present invention further relates to a process for preparation of a product compound of formula IX:

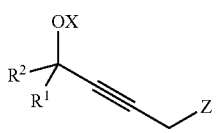

wherein
X is hydrogen or a protecting group;
Z is selected from the group consisting of halogen, —OSO$_2$R$^{19}$, —OSO$_3$R$^{19}$, —OCOR$^{19}$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, and —N(R$^{19}$)$_3^+$;
R$^1$ and R$^2$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or
R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or
R$^1$ and R$^2$ are taken together with the atom to which they are attached to form a carbonyl, thiocarbonyl, sulfoxide, or sulfone;
R$^{11}$ is independently selected at each occurrence from a substituent in the group consisting of halogen, —NO$_2$, —OR, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, wherein each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted with 1 to 3 substituents independently selected at each occurrence from the group consisting of C$_1$-C$_4$ alkyl, C$_1$-C$_4$ alkoxy, halogen, Ar, —CN, and —NR$^{12}$R$^{13}$;

R$^{12}$ and R$^{13}$ are each independently hydrogen, C$_1$-C$_4$ alkyl, C$_1$-C$_4$ haloalkyl, C$_1$-C$_4$ alkoxyalkyl, C$_3$-C$_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, C$_1$-C$_4$ alkyl, C$_1$-C$_4$ haloalkyl, and C$_1$-C$_4$ alkoxy; or
R$^{12}$ and R$^{13}$ are taken together with the nitrogen to which they are attached to form a piperidine, pyrrolidine, piperazine, N-methylpiperazine, morpholine, or thiomorpholine ring;
R$^{14}$ is C$_1$-C$_4$ alkyl, C$_1$-C$_4$ haloalkyl, or phenyl;
R$^{19}$ is selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; and
m is an integer from 0 to 2,
or a pharmaceutically acceptable salt thereof, or a solvate thereof;
said method comprising providing intermediate compound X having the formula:

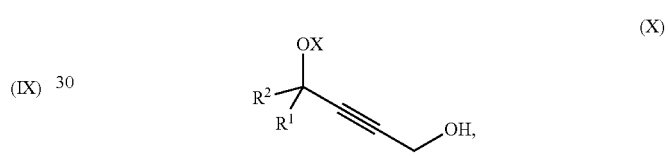

and
forming the product compound of formula IX from intermediate compound X.

Another embodiment of the present invention relates to a process for preparation of a product compound of formula XXIa:

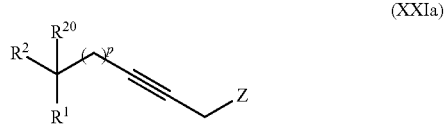

wherein
Z is selected from the group consisting of halogen, —OSO$_2$R$^{19}$, —OSO$_3$R$^{19}$, —OCOR$^{19}$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, and —N(R$^{19}$)$_3^+$;
R$^1$ and R$^2$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or
R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or
R$^1$ and R$^2$ are taken together with the atom to which they are attached to form a carbonyl, thiocarbonyl, sulfoxide, or sulfone;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{20}$ is hydrogen, halogen, —$NO_2$, —$OR^{12}$, —OX, —$NR^{12}R^{13}$, —$NR^{12}C(O)_2R^{13}$, —$NR^2C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

p is an integer from 0 to 3; and m is an integer from 0 to 2, or a pharmaceutically acceptable salt thereof, or a solvate thereof;

said method comprising:

providing intermediate compound XXIVa having the formula:

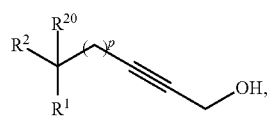

(XXIVa)

and forming the product compound of formula XXIa from intermediate compound XXIVa.

Yet another embodiment of the present invention relates to intermediates used in the above-described processes of the present invention, including a compound of formula II:

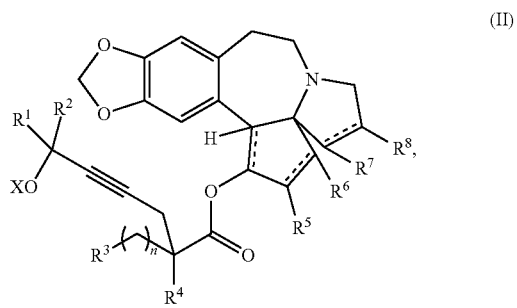

(II)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$ or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

X is hydrogen or a protecting group;

each ---- independently designates a single or double bond; and n is an integer from 0 to 9;

m is an integer from 0 to 2, or a pharmaceutically acceptable salt thereof, or a solvate thereof.

Another aspect of the present invention relates to a compound of formula IIIa:

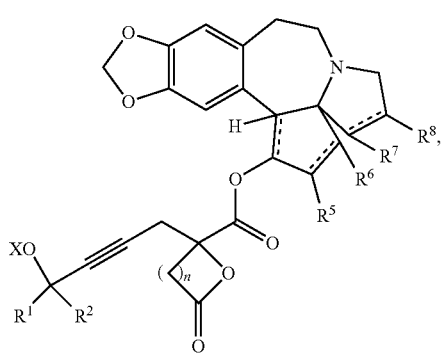

(IIIa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

X is hydrogen or a protecting group;

n is an integer from 0 to 9;

m is an integer from 0 to 2; and each ---- independently designates a single or double bond, or a pharmaceutically acceptable salt thereof, or a solvate thereof.

Yet another aspect of the present invention relates to a compound of formula IVa:

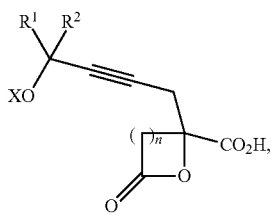

(IVa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

n is an integer from 0 to 9;

m is an integer from 0 to 2; and

X is hydrogen or a protecting group, or a pharmaceutically acceptable salt thereof, or a solvate thereof.

The present invention relates to a compound of formula Va:

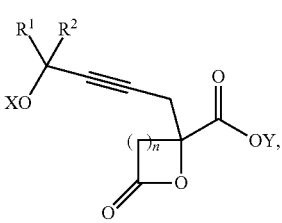

(Va)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

n is an integer from 0 to 9;

m is an integer from 0 to 2; and

X and Y are each independently hydrogen or a protecting group, or a pharmaceutically acceptable salt thereof, or a solvate thereof.

Another aspect of the present invention relates to a compound of formula VIa:

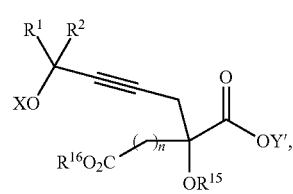

(VIa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

n is an integer from 0 to 9;

m is an integer from 0 to 2; and

X and Y' are each independently hydrogen or a protecting group, or a pharmaceutically acceptable salt thereof, or a solvate thereof.

The present invention relates to a compound of formula VIIa:

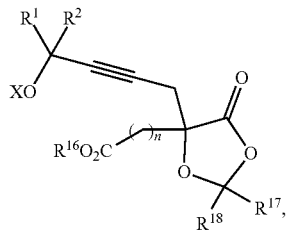

(VIIa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{16}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{17}$ is t-Bu, phenyl, naphthyl, $CF_3$, $CCl_3$, $CBr_3$, or $C_1$-$C_6$ alkoxy;

$R^{18}$ is H, Me, $CF_3$, $CCl_3$, $CBr_3$, or $C_1$-$C_6$ alkoxy; or $R^{17}$ and $R^{18}$ combine with the carbon to which they are attached to form an internally bridged cycloalkyl, wherein internally bridged cycloalkyl can be optionally substituted from 1 to 6 times with a substituent independently selected in each occurrence from $C_{1-6}$ alkyl and $C_{1-6}$ alkyl further substituted with —$SO_2N(C_{1-6}$ alkyl$)_2$; or $R^{17}$ and $R^{18}$ are taken together to form a carbonyl, thiocarbonyl, sulfoxide, or sulfone;

n is an integer from 0 to 9;

m is an integer from 0 to 2; and

X is hydrogen or a protecting group, or a pharmaceutically acceptable salt thereof, or a solvate thereof.

The present invention also relates to a compound of formula XVa:

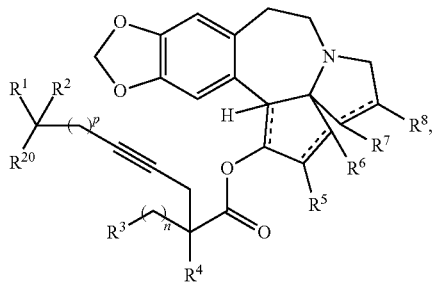

(XVa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —$CN$, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

each ═ independently designates a single or double bond;

n is an integer from 0 to 9;

p is an integer from 0 to 3; and m is an integer from 0 to 2, or a pharmaceutically acceptable salt thereof, or a solvate thereof.

Another embodiment of the present invention relates to a compound of formula XVIa:

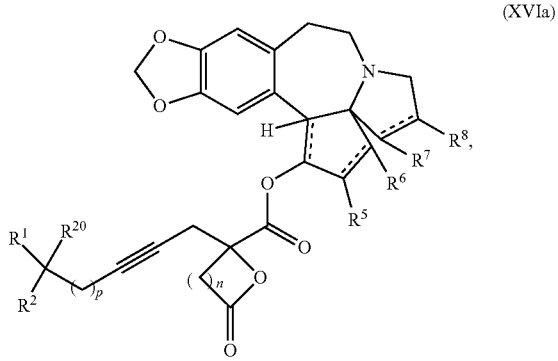

(XVIa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^5$ is hydrogen, —$OR^{10}$, or ═O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

n is an integer from 0 to 9;

m is an integer from 0 to 2;

p is an integer from 0 to 3; and each ═ independently designates a single or double bond, or a pharmaceutically acceptable salt thereof, or a solvate thereof.

A further aspect of the present invention relates to a compound of formula XVIIa:

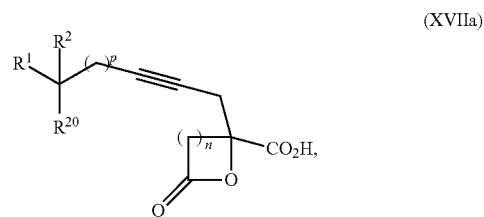

(XVIIa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, $-NO_2$, $-OR$, $-N^{12}R^{13}$, $-NR^{12}C(O)_2R^{13}$, $-NR^{12}C(O)N^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring; and $R^{14}$ is $C_1$-$C_4$ alkyl, $C_1$-$C_4$ haloalkyl, or phenyl;

$R^{20}$ is hydrogen, halogen, $-NO_2$, $-OR^{12}$, $-OX$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^3$, $-C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;
n is an integer from 0 to 9;
m is an integer from 0 to 2; and
p is an integer from 0 to 3;

or a pharmaceutically acceptable salt thereof, or a solvate thereof.

The present invention also relates to a compound of formula XVIIIa:

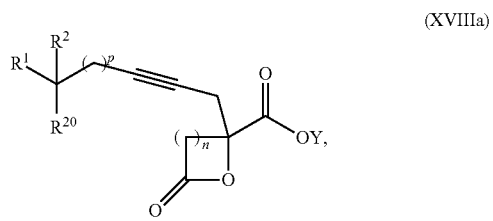

(XVIIIa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, $-NO_2$, $-OR$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, $-NO_2$, $-OR^{12}$, $-OX$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;
n is an integer from 0 to 9;
m is an integer from 0 to 2;
p is an integer from 0 to 3; and
Y is hydrogen or a protecting group, or a pharmaceutically acceptable salt thereof, or a solvate thereof.

The present invention also relates to a compound of formula XIXa:

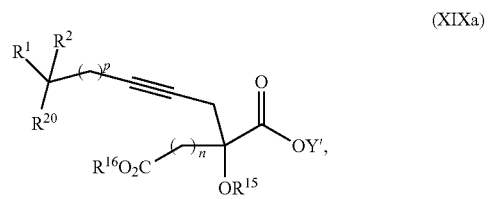

(XIXa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^3$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

n is an integer from 0 to 9;

m is an integer from 0 to 2;

p is an integer from 0 to 3; and

Y' is hydrogen or a protecting group, or a pharmaceutically acceptable salt thereof, or a solvate thereof.

Another aspect of the present invention relates to a compound of formula XXa:

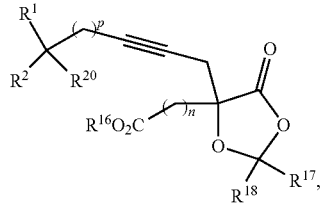

(XXa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{16}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{17}$ is t-Bu, phenyl, naphthyl, $CF_3$, $CCl_3$, $CBr_3$, or $C_1$-$C_6$ alkoxy;

$R^{18}$ is H, Me, $CF_3$, $CCl_3$, $CBr_3$, or $C_1$-$C_6$ alkoxy; or $R^{17}$ and $R^{18}$ combine with the carbon to which they are attached to form an internally bridged cycloalkyl, wherein the internally bridged cycloalkyl can be optionally substituted from 1 to 6 times with a substituent independently selected in each occurrence from $C_{1-6}$ alkyl and $C_{1-6}$ alkyl further substituted with —$SO_2N(C_{1-6}$ alkyl$)_2$; or $R^{17}$ and $R^{18}$ are taken together with the atom to which they are attached to form a carbonyl, thiocarbonyl, sulfoxide, or sulfone;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

n is an integer from 0 to 9;

m is an integer from 0 to 2; and p is an integer from 0 to 3, or a pharmaceutically acceptable salt thereof, or a solvate thereof.

The present invention relates to a compound of formula IX:

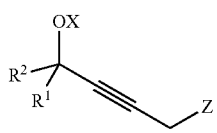

(IX)

wherein

X is hydrogen or a protecting group;

Z is selected from the group consisting of halogen, —$OSO_2R^{19}$, —$OSO_3R^{19}$, —$OCOR^{19}$, —$OCO_2R^{19}$, —$OCSR^{19}$, —$OCS_2R^{19}$, —$OCN(R^{19})_2$, —$OPO(R^{19})_2$, —$OPO(OR^{19})_2$, —$N(R^{19})_3{}^+$;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl; $R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; and m is an integer from 0 to 2, or a pharmaceutically acceptable salt thereof, or a solvate thereof.

The present invention relates to a compound of formula XIII:

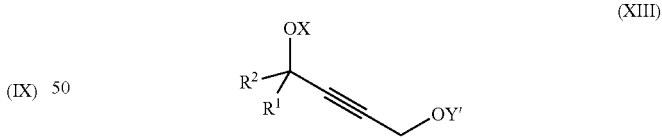

(XIII)

wherein

X is hydrogen or a protecting group;

Y' is hydrogen or a protecting group;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl; and m is an integer from 0 to 2, or a pharmaceutically acceptable salt thereof, or a solvate thereof.

The present invention also relates to a compound of formula XXIa:

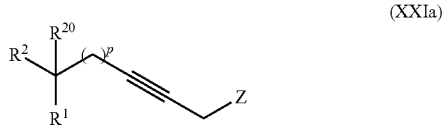

(XXIa)

wherein

Z is selected from the group consisting of halogen, —$OSO_2R^{19}$, —$OSO_3R^{19}$, —$OCOR^{19}$, —$OCO_2R^{19}$, —$OCSR^{19}$, —$OCS_2R^{19}$, —$OCN(R^{19})_2$, —$OPO(R^{19})_2$, —$OPO(OR^{19})_2$, —$N(R^{19})_3^+$;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^3$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

p is an integer from 0 to 3; and m is an integer from 0 to 2, or a pharmaceutically acceptable salt thereof, or a solvate thereof.

Another compound of the present invention comprises intermediate compound XXVIa having the formula:

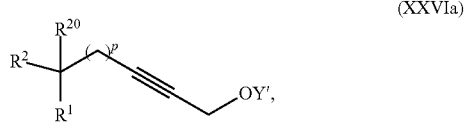

(XXVIa)

wherein

Y' is hydrogen or a protecting group;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring; and $R^{14}$ is $C_1$-$C_4$ alkyl, $C_1$-$C_4$ haloalkyl, or phenyl;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

p is an integer from 0 to 3; and m is an integer from 0 to 2, or a pharmaceutically acceptable salt thereof, or a solvate thereof.

In accordance with the present technology, highly purified and crystalline forms of omacetaxine and derivatives thereof are produced, without the need for careful chromatography and/or inefficient recycling steps. In the methods of the present invention, a streamlined and versatile approach allows for the synthesis of a single desired diastereomer in substantially pure form which can be used in pharmaceutical compositions, especially for the treatment of cancer and other proliferative diseases. In particular, the methods of the present invention are more direct and amenable to large scale synthesis. Crystallization of key intermediates in the processes of the present invention obviates the need for chromatography or other resolution requirements, as in the prior art. In addition, the methods of the present invention allow for the chemical synthesis of omacetaxine derivatives, and will enable cytotoxic profile evaluation of such derivatives in order to find improved treatments for CML and other proliferative diseases.

There are no known examples in the prior art in which the SRS C-alkylation reaction of the dioxolanone scaffold has been performed with a propargyl halide or like activated precursor, as in the present invention. In particular, in the present application (see, e.g., Schemes 1-2), C-alkylation of the dianion of enantiopure dioxolanone VIIIa (specific compound 8 known to literature, compound 72 in U.S. Pat. No. 8,466,142) is performed with alkyne compounds IX/XXIa, activated at the propargyl position to produce C-propargyl compounds VIIa/XXa. As stated above, transformations of this type are not known to the literature. This method is superior to the process in U.S. Pat. No. 8,466,142, in that the protected oxygen and gem-dimethyl functionality required for omacetaxine mepesuccinate is already incorporated in the processes of the present invention, whereas the functional groups must be added at a later stage in a less efficient manner in U.S. Pat. No. 8,466,142. Moreover, the transformation of VIIa/XXa to Va/XVIIIa (diololanone ring-opening and activation of the primary carboxylic acid and lactone formation) described in the present application makes use of a protecting group not described in U.S. Pat. No. 8,466,142 and includes the alkyne-containing functionality that is not disclosed in the prior art. Further, unmasking of the acid in Va/XVIIIa to produce coupling precursor IVa/XVIIa is different than U.S. Pat. No. 8,466,142 in the use of deprotection chemistry not described there. The methods of the present invention differ in general from those disclosed in U.S. Pat. No. 8,466,142 by virtue of the alkyne functionality, instead of the (E)-alkene that is present in U.S. Pat. No. 8,466,142.

BRIEF DESCRIPTION OF THE DRAWINGS

FIG. 1 shows the chiral HPLC analysis of Compound VI of the present invention. The reference sample is on the left and is an analysis of a racemic version of Compound VI. The sample on the right is of recrystallized Compound VII produced in accordance with the present invention and shows diastereomeric purity. Chiral HPLC analysis of recrystallized Compound VII reveals complete enantiomeric excess (>99% ee).

DETAILED DESCRIPTION OF THE INVENTION

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, 3-pentyl, and the like.

The term "alkenyl" means an aliphatic hydrocarbon group containing a carbon-carbon double bond and which may be straight or branched having about 2 to about 6 carbon atoms in the chain. Particular alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. The term "alkenyl" may also refer to a hydrocarbon chain having 2 to 6 carbons containing at least one double bond and at least one triple bond.

The term "alkynyl" means an aliphatic hydrocarbon group containing a carbon-carbon triple bond and which may be straight or branched having about 2 to about 6 carbon atoms in the chain. Particular alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

The term "cycloalkyl" means a non-aromatic, saturated or unsaturated, mono- or multi-cyclic ring system of about 3 to about 7 carbon atoms, or of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "cycloalkylalkyl" means a cycloalkyl-alkyl-group in which the cycloalkyl and alkyl are as defined herein. Exemplary cycloalkylalkyl groups include cyclopropylmethyl and cyclopentylmethyl. The alkyl radical and the cycloalkyl radical may be optionally substituted as defined herein.

As used herein, "heterocyclyl" or "heterocycle" refers to a stable 3- to 18-membered ring (radical) which consists of carbon atoms and from one to five heteroatoms selected from the group consisting of nitrogen, oxygen, and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "aryl" or "Ar" means an aromatic monocyclic or multi-cyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "heteroaryl" means an aromatic monocyclic or multi-cyclic ring system of about 5 to about 19 ring atoms, or about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Particular heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

The terms "arylalkyl" and "heteroarylalkyl" mean an alkyl substituted with one or more aryl or heteroaryl groups, wherein the alkyl, aryl, and heteroaryl groups are as herein described. One particular example is an arylmethyl or heteroarylmethyl group, in which a single carbon spacer unit is attached to an aryl or heteroaryl group, where the carbon spacer and the aryl or heteroaryl group can be optionally substituted as described herein.

As used herein, the term "acyl" means a moiety of formula R-carbonyl, where R is an alkyl, cycloalkyl, aryl, or heteroaryl as defined above. Exemplary acyl groups include formyl, acetyl, propanoyl, benzoyl, and propenoyl.

The term "carbonyl" means a carbonyl group, —C(O)—.

The term "thiocarbonyl" means a thiocarbonyl group, —C(S)—.

The term "sulfoxide" means a sulfoxide group, —S(O)—.

The term "sulfone" means a sulfone group, —S(O)$_2$—.

The term "alkoxy" means groups of from 1 to 8 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example,

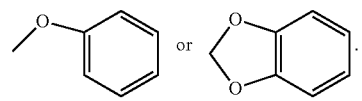

The term "halogen" means fluoro, chloro, bromo, or iodo.
The term "phenyl" means a phenyl group as shown below

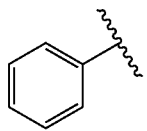

The term "benzyl" means a benzyl group as shown below

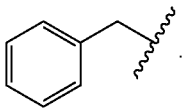 [SMILES: *Cc1ccccc1]

The term "naphthyl" means a naphthyl group as shown below

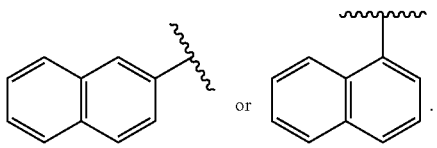 [SMILES: *c1ccc2ccccc2c1 ; *c1cccc2ccccc12]

The term "haloalkyl" means both branched and straight-chain alkyl substituted with one or more halogen, wherein the alkyl group is as herein described.

The term "alkoxyalkyl" means both branched and straight-chain alkyl substituted with one or more alkoxy groups, wherein the alkyl group is as herein described.

The term "cephalotaxine or a derivative thereof" or "cephalotaxine derivative" means the cephalotaxine compound

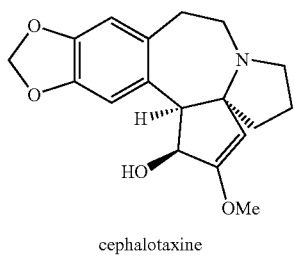 [SMILES: COC1=C[C@]23CCCN2CCc2cc4c(cc2[C@@H]3[C@@H]1O)OCO4]

cephalotaxine and any modifications or substitutions to the structure of cephalotaxine as shown in the compounds described herein.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "compound," "product compound," and equivalent expressions, are meant to embrace compounds of formulae (I)-(XXVI) as described herein. Also contemplated are the prodrugs, the pharmaceutically acceptable salts, the oxides, the solvates, e.g. hydrates, and inclusion complexes of that compound, where the context so permits, as well as any stereoisomeric form, or a mixture of any such forms of that compound in any ratio. Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. In accordance with some embodiments, a compound as described herein, including in the contexts of pharmaceutical compositions, methods of treatment, and compounds per se, is provided as the salt form. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutical composition" means a composition comprising a compound of formula (I) or (XIV) and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compounds described herein, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "pharmaceutically acceptable salt" refers to salts prepared from pharmaceutically acceptable non-toxic acids or bases including inorganic acids and bases and organic acids and bases. Suitable pharmaceutically acceptable acid addition salts for the compounds described herein include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds described herein include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine. Pharmaceutically acceptable salts include, but are not limited to, amine salts, such as but not limited to N, N'dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris (hydroxymethyl) aminomethane; alkali metal salts, such as but not limited to lithium, potassium, and sodium; alkali earth metal salts, such as but not limited to barium, calcium, and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, and fumarates. Pharmaceutically acceptable esters include, but are not limited to, alkyl, alkenyl, alkynyl, aryl, heteroaryl, cycloalkyl, and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C=C (OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C (OC(O) R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

The term "solvate" refers to a compound described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amount" is meant to describe an amount of compound described herein effective in producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl, and butyl chloride, bromides and iodides; dialkyl sulfates including dimethyl, diethyl, dibutyl, and diamyl sulfates; long chain halides such as decyl, lauryl, myristyl, and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

The present invention relates to a process for preparation of a product compound of formula I:

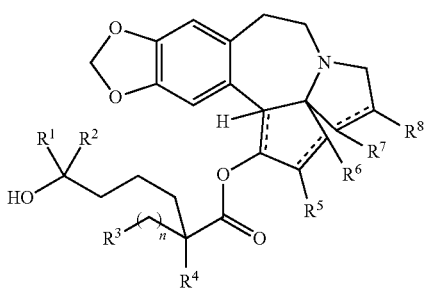

(I)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with substituents as defined below in $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$ or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —$CN$, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —$CN$, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —$CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

each ⚌ independently designates a single or double bond; and n is an integer from 0 to 9;

m is an integer from 0 to 2, or a pharmaceutically acceptable salt thereof, or a solvate thereof, said process comprising:

providing intermediate compound II having the structure:

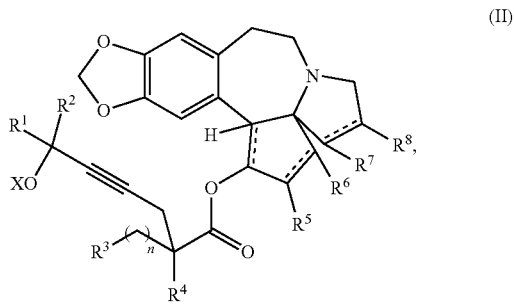

(II)

wherein X is hydrogen or a protecting group, and forming the product compound of formula I from intermediate compound II.

The present invention also relates to a process for preparation of a product compound of formula XIV:

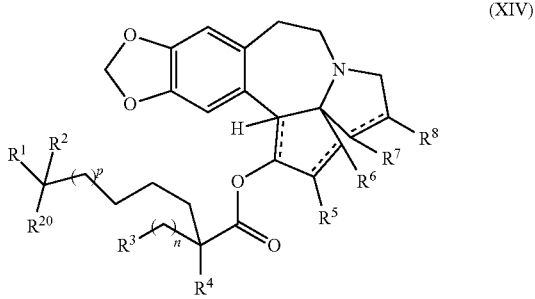

(XIV)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with substituents as defined below in $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

each ⚌ independently designates a single or double bond; and n is an integer from 0 to 9;

m is an integer from 0 to 2;

p is an integer from 0 to 3, or a pharmaceutically acceptable salt thereof, or a solvate thereof, said process comprising providing intermediate compound XVa having the structure:

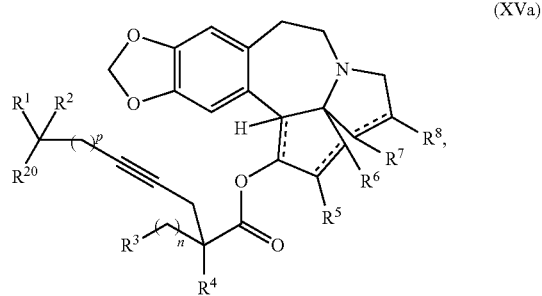

(XVa)

forming the product compound of formula XIV from intermediate compound XVa.

In one embodiment, compound XVa has the following structure:

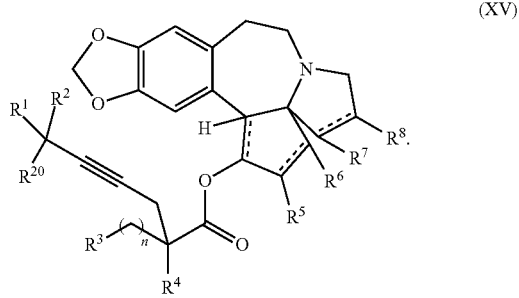

(XV)

In another embodiment, the compound of formula XIV has the following structure:

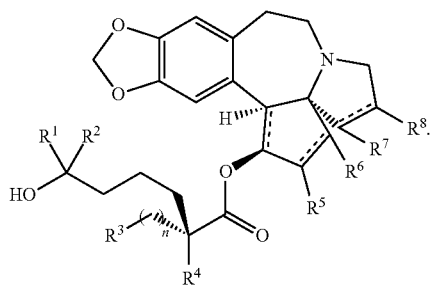

In a further embodiment, the compound of formula XIV has the following structure:

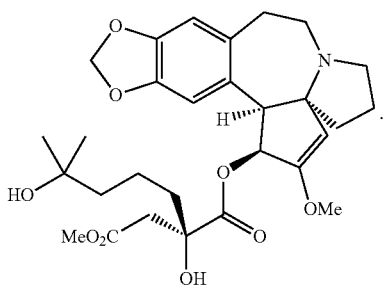

In accordance with any of the embodiments described herein, X can be an arylmethyl or heteroarylmethyl protecting group, optionally substituted from 1 to 3 times with $C_1$-$C_6$ alkyl.

In one particular embodiment, X is selected from the group consisting of alkanoyl, aryloyl, benzyloxycarbonyl, allyloxycarbonyl, (β-trimethylsilylethoxy)carbonyl, (dialkylamino)carbonyl, triphenylmethyl, benzyl, 1-ethoxyethyl, methoxymethyl, 4-methoxyphenylmethyl, methoxyethoxymethyl, benzyloxymethyl, (β-trimethylsilylethoxy)methyl, tetrahydropyranyl, 2,2,2-trichloroethoxycarbonyl, t-butyl(diphenyl)silyl, trialkylsilyl, trichloromethoxycarbonyl, 2,2,2-trichloroethoxymethyl, alkansulfonyl, arylsulfonyl, and aryloxysulfonyl.

Forming the product compound may comprise reacting intermediate compound IIIXV/XVa with a reducing agent under conditions effective to produce the product compound of formula I/XIV.

Where X is present and a protecting group, forming the product compound may comprise reacting intermediate compound II/XV/XVa with a reducing agent followed by removal of the protecting group.

In another embodiment, intermediate compound XV is provided as a substantially pure diastereomer having the structure:

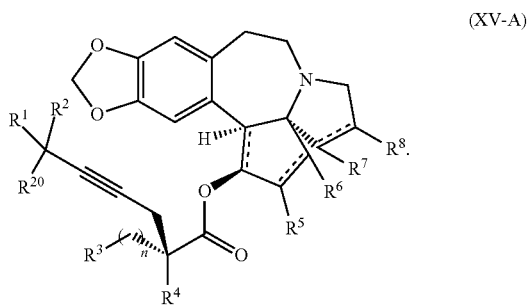

(XV-A)

In yet another embodiment, the process further comprises providing intermediate compound XXa having the structure:

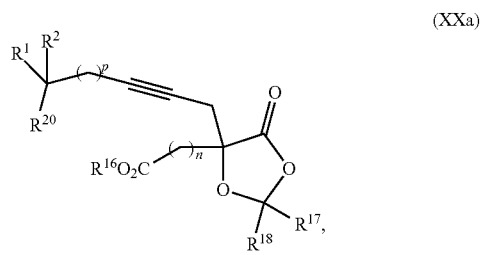

(XXa)

wherein $R^{16}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{17}$ is t-Bu, phenyl, naphthyl, $CF_3$, $CCl_3$, $CBr_3$, or $C_1$-$C_6$ alkoxy;

$R^{18}$ is H, Me, $CF_3$, $CCl_3$, $CBr_3$, or $C_1$-$C_6$ alkoxy; or $R^{17}$ and $R^{18}$ combine with the carbon to which they are attached to form an internally bridged cycloalkyl, wherein the internally bridged cycloalkyl can be optionally substituted from 1 to 6 times with a substituent independently selected in each occurrence from $C_{1-6}$ alkyl and $C_{1-6}$ alkyl further substituted with —$SO_2N(C_{1-6}$ alkyl$)_2$; or $R^{17}$ and $R^{18}$ are taken together with the atom to which they are attached to form a carbonyl, thiocarbonyl, sulfoxide, or sulfone, and forming intermediate compound XVa/XV from intermediate compound XXa.

In one embodiment, intermediate compound XXa has the following structure:

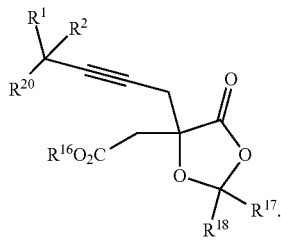

(XX)

Forming intermediate compound XVa/XV may comprise reacting intermediate compound XXa/XX with cephalotaxine or a derivative thereof under conditions effective to produce intermediate compound XVa/XV.

In one embodiment, $R^{16}$ is hydrogen and forming intermediate compound XVa/XV comprises reacting intermediate compound XXa/XX with cephalotaxine or a derivative thereof followed by reaction with an alcohol in the presence of an activating agent. In one particular embodiment, the alcohol is $R^9OH$ and the activating agent is a carboxylic acid activating agent, such as, but not limited to, trichloromethyl chloroformate, bis(trichloromethyl) carbonate, phosgene, thionyl chloride, sulfuryl chloride, carbonyl diimidazole, thiocarbonyl diimidazole, sulfuryl diimidazole, or 1-propanephosphonic anhydride.

In an alternative embodiment, $R^{16}$ is hydrogen and forming intermediate compound XVa/XV comprises reacting intermediate compound XXa/XX with cephalotaxine or a derivative thereof followed by reaction with a base and $R^9Z$, where Z represents a leaving group. Suitable leaving groups include, but are not limited to, halogen, sulfonate ester, sulfate ester, carbonate, thioester, xanthate ester, amide, phosphate ester, phosphonate ester, trialkylammonium, etc. (see also definition of Z herein).

In another embodiment, forming compound XVa/XV comprises reacting compound XXa/XX with cephalotaxine or a derivative thereof in the presence of a base, such as KHMDS, LiHMDS, NaHMDS, NaH, or $Na_2CO_3$.

In one particular embodiment, forming compound XVa/XV comprises reacting compound XXa/XX with cephalotaxine or a derivative thereof in the presence of a base, such as KHMDS, LiHMDS, NaHMDS, NaH, or $Na_2CO_3$, in an organic solvent to produce compound XVb having the formula:

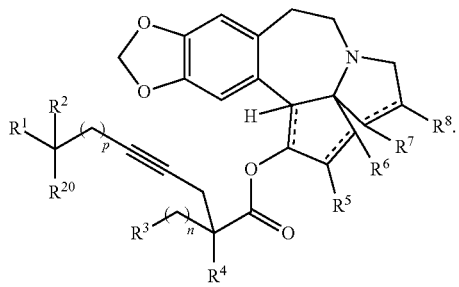

XVb

Compound XVb can then be reacted with an alcohol and activating agent or $R^9Z$ and a base, as described above, to form intermediate compound XVa/XV.

These compounds can be purified by crystallization to provide a single diastereomer of compound XVa/XV.

In accordance with these embodiments, intermediate compound XX can be provided as a substantially pure diastereomer having the structure:

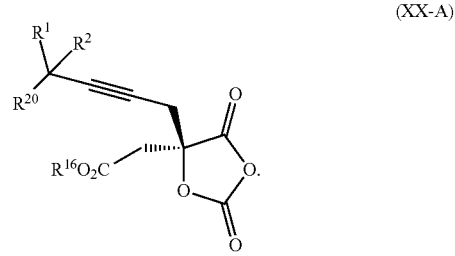

(XX-A)

Alternatively, in accordance with these embodiments, intermediate compound XX can be provided as a substantially pure diastereomer having the structure:

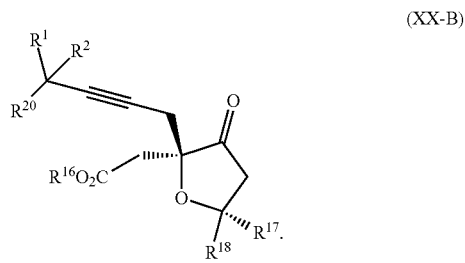

(XX-B)

In a further embodiment, the substantially pure diastereomer XX-A or XX-B is isolated by crystallization.

Another embodiment of the present invention includes providing intermediate compound XXIIIa having the formula:

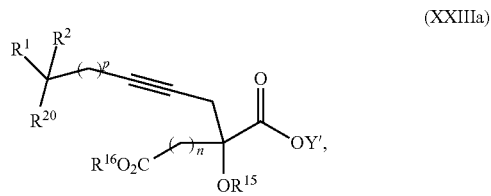

(XXIIIa)

wherein Y' is hydrogen or a protecting group; and $R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$, and forming intermediate compound XXa/XX from intermediate compound XXIIIa.

In one embodiment, intermediate compound XXIIIa has the following structure:

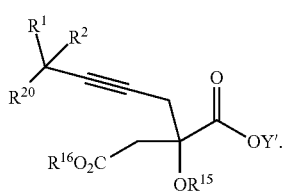
(XXIII)

In accordance with this embodiment, intermediate compound XXIII can be provided as a substantially pure diastereomer having the structure:

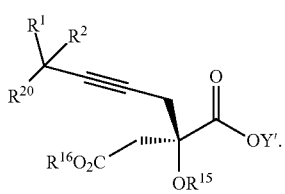
(XXIII-A)

Also in accordance with this embodiment, the compound of formula XIV can have the following structure:

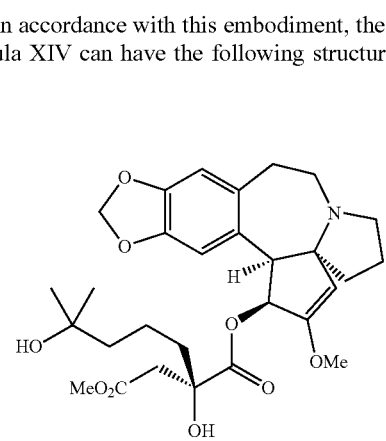

Forming intermediate compound XXa/XX may comprise reacting intermediate compound XXIIIa/XXIII with an activating agent, such as but not limited to, trichloromethyl chloroformate, bis(trichloromethyl) carbonate, phosgene, sulfuryl chloride, thionyl chloride, carbonyl diimidazole, thiocarbonyl diimidazole, sulfuryl diimidazole, thiourea, or 1-propanephosphonic anhydride under conditions effective to produce intermediate compound XXa/XX. In one particular embodiment, intermediate compound XXIIIa/XXIII is reacted with a protecting group removing agent prior to the above-described reacting step. Suitable protecting group removing agents include, but are not limited to, n-Bu$_4$NF, NH$_4$F, HF, HF·pyridine, CsF, LiBF$_4$, BF$_3$·OEt$_2$, and HCl.

In another embodiment, the process of the present invention further comprises providing intermediate compound XVIa having the formula:

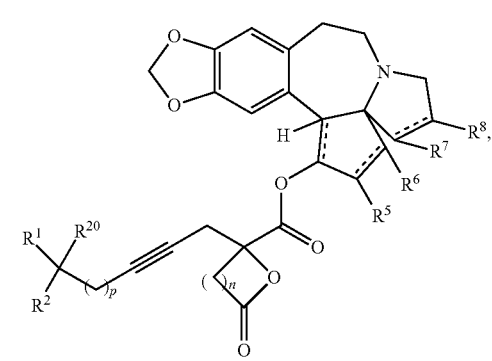
(XVIa)

and
forming intermediate compound XVa/XV from intermediate compound XVIa.

In one embodiment, intermediate compound XVIa has the following structure:

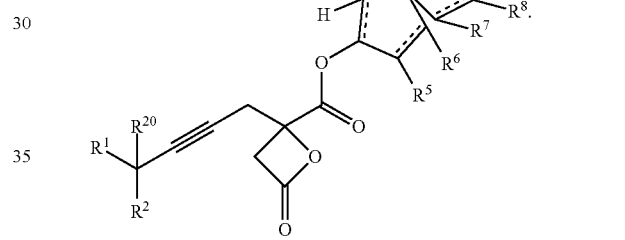
(XVI)

In another embodiment, intermediate compound XVI is provided as a substantially pure diastereomer having the structure:

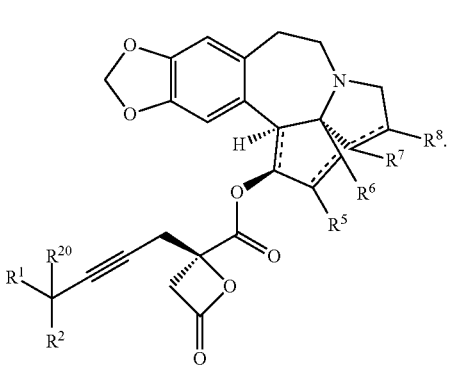
(XVI-A)

In yet another embodiment, forming intermediate compound XVa/XV comprises reacting intermediate compound XVIa/XVI with a base or under Lewis acid catalysis conditions effective to produce compound XVa/XV.

In a further embodiment, the process further comprises providing intermediate compound XVIIa having the formula:

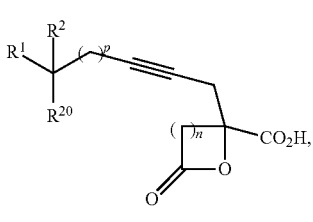

(XVIIa)

and
forming intermediate compound XVIa/XVI from intermediate compound XVIIa.

In one embodiment, intermediate compound XVIIa has the following structure:

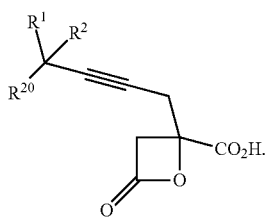

(XVII)

In accordance with this embodiment, intermediate compound XVII can be provided as a substantially pure diastereomer having the structure:

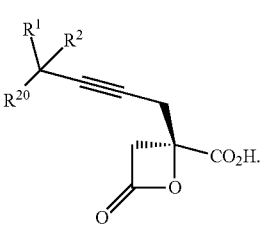

(XVII-A)

Also in accordance with this embodiment, forming intermediate compound XVIa/XVI may comprise reacting intermediate compound XVIIa/XVII with cephalotaxine or a derivative thereof under conditions effective to produce compound XVIa/XVI.

In a further embodiment, the process comprises providing intermediate compound XVIIIa having the formula:

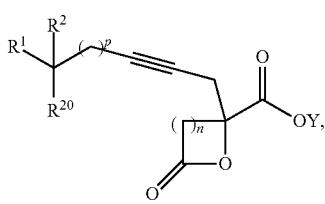

(XVIIIa)

wherein Y is a protecting group, and
forming intermediate compound XVIIa/XVII from intermediate compound XVIIIa.

In one embodiment, intermediate compound XVIIIa has the following structure:

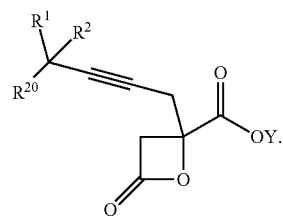

(XVIII)

In accordance with this embodiment, intermediate compound XVIII can be provided as a substantially pure diastereomer having the structure:

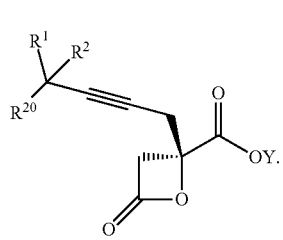

(XVIII-A)

Also in accordance with this embodiment, forming intermediate compound XVIIa/XVII may comprise reacting intermediate compound XVIIIa/XVIII with a protecting group removing agent under conditions effective to produce intermediate compound XVIIa/XVII. Suitable protecting group removing agents include, but are not limited to, n-Bu$_4$NF, NH$_4$F, HF, HF.pyridine, CsF, LiBF$_4$, BF$_3$.OEt$_2$, and HCl. Removal of the protecting group from compound XVIIIa/XVIII to produce compound XVIIa/XVII does not affect the alkyne functionality.

In yet another embodiment, the process further comprises providing intermediate compound XIXa having the formula:

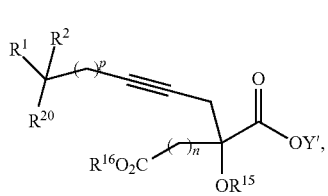

(XIXa)

wherein
Y' is hydrogen or a protecting group; and
R$^{15}$ and R$^{16}$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^{10}$$_2$)(R$^9$)$_2$, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$, and forming intermediate compound XVIIIa/XVIII from intermediate compound XIXa.

In one embodiment, intermediate compound XIXa has the following structure:

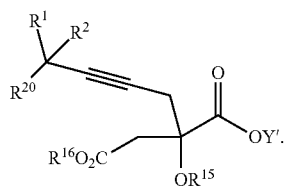

(XIX)

In accordance with this embodiment, intermediate compound XIX can be provided as a substantially pure diastereomer having the structure:

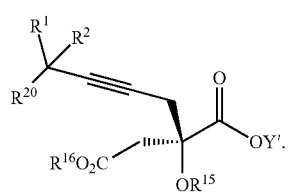

(XIX-A)

Also in accordance with the embodiment, forming intermediate compound XVIIIa/XVIII may comprise reacting intermediate compound XIXa/XIX with a reagent that activates the intermediate for substitution under conditions effective to produce intermediate compound XVIIIa/XVIII. Suitable reagents include, but are not limited to, BOP—Cl, CDI, alkyl chloroformates, thionyl chloride, $T_3P$, aroyl chlorides, and disubstitutedphosphoryl halides.

Another embodiment of the present invention comprises providing intermediate compound XXa having the formula:

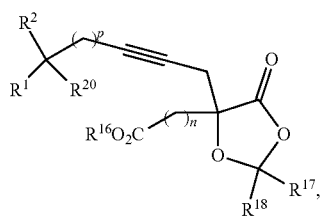

(XXa)

wherein $R^{17}$ is t-Bu, phenyl, naphthyl, $CF_3$, $CCl_3$, $CBr_3$, or $C_1$-$C_6$ alkoxy;

$R^{18}$ is H, Me, $CF_3$, $CCl_3$, $CBr_3$, or $C_1$-$C_6$ alkoxy;

or $R^{17}$ and $R^{18}$ combine with the carbon to which they are attached to form an internally bridged cycloalkyl, wherein the internally bridged cycloalkyl can be optionally substituted from 1 to 6 times with a substituent independently selected in each occurrence from $C_{1-6}$ alkyl and $C_{1-6}$ alkyl further substituted with —$SO_2N(C_{1-6}$ alkyl$)_2$; or $R^{17}$ and $R^{18}$ are taken together with the atom to which they are attached to form a carbonyl, thiocarbonyl, sulfoxide, or sulfone, and forming intermediate compound XIXa/XIX from intermediate compound XXa.

In one embodiment, intermediate compound XXa has the following structure:

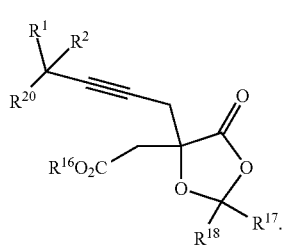

(XX)

In accordance with this embodiment, intermediate compound XX can be provided as a substantially pure diastereomer having the structure:

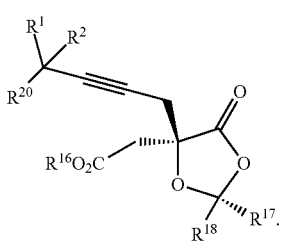

(XX-A)

The substantially pure diastereomer XX-A can be isolated by crystallization.

Another embodiment relates to the process as described above, wherein forming intermediate compound XIXa/XIX comprises reacting intermediate compound XXa/XX with a protecting group introducing agent under conditions effective to produce intermediate compound XIXa/XIX.

In one particular embodiment, the protecting group introducing agent has the formula Y'—OH. In another particular embodiment, the protecting group introducing agent is TMS $(CH_2)_2OH$.

In another embodiment, the process of the present invention further comprises providing intermediate compound VIIIa having the formula:

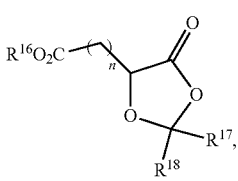

(VIIIa)

and forming intermediate compound XXa/XX from intermediate compound VIIIa.

In one embodiment, intermediate compound VIIIa has the following structure:

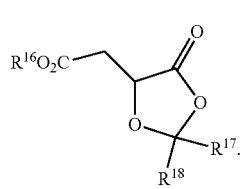

(VIII)

In a further embodiment, forming intermediate compound XXa/XX comprises reacting intermediate compound VIIIa/VIII with a base and then with a compound of formula XXIa:

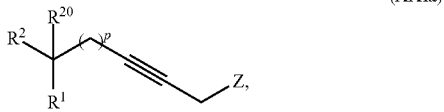

(XXIa)

wherein Z is selected from the group consisting of halogen, —OSO$_2$R$^{19}$, —OSO$_3$R$^{19}$, —OCOR$^9$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, —N(R$^{19}$)$_3$$^+$ and R$^{19}$ is selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$, under conditions effective to produce the intermediate compound XXa/XX.

In one embodiment, the compound of formula XXIa has the following structure:

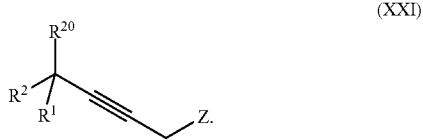

(XXI)

In another embodiment, the compound of formula XXI has the structure:

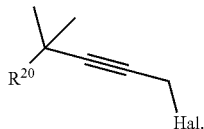

In accordance with any of the embodiments described herein, compound I/XIV can be purified by, for example, crystallization and chromatography. In one embodiment, compound I/XIV is isolated at a purity of at least 99%.

The present invention also relates to intermediates used in the above-described methods of the present invention.

Such intermediates include, for example, a compound of formula XVa:

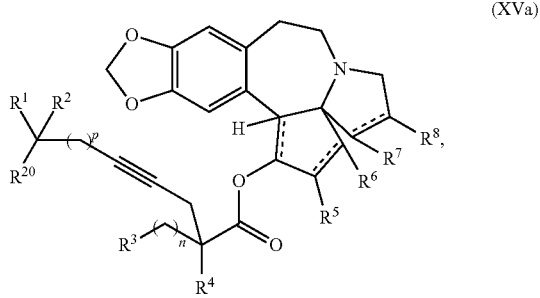

(XVa)

wherein

R$^1$ and R$^2$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R; or R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or R$^1$ and R$^2$ are taken together with the atom to which they are attached to form a carbonyl, thiocarbonyl, sulfoxide, or sulfone;

R$^3$ is hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^{10}$$_2$)(R$^9$)$_2$, heterocycle, aryl, or heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$;

R$^4$ is hydrogen, —N(R$^{10}$)$_2$, —OR$^{10}$, —SR$^{10}$, acyl, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^{10}$$_2$)(R$^9$)$_2$, heterocycle, aryl, or heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or R$^3$ and R$^4$ are taken together to form a 5- to 7-membered ring having 0-2 heteroatoms independently selected from the group consisting of nitrogen, oxygen, and sulfur, optionally substituted from 1 to 3 times with R$^{11}$;

R$^5$ is hydrogen, —OR$^{10}$, or =O;

R$^6$ is hydrogen, —OR$^{10}$, —OCO$_2$R$^{10}$, —OCOR$^{10}$, —OCOSR$^{10}$, or —OCON(R$^{10}$)$_2$;

R$^7$ and R$^8$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, heteroaryl, —SO$_2$R$^{10}$, and —CO$_2$R$^{10}$; or R$^7$ and R$^8$ are taken together to form an optionally substituted 5- to 7-membered ring having 0-2 heteroatoms independently selected from nitrogen, oxygen, and sulfur;

R$^9$ is hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, or heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$;

each R$^{10}$ is independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or two R$^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with R$^{11}$;

R$^{11}$ is independently selected at each occurrence from a substituent in the group consisting of halogen, —NO$_2$, —OR$^{12}$, —NR$^{12}$R$^{13}$, —NR$^{12}$C(O)$_2$R$^{13}$, —NR$^{12}$C(O) NR$^{12}$R$^{13}$, —S(O)$_m$R$^{13}$, —CN, —C(O)R$^{13}$, —C(O) NR$^{12}$R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, wherein each of C$_1$-C$_6$ alkyl, C$_2$-C$_6$ alkenyl, C$_2$-C$_6$ alkynyl, C$_3$-C$_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —NR$^{12}$R$^{13}$;

R$^{12}$ and R$^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or R$^{12}$ and R$^{13}$ are taken together with the nitrogen to which they are attached to form a piperidine, pyrrolidine, piperazine, N-methylpiperazine, morpholine, or thiomorpholine ring;

R$^{14}$ is $C_1$-$C_4$ alkyl, $C_1$-$C_4$ haloalkyl, or phenyl;

R$^{20}$ is hydrogen, halogen, —NO$_2$, —OR$^{12}$, —OX, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with R$^{11}$;

X is a protecting group;

each ═ independently designates a single or double bond;

n is an integer from 0 to 9;

p is an integer from 0 to 3; and m is an integer from 0 to 2, or a pharmaceutically acceptable salt thereof, or a solvate thereof.

In one embodiment, compound XVa has the following formula:

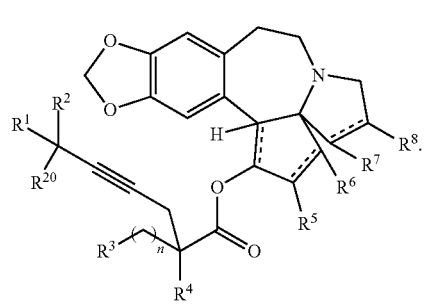

(XV)

In another embodiment, the compound is a substantially pure diastereomer having the structure:

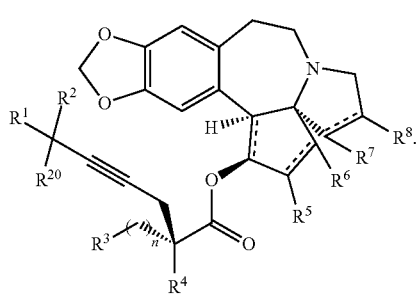

(XV-A)

In yet another embodiment, the compound has the structure:

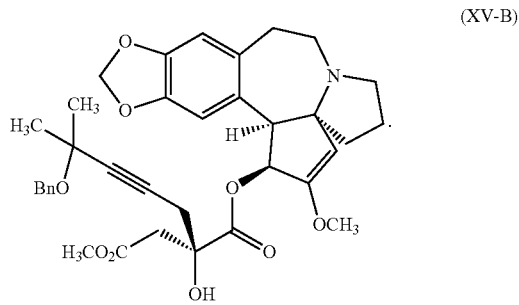 [SMILES: COC(=O)C[C@](O)(CC#CC(C)(C)OCc1ccccc1)C(=O)O[C@@H]1C(OC)=C[C@]23CCCN2CCc2cc4c(cc2[C@H]13)OCO4]

(XV-B)

In a further embodiment, the compound has the structure:

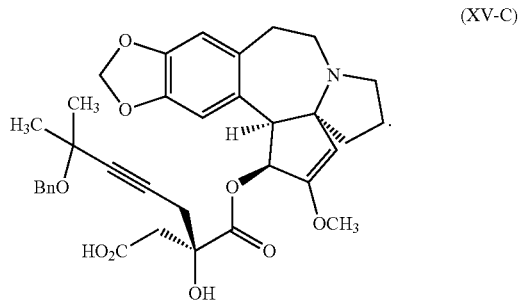 [SMILES: COC1=C[C@]23CCCN2CCc2cc4c(cc2[C@@H]3[C@@H]1OC(=O)[C@@](O)(CC#CC(C)(C)OCc1ccccc1)CC(=O)O)OCO4]

(XV-C)

Another embodiment of the present invention relates to a compound of formula XVIa:

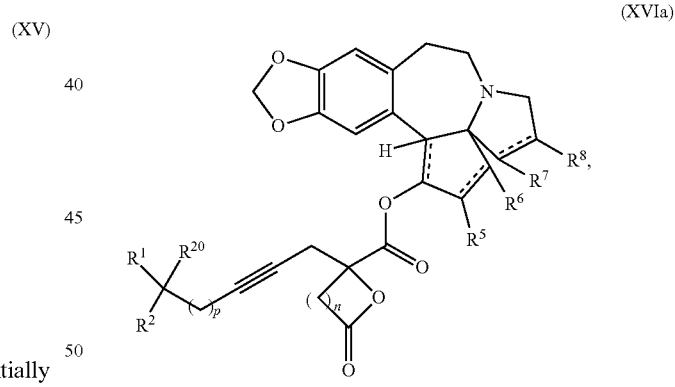

(XVIa)

wherein

R$^1$ and R$^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with R$^{11}$; or R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or R$^1$ and R$^2$ are taken together with the atom to which they are attached to form a carbonyl, thiocarbonyl, sulfoxide, or sulfone;

$R^5$ is hydrogen, $—OR^{10}$, or $=O$;

$R^6$ is hydrogen, $—OR^{10}$, $—OCO_2R^{10}$, $—OCOR^{10}$, $—OCOSR^{10}$, or $—OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, $—SO_2R^{10}$, and $—CO_2R^{10}$; or $R^7$ and $R^8$ are taken together to form an optionally substituted 5- to 7-membered ring having 0-2 heteroatoms independently selected from nitrogen, oxygen, and sulfur;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, $—NO_2$, $—OR$, $—NR^{12}R^{13}$, $—NR^{12}C(O)_2R^{13}$, $—NR^{12}C(O)NR^{12}R^{13}$, $—S(O)_mR^{13}$, $—CN$, $—C(O)R^{13}$, $—C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $—CN$, and $—NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $—C(O)R^{14}$, phenyl, or benzyl, wherein phenyl or benzyl is optionally substituted with 1 to 3 substituents independently selected at each occurrence from the group consisting of halogen, $—CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, $—NO_2$, $—OR^{12}$, $—OX$, $—NR^{12}R^{13}$, $—NR^{12}C(O)_2R^{13}$, $—NR^{12}C(O)NR^{12}R^{13}$, $—S(O)_mR^{13}$, $—CN$, $—C(O)R^3$, $—C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

n is an integer from 0 to 9;

m is an integer from 0 to 2;

p is an integer from 0 to 3; and each ⁓ independently designates a single or double bond, or a pharmaceutically acceptable salt thereof, or a solvate thereof.

In one embodiment, compound XVIa has the following formula:

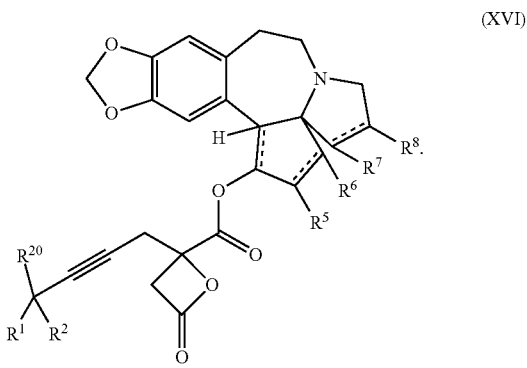

(XVI)

In another embodiment, the compound is a substantially pure diastereomer having the structure:

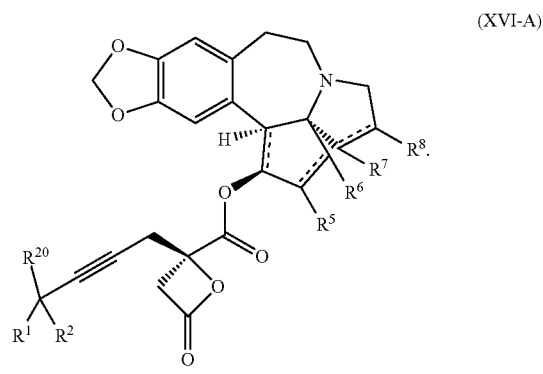

(XVI-A)

A further aspect of the present invention relates to a compound of formula XVIIa:

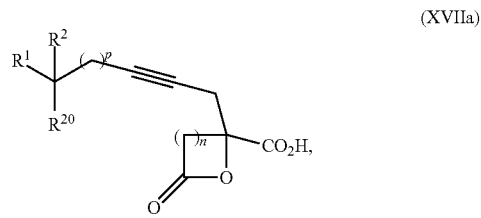

(XVIIa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, $—NO_2$, $—OR^{12}$, $—NR^{12}R^{13}$, $—NR^{12}C(O)_2R^{13}$, $—NR^{12}C(O)$ $NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring; and $R^{14}$ is $C_1$-$C_4$ alkyl, $C_1$-$C_4$ haloalkyl, or phenyl;

$R^{20}$ is hydrogen, halogen, $-NO_2$, $-OR^{12}$, $-OX$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;
n is an integer from 0 to 9;
m is an integer from 0 to 2; and
p is an integer from 0 to 3;

or a pharmaceutically acceptable salt thereof, or a solvate thereof.

In one embodiment, compound XVIIa has the following formula:

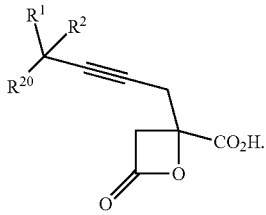

(XVII)

In another embodiment, the compound is a substantially pure diastereomer having the structure:

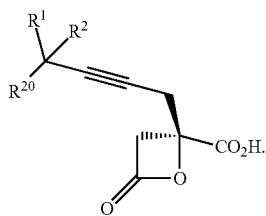

(XVII-A)

The present invention also relates to a compound of formula XVIIIa:

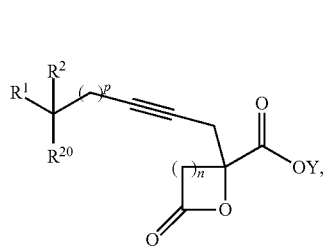

(XVIIIa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, $-NO_2$, $-OR^{12}$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, $-NO_2$, $-OR^{12}$, $-OX$, $-NR^{12}R^{13}$, $-NR^{12}C(O)_2R^{13}$, $-NR^{12}C(O)NR^{12}R^{13}$, $-S(O)_mR^3$, $-CN$, $-C(O)R^3$, $-C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;
n is an integer from 0 to 9;
m is an integer from 0 to 2;
p is an integer from 0 to 3; and
Y is hydrogen or a protecting group, or a pharmaceutically acceptable salt thereof, or a solvate thereof.

In one embodiment, compound XVIIIa has the following formula:

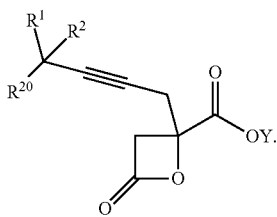

(XVIII)

In another embodiment, the compound is a substantially pure diastereomer having the structure:

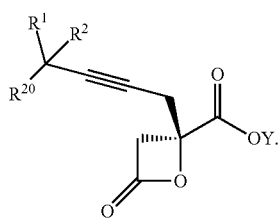

(XVIII-A)

The present invention also relates to a compound of formula XIXa:

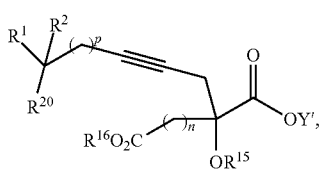

(XIXa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

n is an integer from 0 to 9;

m is an integer from 0 to 2;

p is an integer from 0 to 3; and

Y' is hydrogen or a protecting group, or a pharmaceutically acceptable salt thereof, or a solvate thereof.

In one embodiment, compound XIXa has the following structure:

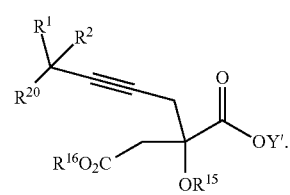

(XIX)

In another embodiment, the compound is a substantially pure diastereomer having the structure:

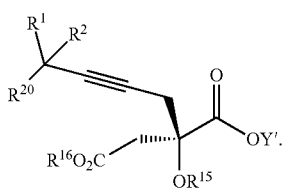

(XIX-A)

Another aspect of the present invention relates to a compound of formula XXa:

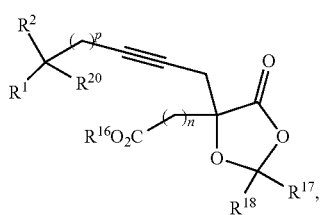

(XXa)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{16}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{17}$ is t-Bu, phenyl, naphthyl, $CF_3$, $CCl_3$, $CBr_3$, or $C_1$-$C_6$ alkoxy;

$R^{18}$ is H, Me, $CF_3$, $CCl_3$, $CBr_3$, or $C_1$-$C_6$ alkoxy; or $R^{17}$ and $R^{18}$ combine with the carbon to which they are attached to form an internally bridged cycloalkyl, wherein the internally bridged cycloalkyl can be optionally substituted from 1 to 6 times with a substituent independently selected in each occurrence from $C_{1-6}$ alkyl and $C_{1-6}$ alkyl further substituted with —$SO_2N(C_{1-6}$ alkyl$)_2$; or $R^{17}$ and $R^{18}$ are taken together with the atom to which they are attached to form a carbonyl, thiocarbonyl, sulfoxide, or sulfone;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

n is an integer from 0 to 9;

m is an integer from 0 to 2; and p is an integer from 0 to 3, or a pharmaceutically acceptable salt thereof, or a solvate thereof.

In one embodiment, compound XXa has the following structure:

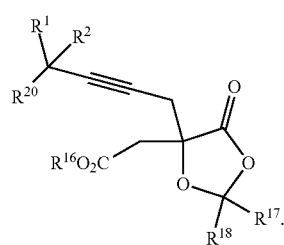

(XX)

In another embodiment, the compound is a substantially pure diastereomer having the structure:

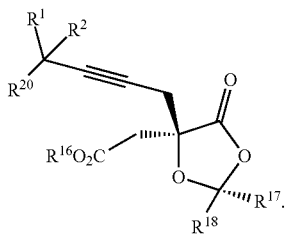

(XX-A)

In a further embodiment, the compound is a substantially pure diastereomer having the structure:

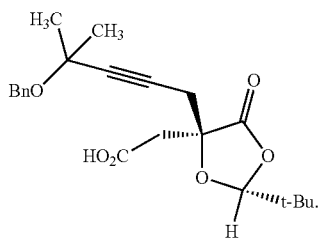

(XX-B)

Another embodiment of the present invention relates to a process for preparation of a product compound of formula IX:

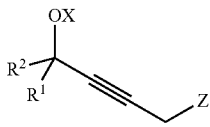

(IX)

wherein

X is hydrogen or a protecting group;

Z is selected from the group consisting of halogen, —OSO$_2$R$^{19}$, —OSO$_3$R$^{19}$, —OCOR$^{19}$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, and —N(R$^{19}$)$_3^+$.

R$^1$ and R$^2$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or R$^1$ and R$^2$ are taken together with the atom to which they are attached to form a carbonyl, thiocarbonyl, sulfoxide, or sulfone;

R$^{11}$ is independently selected at each occurrence from a substituent in the group consisting of halogen, —NO$_2$, —OR$^{12}$, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, wherein each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted with 1 to 3 substituents independently selected at each occurrence from the group consisting of C$_1$-C$_4$ alkyl, C$_1$-C$_4$ alkoxy, halogen, Ar, —CN, and —NR$^{12}$R$^{13}$;

R$^{12}$ and R$^{13}$ are each independently hydrogen, C$_1$-C$_4$ alkyl, C$_1$-C$_4$ haloalkyl, C$_1$-C$_4$ alkoxyalkyl, C$_3$-C$_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, C$_1$-C$_4$ alkyl, C$_1$-C$_4$ haloalkyl, and C$_1$-C$_4$ alkoxy; or R$^{12}$ and R$^{13}$ are taken together with the nitrogen to which they are attached to form a piperidine, pyrrolidine, piperazine, N-methylpiperazine, morpholine, or thiomorpholine ring;

R$^{14}$ is C$_1$-C$_4$ alkyl, C$_1$-C$_4$ haloalkyl, or phenyl;

R$^{19}$ is selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; and m is an integer from 0 to 2, or a pharmaceutically acceptable salt thereof, or a solvate thereof;

said method comprising providing intermediate compound X having the formula:

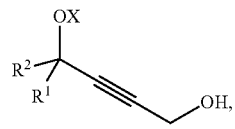

(X)

and forming the product compound of formula IX from intermediate compound X.

Yet another embodiment of the present invention relates to a process for preparation of a product compound of formula XXIa:

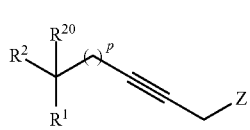

(XXIa)

wherein

Z is selected from the group consisting of halogen, —OSO$_2$R$^{19}$, —OSO$_3$R$^{19}$, —OCOR$^{19}$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, and —N(R$^{19}$)$_3^+$;

R$^1$ and R$^2$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^3$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

p is an integer from 0 to 3; and m is an integer from 0 to 2, or a pharmaceutically acceptable salt thereof, or a solvate thereof;

said method comprising:

providing intermediate compound XXIVa having the formula:

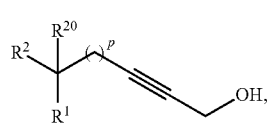

(XXIVa)

and forming the product compound of formula XXIa from intermediate compound XXIVa.

In one embodiment, compound XXIa has the structure:

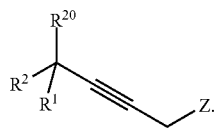

(XXI)

In another embodiment, compound XXIVa has the structure:

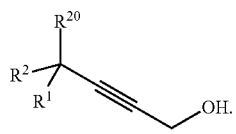

(XXIV)

In a further embodiment, Z is a halogen.

In yet another embodiment, $R^1$ and $R^2$ are each $C_1$-$C_6$ alkyl.

In one embodiment, forming compound XXIa/XXI comprises subjecting compound XXIVa/XXIV to halogenation/deoxygenation conditions.

In a further embodiment, the process of the present invention further comprises providing intermediate compound XXVa having the formula:

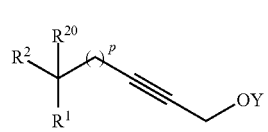

(XXVa)

wherein Y is a protecting group, and forming intermediate compound XXIVa/XXIV from intermediate compound XXVa.

In one embodiment, compound XXVa has the structure:

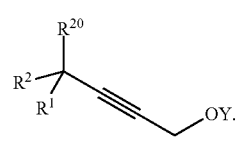

(XXV)

In a further embodiment, forming compound XXIVa/XXIV comprises reacting compound XXVa/XXV with a protecting group removing agent. Suitable protecting group removing agents include, but are not limited to, n-$Bu_4NF$, $NH_4F$, HF, HF.pyridine, CsF, $LiBF_4$, $BF_3.OEt_2$, and HCl.

Another embodiment relates to the process as described above, wherein Y is a trisubstituted silyl group.

In another embodiment, the process of the present invention further comprises providing intermediate compound XIIa having the formula:

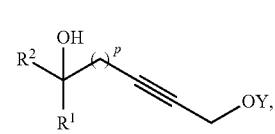

(XIIa)

and
forming intermediate compound XXVa/XXV from intermediate compound XIIa.

In one embodiment, compound XIIa has the structure:

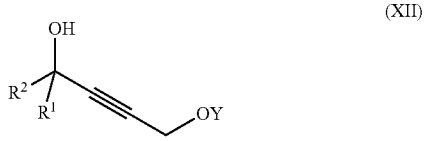

(XII)

In a further embodiment, forming intermediate compound XXVa/XXV comprises subjecting intermediate compound XIIa/XII to deprotonation in the presence of a base and a compound comprising X.

The present invention also relates to intermediates used in the above-described methods of the present invention.

Such intermediates include, for example, a compound of formula XXIa:

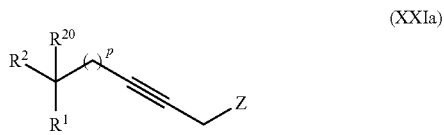

(XXIa)

wherein

Z is selected from the group consisting of halogen, $-OSO_2R^{19}$, $-OSO_3R^{19}$, $-OCOR^{19}$, $-OCO_2R^{19}$, $-OCSR^{19}$, $-OCS_2R^{19}$, $-OCN(R^{19})_2$, $-OPO(R^{19})_2$, $-OPO(OR^{19})_2$, and $-N(R^{19})_3{}^+$;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, $-NO_2$, $-OR$, $-NR^{12}R^{13}$, $-NR^{12}C(O)_2R^{13}$, $-NR^{12}C(O)N^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{20}$ is hydrogen, halogen, $-NO_2$, $-OR^{12}$, $-OX$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^3$, $-C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

p is an integer from 0 to 3; and m is an integer from 0 to 2, or a pharmaceutically acceptable salt thereof, or a solvate thereof.

In one embodiment, compound XXIa has the structure:

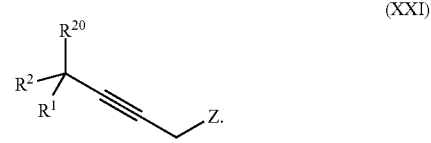

(XXI)

Another compound of the present invention comprises intermediate compound XXVIa having the formula:

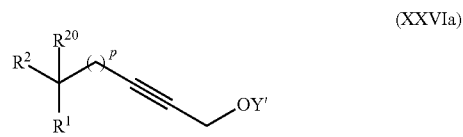

(XXVIa)

wherein

Y' is hydrogen or a protecting group;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^{11}$ is independently selected at each occurrence from a substituent in the group consisting of halogen, $-NO_2$, $-OR$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)$ $NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —C(O)$R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring; and $R^{14}$ is $C_1$-$C_4$ alkyl, $C_1$-$C_4$ haloalkyl, or phenyl;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

p is an integer from 0 to 3; and m is an integer from 0 to 2, or a pharmaceutically acceptable salt thereof, or a solvate thereof.

In one embodiment, compound XXVIa has the structure:

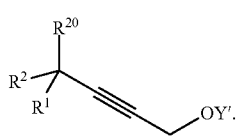

(XXVI)

In one embodiment, Z is halogen in any of the compounds and processes described above.

In another embodiment, Y is a trisubstituted silyl group in any of the compounds and processes described above.

In yet another embodiment, $R^1$ and $R^2$ are each $C_1$-$C_6$ alkyl in any of the compounds and processes described above.

In a further embodiment, $R^1$ and $R^2$ are each $C_1$-$C_6$ alkyl, $R^3$ is $CO_2R^9$, $R^4$ and $R^5$ are each $OR^{10}$, and $R^6$, $R^7$, and $R^8$ are each H in any of the compounds and processes described above.

Compounds of the invention may be synthesized according to the schemes described below. The reagents and conditions described are intended to be exemplary and not limiting. As one of skill in the art would appreciate, various analogs may be prepared by modifying the synthetic reactions such as using different starting materials, different reagents and different reaction conditions (e.g., temperature, solvent, concentration, etc.).

Schemes 1/1a-2/2a and Example 3 below show the preparation of omacetaxine and derivatives thereof in accordance with one embodiment of the present invention.

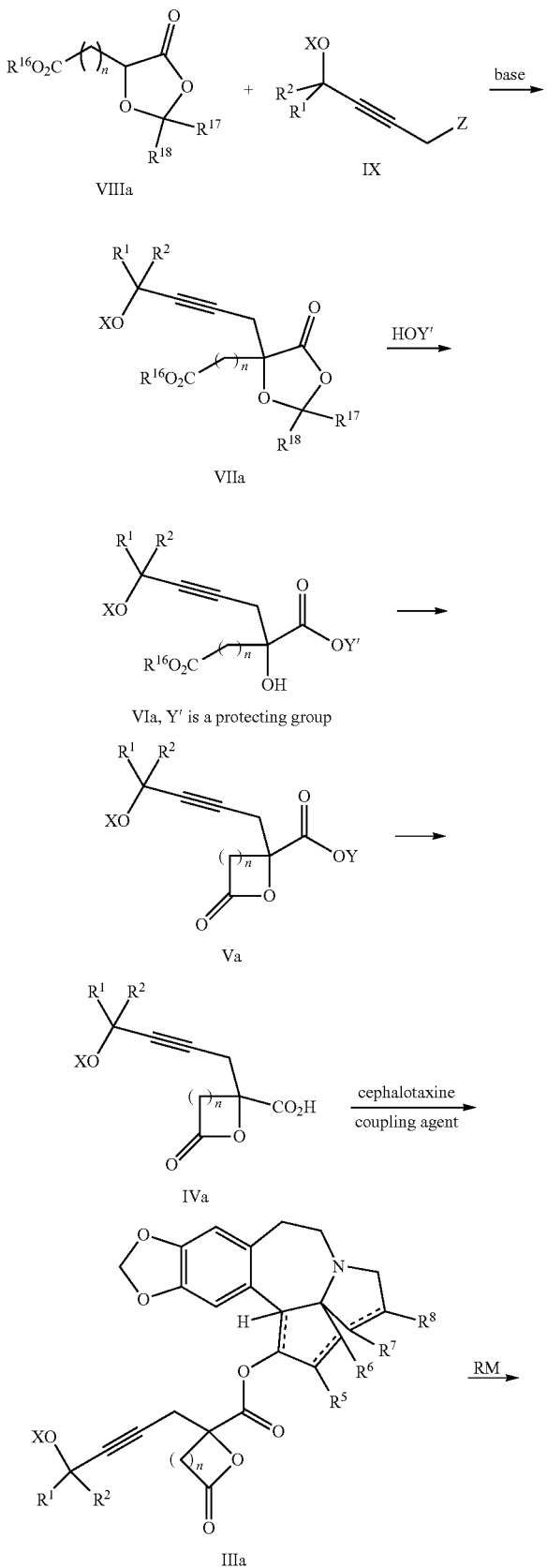

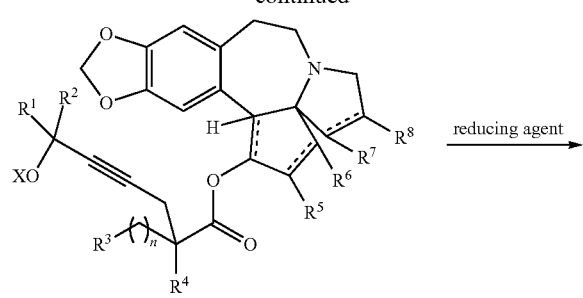
II
R⁴ is OH
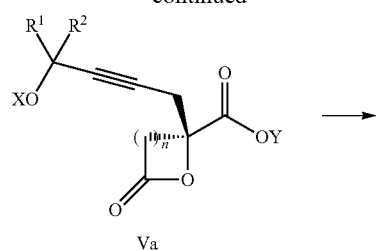
Va
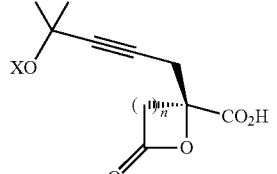
IVa
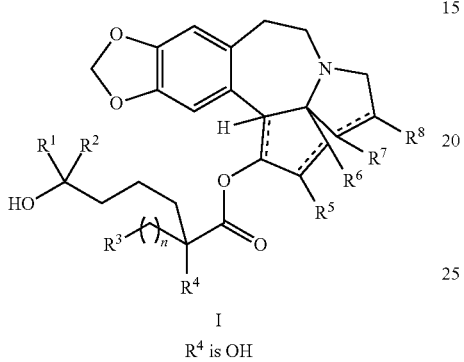
I
R⁴ is OH
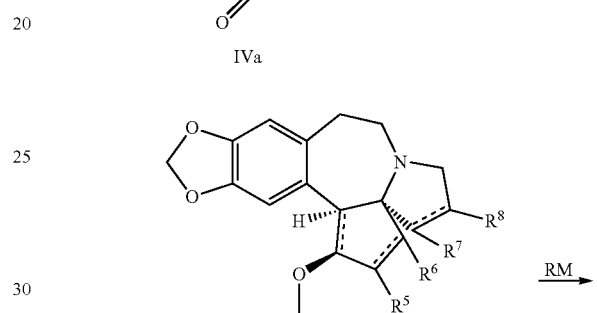
IIIa
Scheme 1a
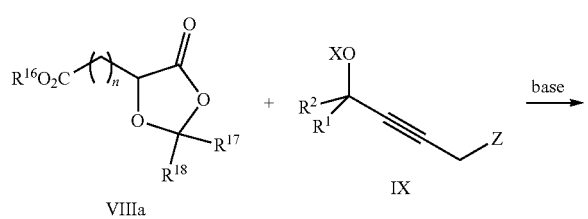
VIIIa + IX
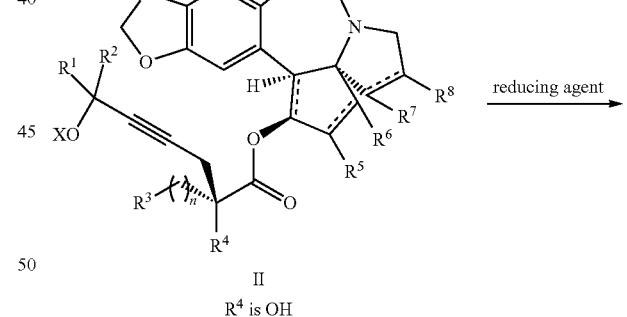
II
R⁴ is OH
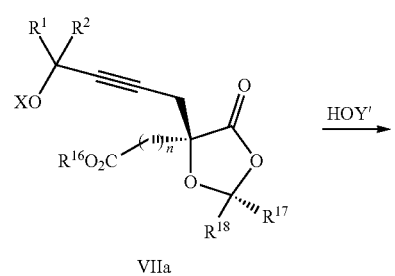
VIIa
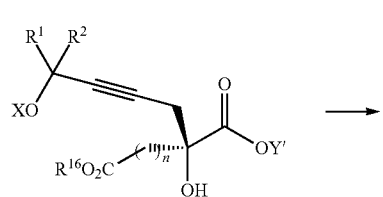
VIa, Y' is a protecting group
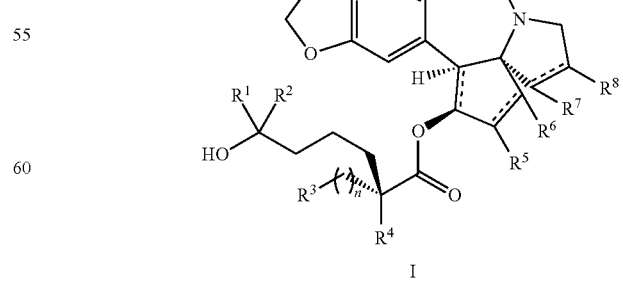
I
R⁴ is OH Scheme 2
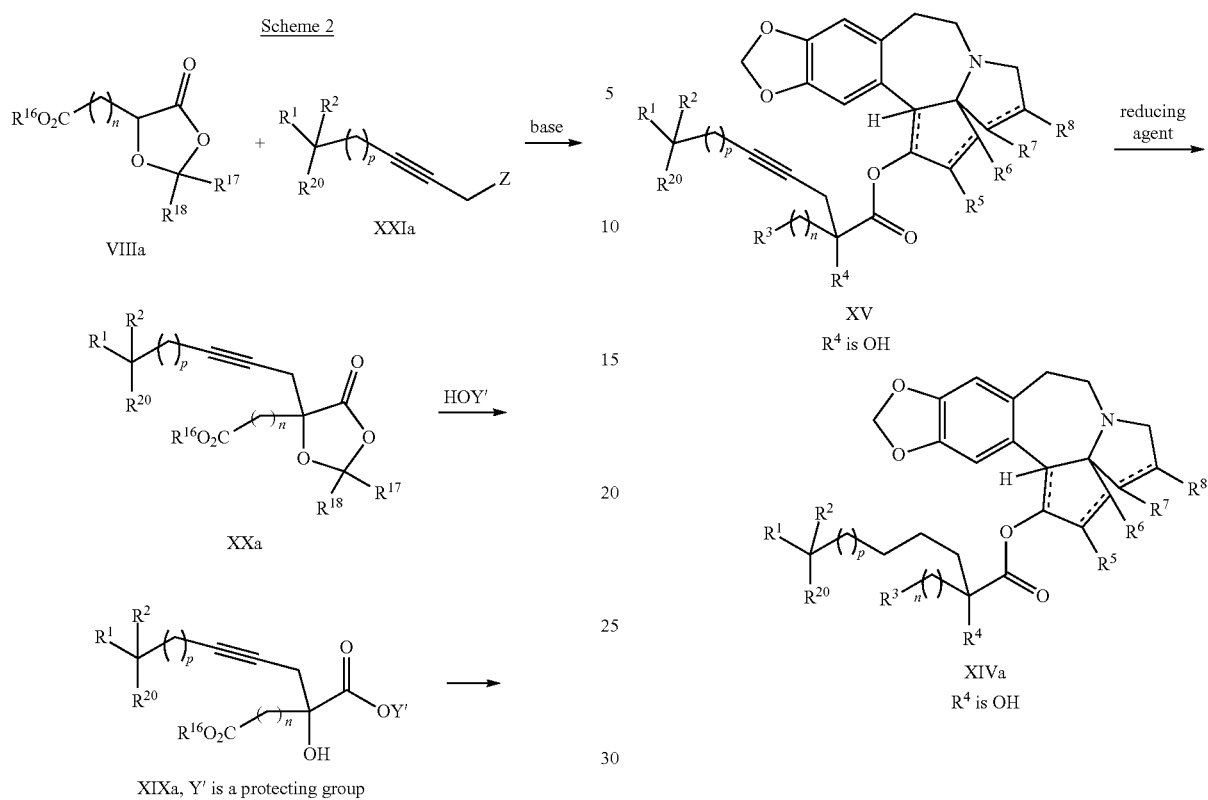
Scheme 2a
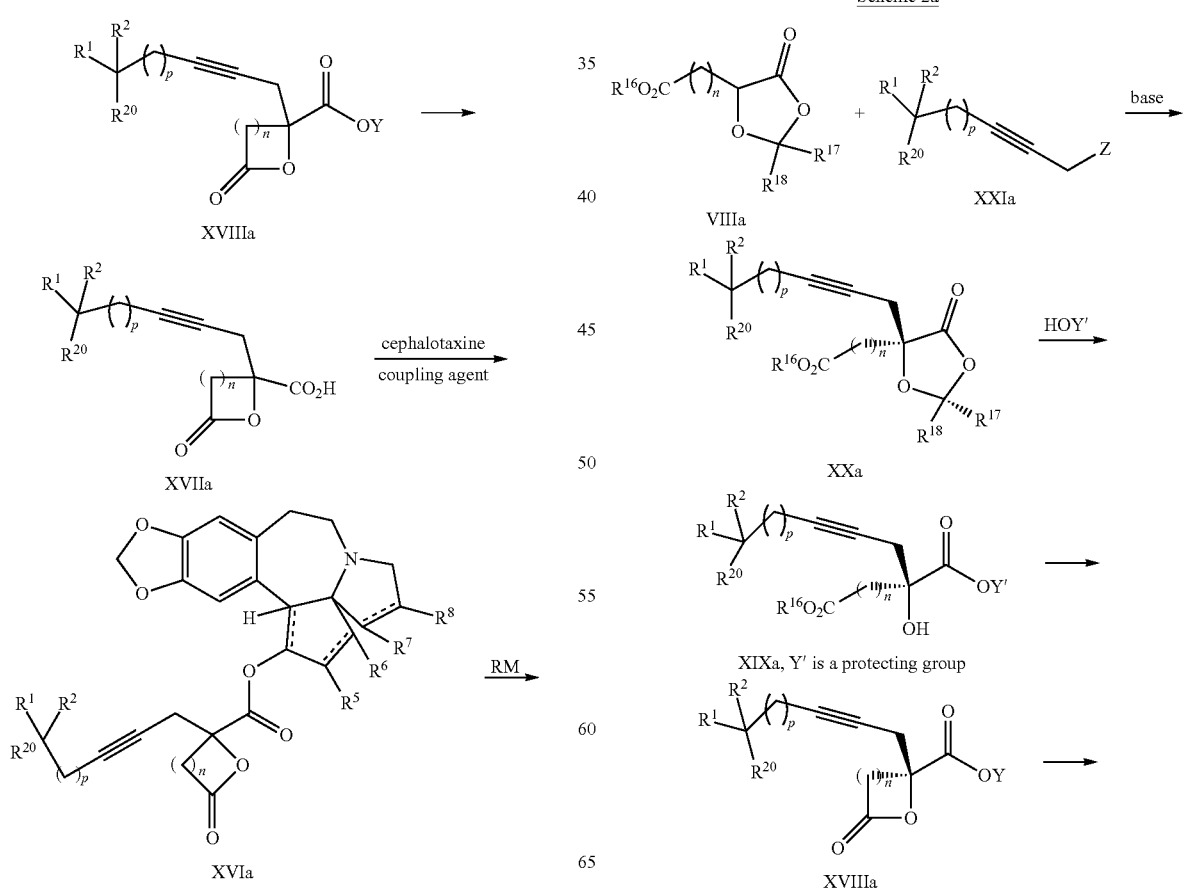

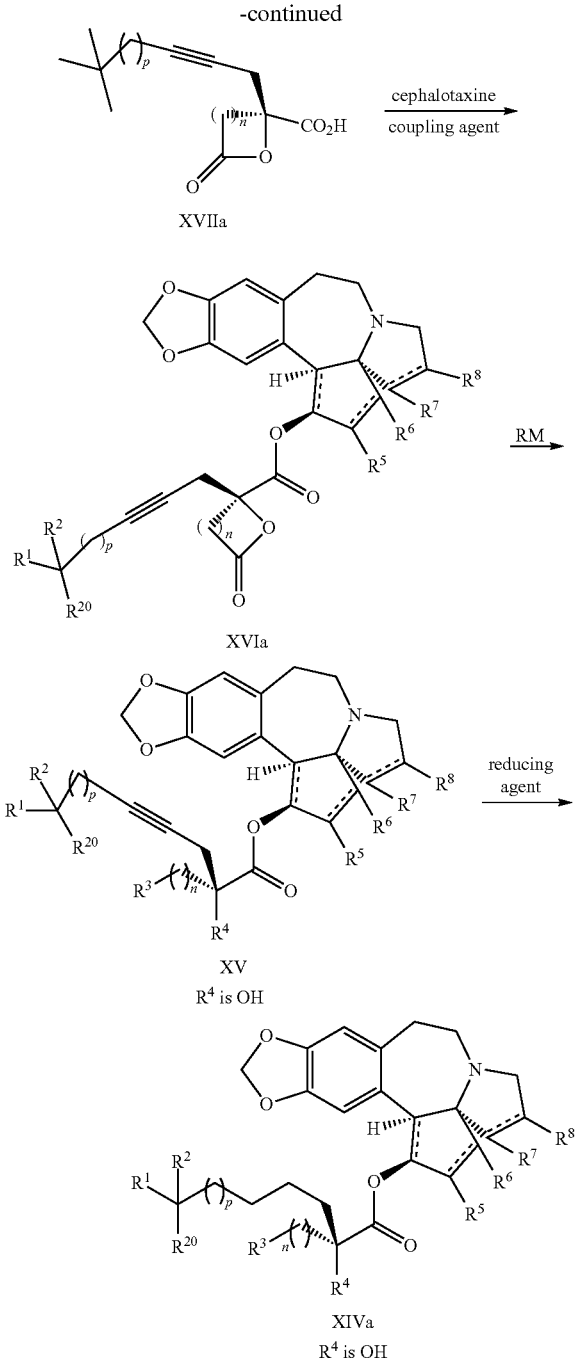

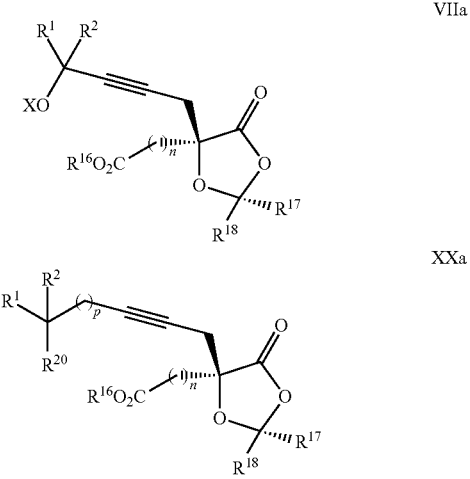

In accordance with Schemes 1/1a-2/2a above, Compounds VIIIa and IX or VIIIa and XXIa are reacted in the presence of a base, such as LiHMDS, to produce Compound VIIa or XXa. In one embodiment, Z is a halogen. However, Z can be any other suitable leaving group, such as sulfonate ester, sulfate ester, carbonate, thioester, xanthate ester, amide, phosphate ester, phosphonate ester, trialkylammonium, etc. (see also definition of Z herein). In another embodiment, $R^1$ and $R^2$ are each $C_1$-$C_6$ alkyl. In this step, an alkyne functionality is installed early in synthesis via Compound IX/XXIa. This alkyne chain functionality allows crystallization of the product at that step to isolate a single diastereomer of Compound VIIa or XXa as shown Diastereomeric purity of Compound VIIa produced in accordance with the method of Scheme 1/1a is illustrated in FIG. 1. Compound VIIa or XXa is reacted with a protecting group introducing agent Y'—OH, such as TMS($CH_2$)$_2$OH, under conditions effective to produce Compound VIa/XIXa. In one embodiment, Compound VIIa or XXa is reacted with a protecting group introducing agent in the presence of a base, such as LiHMDS, to produce Compound VIa/XIXa. In this particular embodiment, introduction of a protecting group (e.g., 2-(trimethylsilyl)ethyl ester protecting group) at the tertiary carboxylic acid in the presence of the primary carboxylic acid allows removal of the protecting group at a later stage without affecting the alkyne functionality. Forming Compound Va or XVIIIa includes reacting Compound VIa or XIXa with a reagent that activates the intermediate for substitution under conditions effective to produce Compound Va or XVIIIa. Suitable reagents when forming the oxetanone (Compound Va or XVIIIa) from Compound VIa/XIXa include, but are not limited to, BOP—Cl, CDI, alkyl chloroformates, thionyl chloride, $T_3P$, aroyl chlorides, and disubstitutedphosphoryl halides. Removal of the protecting group from Compound Va/XVIIIa to produce Compound IVa/XVIIa does not affect the alkyne functionality. This can be achieved by reacting Compound Va/XVIIIa with a protecting group removing agent under conditions effective to produce Compound IVa/XVIIa. Suitable protecting group removing agents include, but are not limited to, n-$Bu_4$NF, $NH_4F$, HF, HF.pyridine, CsF, $LiBF_4$, $BF_3.OEt_2$, and HCl. The tertiary carboxylic acid of Compound IVa/XVIIa couples with cephalotaxine or a derivative thereof (single isomer reagent) to provide a single diastereomer of compound IIIa/XVIa. In one embodiment, Compound II/XVa is formed by reacting Compound IIIa/XVIa with a base or under Lewis acid catalysis conditions and the resulting product compound I/XIV is achieved by reacting Compound II/XVa with a reducing agent. When X is a protecting group, reduction of the alkyne with concomitant reductive deprotection of the tertiary alcohol moiety is achieved in the last step. However, a two-step protocol can be used, in which the alkyne to ethylene reduction takes place and is followed by removal of X, where X is a protecting group, in a subsequent step.

Example 3 illustrates a particular embodiment of the method shown in Scheme 1, where X is an arylmethyl protecting group that can undergo carbon-oxygen bond cleavage under reductive conditions.

Novel reactant IX and XXIa described in Schemes 1/1a and 2/2a can be produced according to Schemes 3-4 described below and as described in Examples 1 and 2.

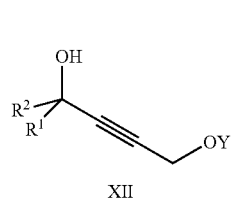

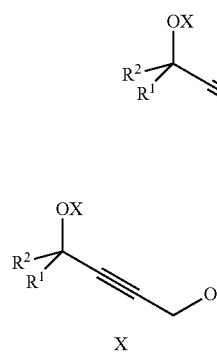

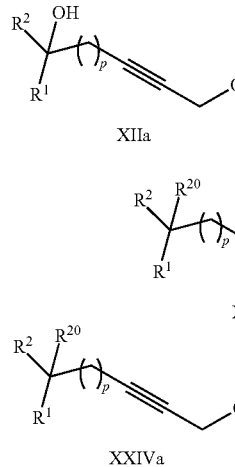

In accordance with Schemes 3 and 4, Compound X/XXIVa can be subjected to halogenation/deoxygenation conditions with a reagent combination such as sulfuryl chloride, trisubstitutedphosphine/NBS, or trisubstitutedphosphine/iodine to form Compound IX/XXIa. Compound X/XXIVa can be reacted with a sulfonyl halide under basic conditions, followed by halogenation by displacement with, for example, lithium bromide or sodium iodide. In one embodiment, Z is a halogen. In another embodiment, $R^1$ and $R^2$ are each $C_1$-$C_6$ alkyl. Compound X/XXIVa can be formed by reacting compound XI/XXVa with a protecting group removing agent, such as n-$Bu_4$NF, $NH_4$F, HF, HF.pyridine, CsF, $LiBF_4$, $BF_3$.$OEt_2$, and HCl. In one embodiment, Y is a trisubstituted silyl group. Compound XI/XXVa can be formed by reacting compound XI/XIIa with an oxygen protecting group precursor, such as iodomethane, dimethyl sulfate, (trimethylsilyl)diazomethane, benzyl 2,2,2-trichloroacetimidate, benzyl bromide, 4-methoxylbenzyl chloride, allyl bromide, chloromethyl methyl ether, 2-methoxyethoxymethyl chloride, benzyl chloromethyl ether and trityl chloride, under basic conditions, such as sodium hydride, potassium tert-butoxide, n-butyllithium, lithium diisopropylamide and metal bis(trimethylsilyl)amides.

Schemes 5/5a-6/6a and Example 4 below show another embodiment of the preparation of omacetaxine and derivatives thereof in accordance with the present invention via ring-opening of an activated alkylated malic acid scaffold.

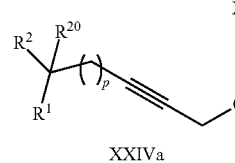

Scheme 5a
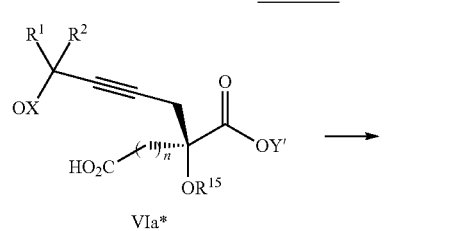
VIa*
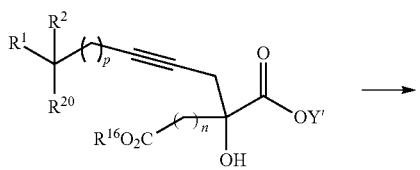
XXIIIa**
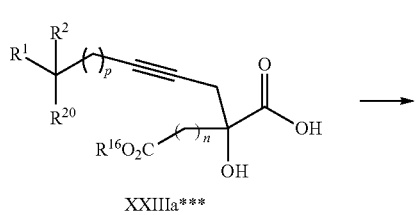
XXIIIa***
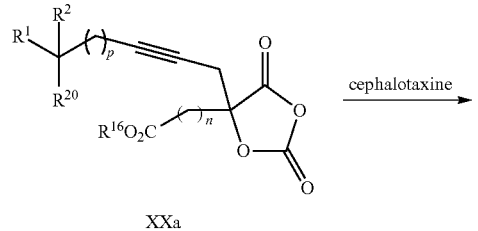
XXa
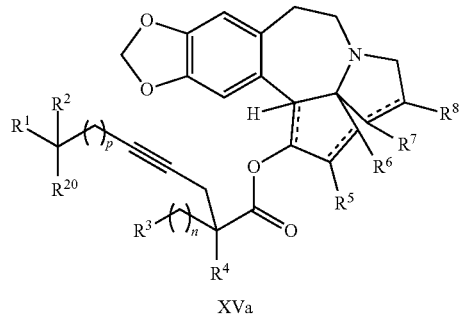
XVa
VIa**
VIa***
VIIa
II
Scheme 6
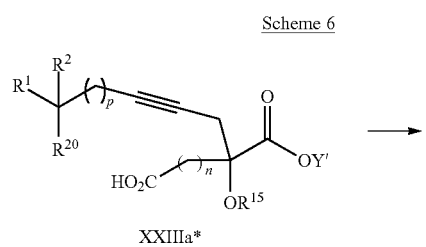
XXIIIa*
Scheme 6a
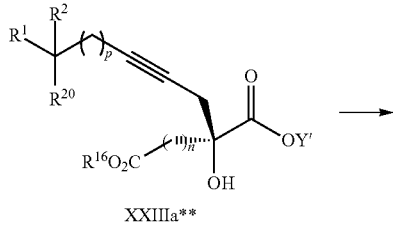
XXIIIa*
XXIIIa**

-continued

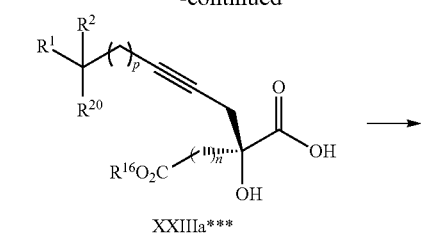

XXIIIa***

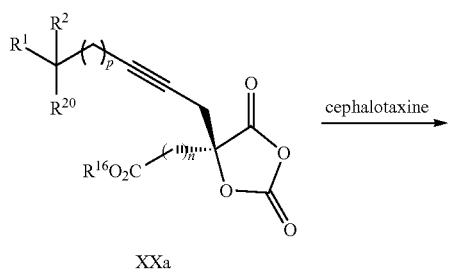

XXa cephalotaxine →

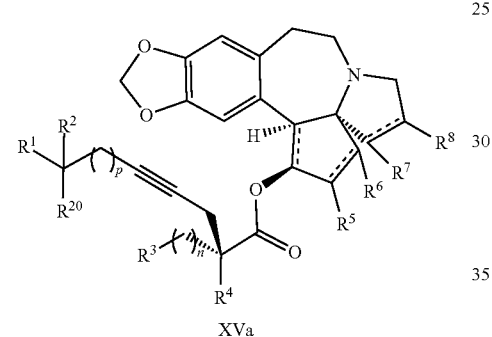

XVa

As shown above, Compound VIa*/XXIIIa* is reacted with a carboxylic acid protecting group reagent under appropriate conditions, such as chlorotrimethylsilane with an alcohol, an acid chloride or chloroformate and an alcohol under basic conditions, a haloalkane or dialkyl sulfate under basic conditions, or a diazoalkane and an alkyl chloromethyl ether. As further shown above, Compound VIa/XXIIIa is reacted with a protecting group removing agent, such as n-Bu$_4$NF, NH$_4$F, HF, HF.pyridine, CsF, LiBF$_4$, BF$_3$.OEt$_2$, or HCl, to form Compound VIa*/XXIIIa*. Compound VIIa/XXa is produced by reacting Compound VIa*/XXIIIa* with, for example but not limited to, trichloromethyl chloroformate, bis(trichloromethyl) carbonate, phosgene, sulfuryl chloride, thionyl chloride, carbonyl diimidazole, thiocarbonyl diimidazole, sulfuryl diimidazole, thiourea, or 1-propanephosphonic anhydride. Compound IIIXVa is formed by reacting Compound VIIa/XXa with cephalotaxine or a derivative thereof under conditions effective to produce Compound II/XVa.

Schemes 7/7a-8/8a and Example 5 below show another embodiment of the preparation of omacetaxine and derivatives thereof in accordance with the present invention via direct ring-opening of an alkylated malic acid scaffold.

Scheme 7

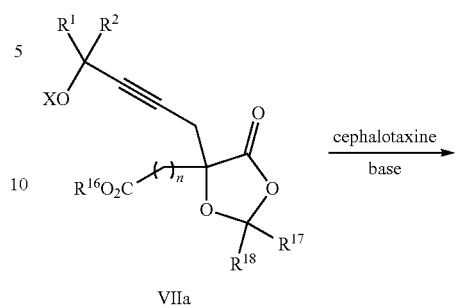

VIIa cephalotaxine base →

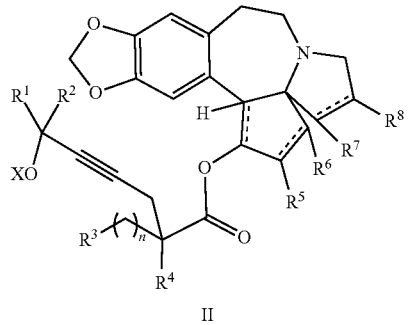

II

Scheme 7a

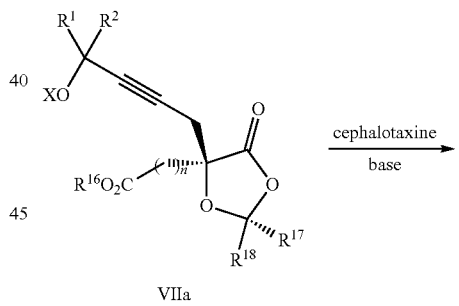

VIIa cephalotaxine base →

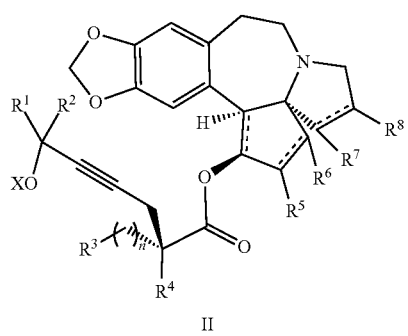

II

Scheme 8

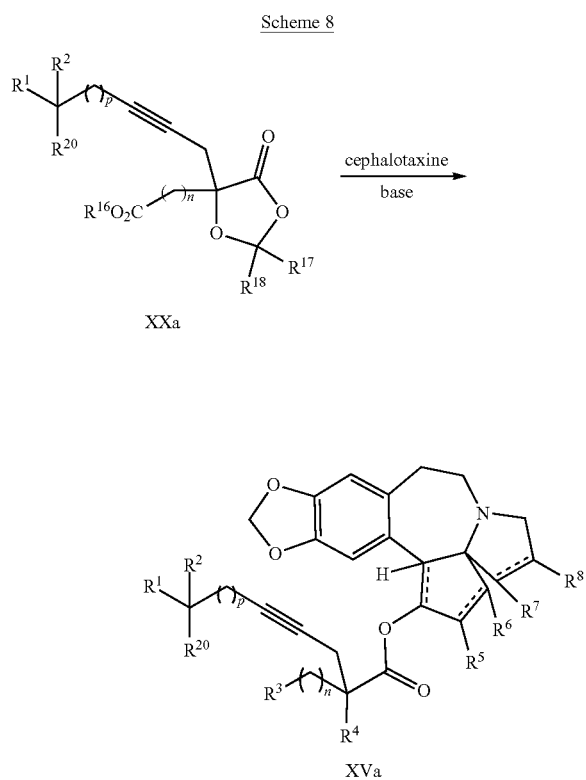

Scheme 8a

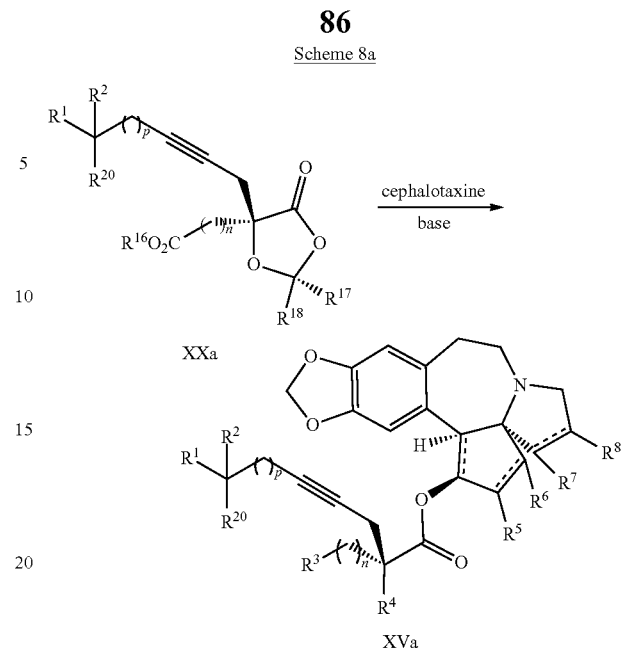

In one embodiment, reaction of VIIa or XXa and cephalotaxine or a derivative thereof in the presence of base, such as KHMDS, produces Compound II or XVa. These compounds can be purified by crystallization to provide a single diastereomer of Compound II or XVa.

Schemes 9/9a-10/10a and Example 6 below show another embodiment of the preparation of omacetaxine and derivatives thereof in accordance with the present invention via direct ring-opening of an alkylated malic acid scaffold.

Scheme 9

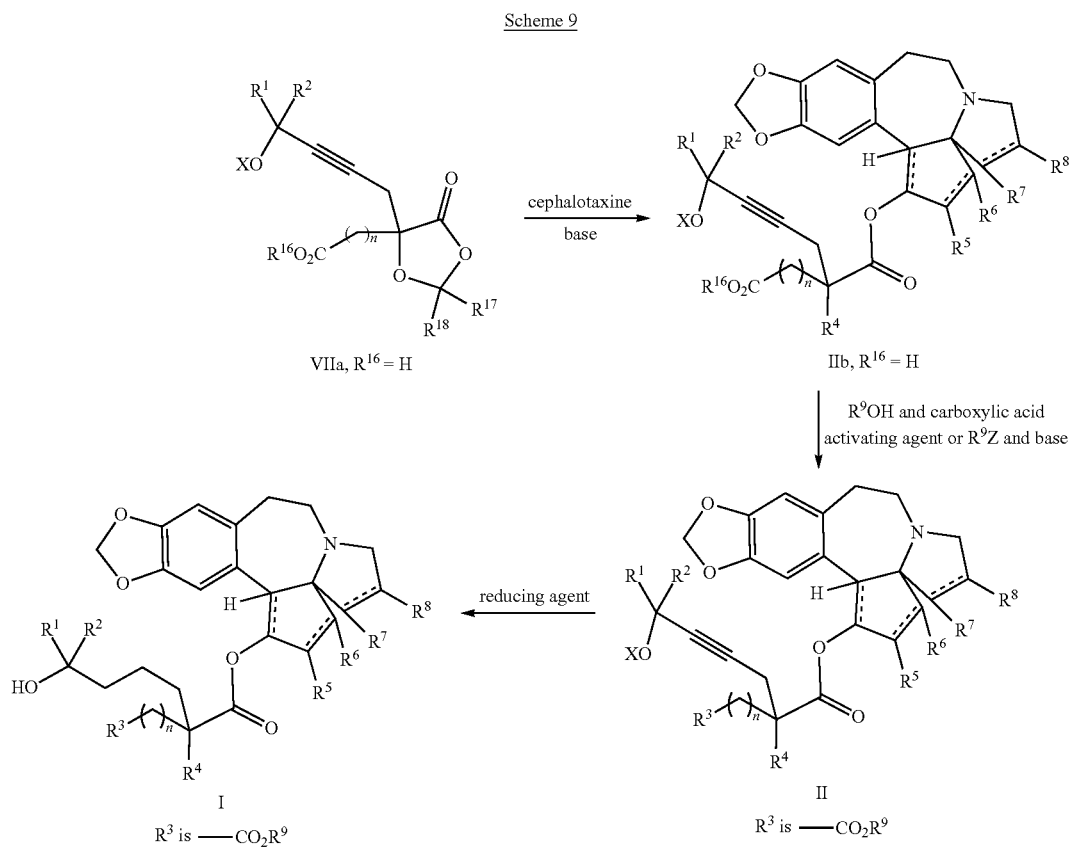

Scheme 9a
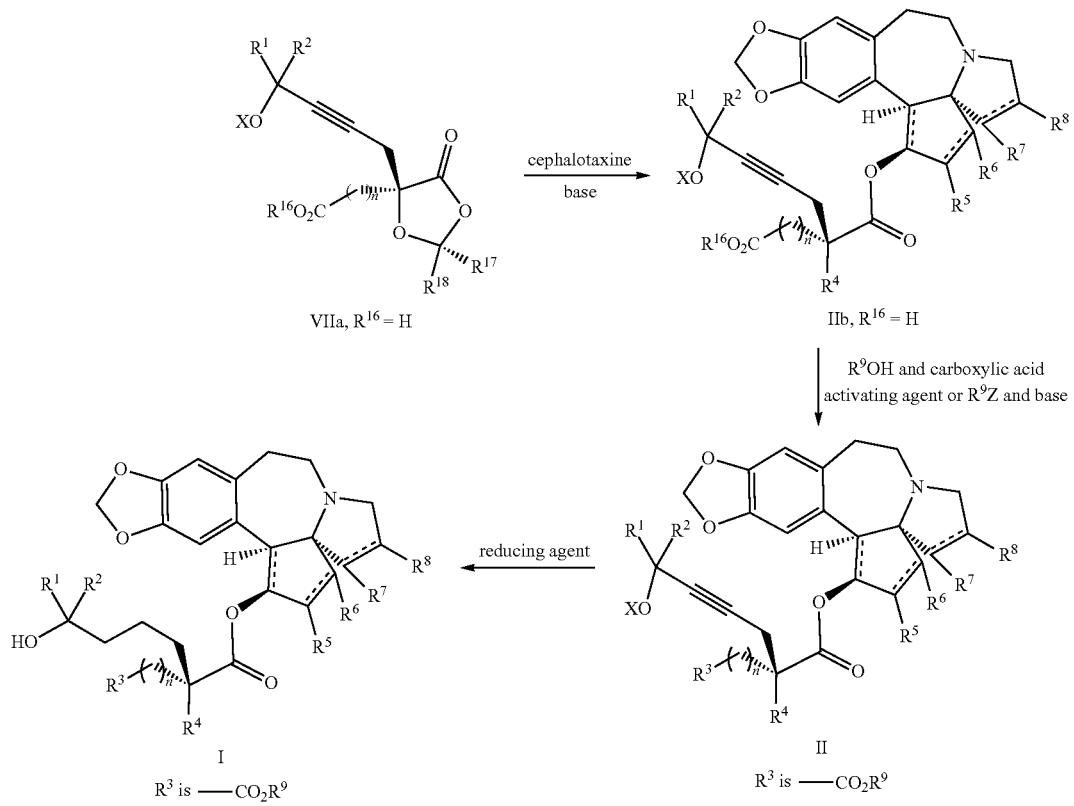
Scheme 10
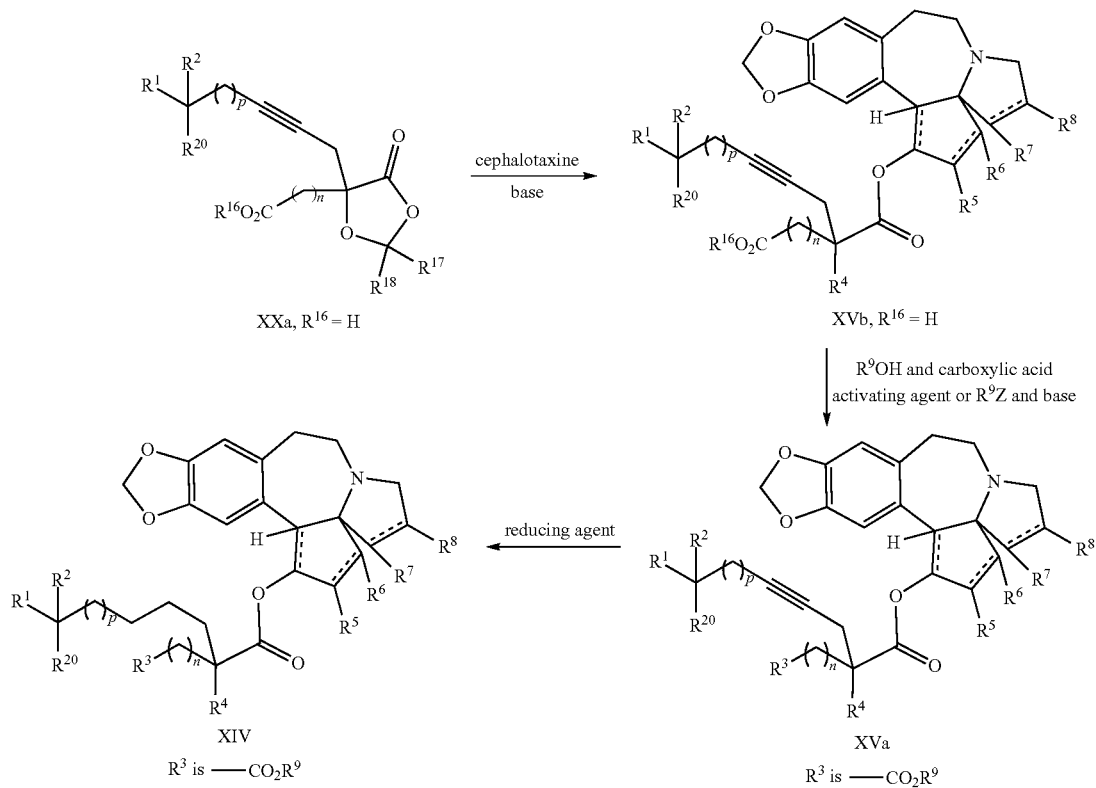

Scheme 10a

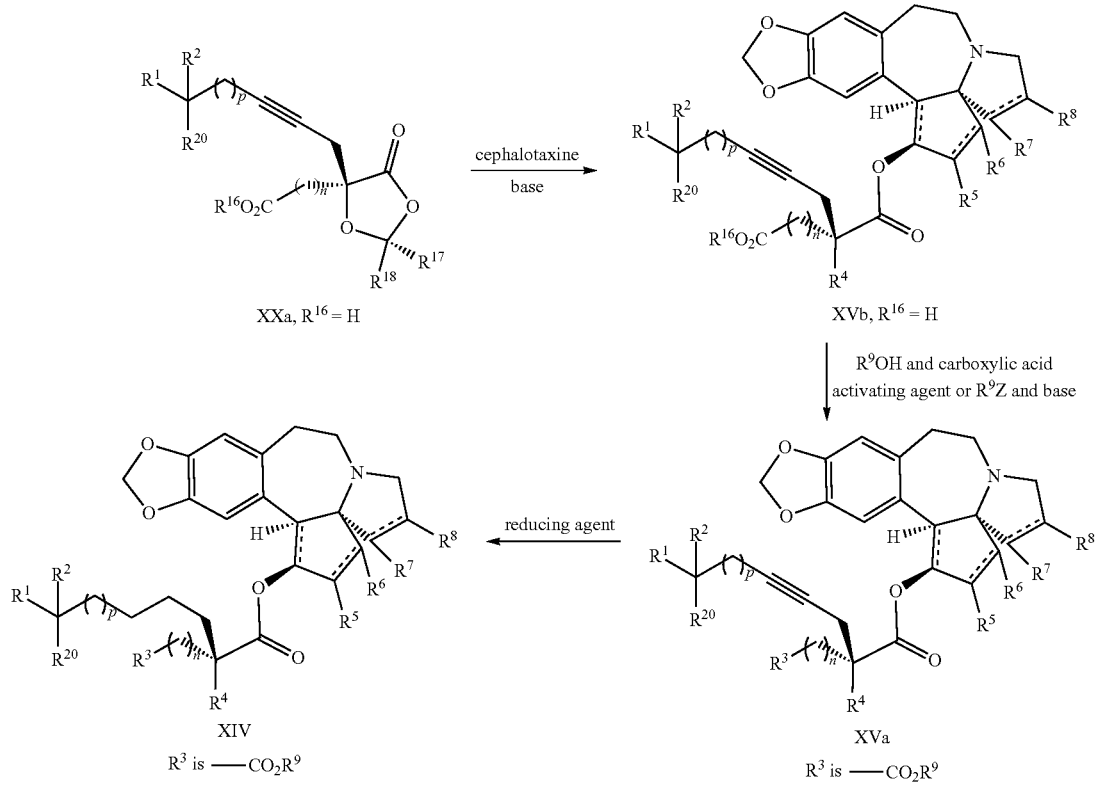

In one embodiment, reaction of VIIa/XXa with cephalotaxine or a derivative thereof in the presence of base, such as KHMDS, LiHMDS, NaHMDS, NaH, or $Na_2CO_3$, in an organic solvent, provides Compound IIb/XVb. Subsequent treatment of IIb/XVb with an alcohol ($R^9OH$) and a carboxylic acid activating agent provides Compound II/XVa. Alternatively, treatment of IIb/XVb with base and $R^9Z$, where Z represents a leaving group, as described above, provides II/XVa. Reduction of the alkyne functionality of II/XVa with concomitant removal of the oxygen protecting group (if present) provides IXIV. In one embodiment, treatment of VIIa/XXa and cephalotaxine in THF with KHMDS furnishes IIb/XVb which can be purified to provide a single diastereomer by crystallization from a THF/DCM mixture. Subsequent treatment of IIb/XVb with oxalyl chloride and methanol provides the methyl ester of II/XVa as the hydrochloride salt which can be isolated by crystallization from ethyl acetate. Hydrogenation of II/XVa using Pearlman's catalyst and triethylamine in methanol, followed by the addition of acetic acid provides IXIV. Crude IXIV can then be purified by crystallization from toluene, the isolated material further purified by reverse phase chromatography and isolated >99% pure by a final crystallization from an organic solvent such as toluene or isopropyl acetate.

The processes of the present invention are more efficient than those of the prior art and are amenable to large scale production. Omacetaxine and omacetaxine derivatives produced by the methods of the present invention may be used in a therapeutically effective amount to treat proliferative and infectious diseases, in particular CML.

1. As described herein, the present invention relates to a process for preparation of a product compound of formula (I):

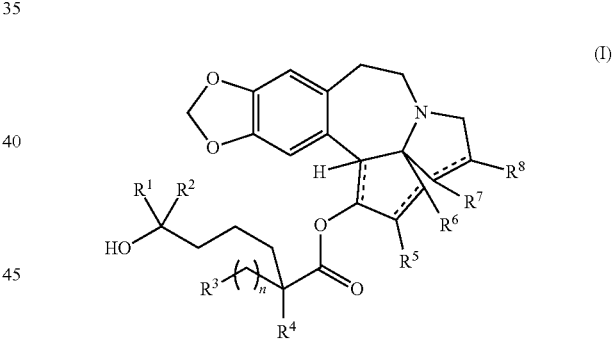

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with substituents as defined below in $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —C(OR$^{10}$)(R$^9$)$_2$, —C(NR$^{10}$$_2$)(R$^9$)$_2$, heterocycle, aryl, or heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$;

R$^4$ is hydrogen, —N(R$^{10}$)$_2$, —OR$^{10}$, —SR$^{10}$, acyl, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^{10}$$_2$)(R$^9$)$_2$, heterocycle, aryl, or heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or R$^3$ and R$^4$ are taken together to form a 5- to 7-membered ring having 0-2 heteroatoms independently selected from the group consisting of nitrogen, oxygen, and sulfur, optionally substituted from 1 to 3 times with R$^{11}$;

R$^5$ is hydrogen, —OR$^{10}$, or =O;

R$^6$ is hydrogen, —OR$^{10}$, —OCO$_2$R$^{10}$, —OCOR$^{10}$, —OCOSR$^{10}$, or —OCON(R$^{10}$)$_2$;

R$^7$ and R$^8$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, heteroaryl, —SO$_2$R$^{10}$, and —CO$_2$R$^{10}$; or R$^7$ and R$^8$ are taken together to form an optionally substituted 5- to 7-membered ring having 0-2 heteroatoms independently selected from nitrogen, oxygen, and sulfur;

R$^9$ is hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, or heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$;

each R$^{10}$ is independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or two R$^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with R$^{11}$;

R$^{11}$ is independently selected at each occurrence from a substituent in the group consisting of halogen, —NO$_2$, —OR$^{12}$, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, wherein each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted with 1 to 3 substituents independently selected at each occurrence from the group consisting of C$_1$-C$_4$ alkyl, C$_1$-C$_4$ alkoxy, halogen, Ar, —CN, and —NR$^{12}$R$^{13}$;

R$^{12}$ and R$^{13}$ are each independently hydrogen, C$_1$-C$_4$ alkyl, C$_1$-C$_4$ haloalkyl, C$_1$-C$_4$ alkoxyalkyl, C$_3$-C$_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, C$_1$-C$_4$ alkyl, C$_1$-C$_4$ haloalkyl, and C$_1$-C$_4$ alkoxy; or R$^{12}$ and R$^{13}$ are taken together with the nitrogen to which they are attached to form a piperidine, pyrrolidine, piperazine, N-methylpiperazine, morpholine, or thiomorpholine ring;

R$^{14}$ is C$_1$-C$_4$ alkyl, C$_1$-C$_4$ haloalkyl, or phenyl;

each ═ independently designates a single or double bond; and n is an integer from 0 to 9;

m is an integer from 0 to 2, or a pharmaceutically acceptable salt thereof, or a solvate thereof, said process comprising:

providing a first intermediate compound having the structure:

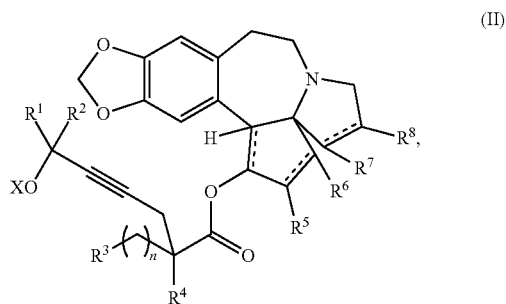

(II)

wherein X is hydrogen or a protecting group, and forming the product compound of formula (I) from the first intermediate compound.

2. In one embodiment of this process, X is an arylmethyl or heteroarylmethyl protecting group, optionally substituted from 1 to 3 times with C$_1$-C$_6$ alkyl.

3. In another embodiment of this process, X is selected from the group consisting of alkanoyl, aryloyl, benzyloxycarbonyl, allyloxycarbonyl, (β-trimethylsilylethoxy)carbonyl, (dialkylamino)carbonyl, triphenylmethyl, benzyl, 1-ethoxyethyl, methoxymethyl, 4-methoxyphenylmethyl, methoxyethoxymethyl, benzyloxymethyl, (β-trimethylsilylethoxy)methyl, tetrahydropyranyl, 2,2,2-trichloroethoxycarbonyl, t-butyl(diphenyl)silyl, trialkylsilyl, trichloromethoxycarbonyl, 2,2,2-trichloroethoxymethyl, alkansulfonyl, arylsulfonyl, and aryloxysulfonyl.

4. In a further embodiment of this process, said forming the product compound comprises reacting the first intermediate compound with a reducing agent under conditions effective to produce the product compound of formula (I).

5. In another embodiment of this process, X is a protecting group and said forming the product compound comprising reacting the first intermediate compound with a reducing agent followed by removal of the protecting group.

6. In another embodiment of this process, the first intermediate compound is provided as a substantially pure diastereomer having the structure:

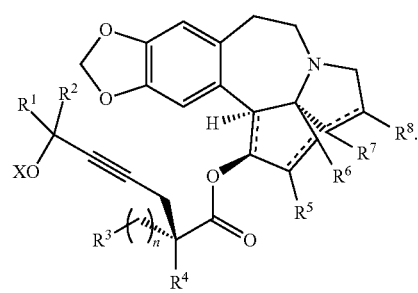

7. In yet another embodiment of this process, the process further includes providing a second intermediate compound of formula (III)
and

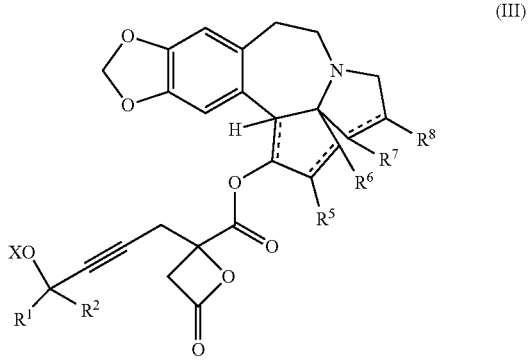

forming the first intermediate compound from the second intermediate compound.

8. In a further embodiment of this process, said forming the first intermediate compound comprises reacting the second intermediate compound with a base or under Lewis acid catalysis conditions effective to produce the first intermediate compound.

9. In another embodiment of this process, the second intermediate compound is provided as a substantially pure diastereomer having the structure:

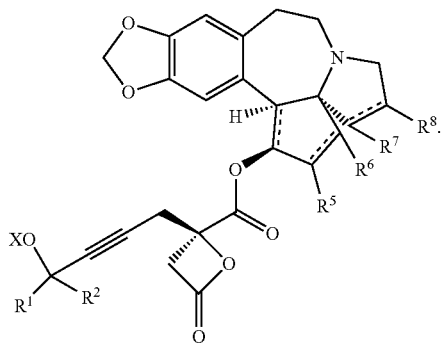

10. In another embodiment, the process as described above in embodiment 7 further includes providing a third intermediate compound of formula (IV)
and

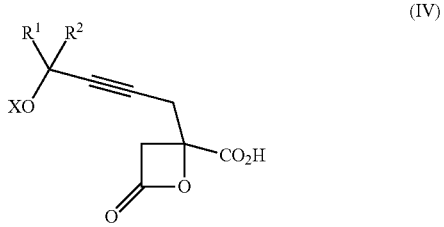

forming the second intermediate compound from the third intermediate compound.

11. Another embodiment relates to the process as described above, wherein said forming the second intermediate compound comprises reacting the third intermediate compound with cephalotaxine or a derivative thereof under conditions effective to produce the second intermediate compound.

12. Another embodiment relates to the process as described in embodiment 10 above, wherein the third intermediate compound is provided as a substantially pure diastereomer having the structure:

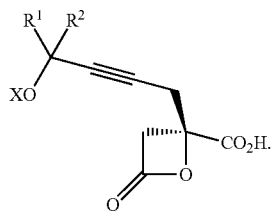

13. Another embodiment relates to the process as described in embodiment 10 above, further comprising: providing a fourth intermediate compound of formula (V)

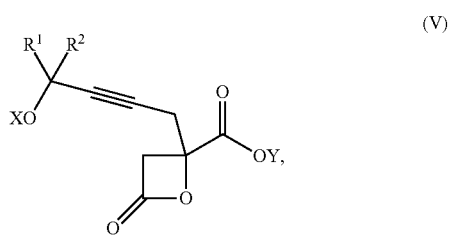

wherein Y is a protecting group, and
forming the third intermediate compound from the fourth intermediate compound.

14. Another embodiment relates to the process as described in the paragraph above, wherein X is an arylmethyl or heteroarylmethyl protecting group optionally substituted from 1 to 3 times with $C_1$-$C_6$ alkyl and Y is a trisubstituted silyl group 15. Another embodiment relates to the process as described in embodiment 13 above, wherein said forming the third intermediate compound comprises reacting the fourth intermediate compound with a protecting group removing agent under conditions effective to produce the third intermediate compound.

16. Another embodiment relates to the process as described in the paragraph above, wherein the protecting group removing agent is n-$Bu_4NF$, $NH_4F$, HF, HF.pyridine, CsF, $LiBF_4$, $BF_3$.$OEt_2$, or HCl.

17. Another embodiment relates to the process as described in embodiment 13 above, wherein the fourth intermediate compound is provided as a substantially pure diastereomer having the structure:

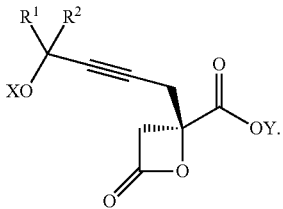

18. Another embodiment relates to the process as described in embodiment 13 above, further comprising:
providing a fifth intermediate compound of formula (VI)

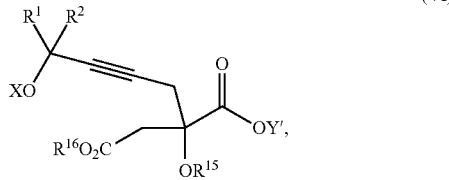
(VI)

wherein
Y' is hydrogen or a protecting group; and
$R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$, and
forming the fourth intermediate compound from the fifth intermediate compound.

19. Another embodiment relates to the process as described in the paragraph above, wherein said forming the fourth intermediate compound comprises reacting the fifth intermediate compound with a reagent that activates the intermediate for substitution under conditions effective to produce the fourth intermediate compound.

20. Another embodiment relates to the process as described in the paragraph above, wherein the reagent is selected from the group consisting of BOP—Cl, CDI, alkyl chloroformates, thionyl chloride, $T_3P$, aroyl chlorides, and disubstitutedphosphoryl halides.

21. Another embodiment relates to the process as described in embodiment 18 above, wherein the fifth intermediate compound is provided as a substantially pure diastereomer having the structure:

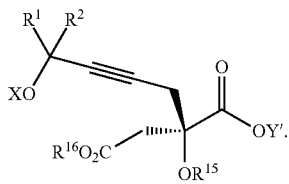

22. Another embodiment relates to the process as described in embodiment 13 above, further comprising:
providing a sixth intermediate compound of formula (VII)

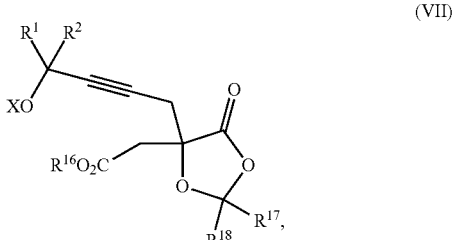
(VII)

wherein
$R^{17}$ is t-Bu, phenyl, naphthyl, $CF_3$, $CCl_3$, $CBr_3$, or $C_1$-$C_6$ alkoxy;
$R^{18}$ is H, Me, $CF_3$, $CCl_3$, $CBr_3$, or $C_1$-$C_6$ alkoxy;
or $R^{17}$ and $R^{18}$ combine with the carbon to which they are attached to form an internally bridged cycloalkyl, wherein the internally bridged cycloalkyl can be optionally substituted from 1 to 6 times with a substituent independently selected in each occurrence from $C_{1-6}$ alkyl and $C_{1-6}$ alkyl further substituted with —$SO_2N(C_{1-6}$ alkyl$)_2$; or
$R^{17}$ and $R^{18}$ are taken together to form a carbonyl, thiocarbonyl, sulfoxide, or sulfone, and forming the fifth intermediate compound from the sixth intermediate compound.

23. Another embodiment relates to the process as described in the paragraph above, wherein forming the fifth intermediate compound comprises reacting the sixth intermediate compound with a protecting group introducing agent under conditions effective to produce the fifth intermediate compound.

24. Another embodiment relates to the process as described in the paragraph above, wherein the protecting group introducing agent has the formula Y'—OH.

25. Another embodiment relates to the process as described in the paragraph above, wherein the protecting group introducing agent is TMS($CH_2$)$_2$OH.

26. Another embodiment relates to the process as described in embodiment 22 above, wherein the sixth intermediate compound is provided as a substantially pure diastereomer having the structure:

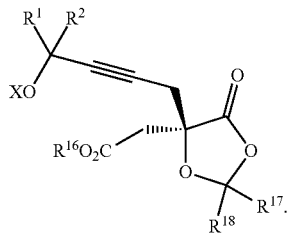

27. Another embodiment relates to the process as described in the paragraph above, wherein the substantially pure diastereomer is isolated by crystallization.

28. Another embodiment relates to the process as described in embodiment 22 above further comprising:
providing a seventh intermediate compound of formula (VIII)

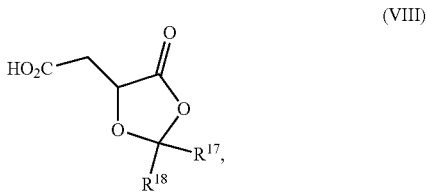
(VIII)

and
forming the sixth intermediate compound from the seventh intermediate compound.

29. Another embodiment relates to the process as described in the paragraph above, wherein said forming the sixth intermediate compound comprises reacting the seventh intermediate compound with a base and a compound of formula (IX):

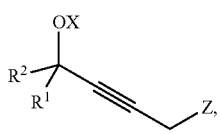

(IX)

wherein Z is selected from the group consisting of halogen, $OSO_2R^{19}$, $-OSO_3R^{19}$, $-OCOR^{19}$, $-OCO_2R^{19}$, $-OCSR^{19}$, $-OCS_2R^{19}$, $-OCN(R^{19})_2$, $-OPO(R^{19})_2$, $-OPO(OR^{19})_2$, and $-N(R^{19})_3^+$ and $R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^1$, under conditions effective to produce the sixth intermediate compound.

30. Another embodiment relates to the process as described in the paragraph above, wherein compound of formula (IX) has the structure:

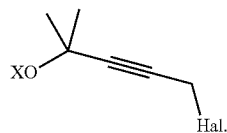

31. Another embodiment of the process as described in embodiment 1 further comprises:
providing a sixth intermediate compound of formula (VII)

(VII)

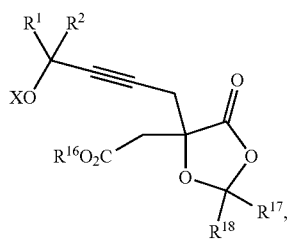

wherein
$R^{16}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, $-CO_2R^9$, $-CON(R^9)_2$, $-COSR^9$, $-COR^9$, $-C(OH)(R^9)_2$, $-C(OR^{10})(R^9)_2$, $-C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;
$R^{17}$ is t-Bu, phenyl, naphthyl, $CF_3$, $CCl_3$, $CBr_3$, or $C_1$-$C_6$ alkoxy;
$R^{18}$ is H, Me, $CF_3$, $CCl_3$, $CBr_3$, or $C_1$-$C_6$ alkoxy; or
$R^{17}$ and $R^{18}$ combine with the carbon to which they are attached to form an internally bridged cycloalkyl, wherein the internally bridged cycloalkyl can be optionally substituted from 1 to 6 times with a substituent independently selected in each occurrence from $C_{1-6}$ alkyl and $C_{1-6}$ alkyl further substituted with $-SO_2N(C_{1-6}$ alkyl$)_2$; or $R^{17}$ and $R^{18}$ are taken together to form a carbonyl, thiocarbonyl, sulfoxide, or sulfone,
and
forming the first intermediate compound from the sixth intermediate compound.

32. Another embodiment relates to the process as described in the paragraph above, wherein said forming the first intermediate compound comprises reacting the sixth intermediate compound with cephalotaxine or a derivative thereof under conditions effective to produce the first intermediate compound.

33. Another embodiment relates to the process as described in embodiment 31, wherein the sixth intermediate compound is provided as a substantially pure diastereomer having the structure:

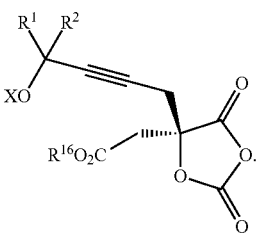

34. Another embodiment relates to the process as described in embodiment 31, wherein the sixth intermediate compound is provided as a substantially pure diastereomer having the structure:

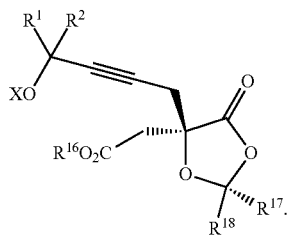

35. Another embodiment relates to the process as described in embodiment 31, further comprising:
providing a fifth intermediate compound of formula (VI)

(VI)

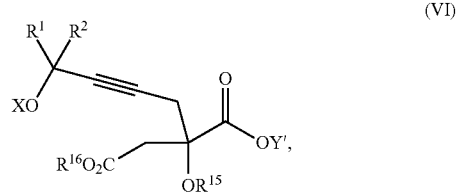

wherein Y' is hydrogen or a protecting group; and
$R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, $-CO_2R^9$, $-CON(R^9)_2$, $-COSR^9$, $-COR^9$, $-C(OH)(R^9)_2$, $-C(OR^{10})(R^9)_2$, $-C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$, and forming the sixth intermediate compound from the fifth intermediate compound.

36. Another embodiment relates to the process as described in the paragraph above, wherein forming the sixth intermediate compound comprises reacting the fifth intermediate compound with trichloromethyl chloroformate, bis (trichloromethyl) carbonate, phosgene, sulfuryl chloride, carbonyl diimidazole, thiocarbonyl diimidazole, sulfuryl diimidazole or thiourea under conditions effective to produce the sixth intermediate compound.

37. Another embodiment relates to the process as described in the paragraph above, further comprising reacting the fifth intermediate compound with a protecting group removing agent prior to said reacting step.

38. Another embodiment relates to the process as described in the paragraph above, wherein the protecting group removing agent is n-$Bu_4NF$, $NH_4F$, HF, HF.pyridine, CsF, $LiBF_4$, $BF_3.OEt_2$, or HCl.

39. Another embodiment relates to the process as described in embodiment 35, wherein the fifth intermediate compound is provided as a substantially pure diastereomer having the structure:

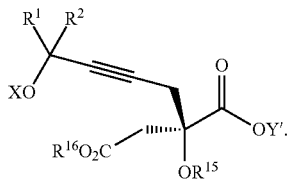

40. Another embodiment relates to the process as described in embodiment 31, wherein the compound of formula (I) has the following structure:

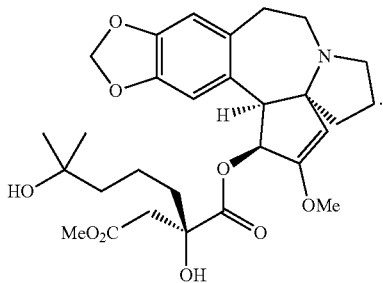 [SMILES: COC(=O)C[C@](O)(CCCC(C)(C)O)C(=O)O[C@@H]1C(OC)=C[C@]23CCCN2CCc2cc4c(cc2[C@H]13)OCO4]

41. In another embodiment of this process, the compound of formula (I) has the following structure:

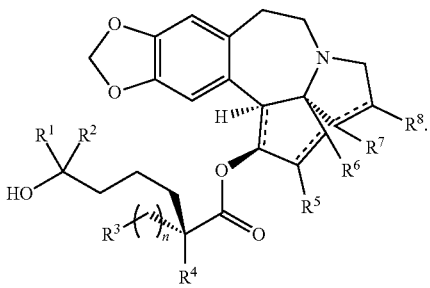

42. Another embodiment relates to the process as described in the paragraph above, wherein the compound of formula (I) has the following structure:

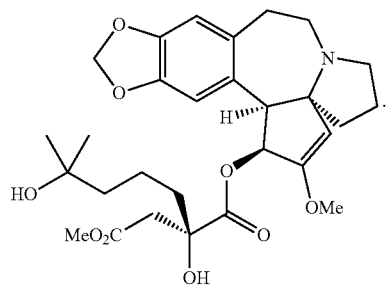 [SMILES: COC(=O)C[C@](O)(CCCC(C)(C)O)C(=O)O[C@@H]1C(OC)=C[C@]23CCCN2CCc2cc4c(cc2[C@H]13)OCO4]

43. The present invention relates to a compound of formula (II):

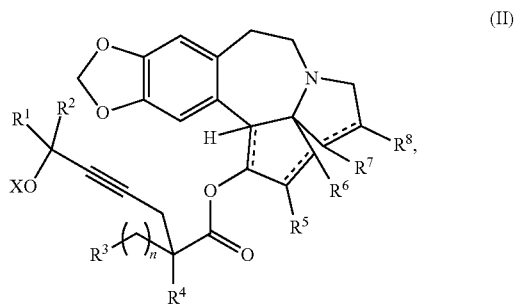

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

X is hydrogen or a protecting group;

each ⸺ independently designates a single or double bond; and n is an integer from 0 to 9;

m is an integer from 0 to 2, or a pharmaceutically acceptable salt thereof, or a solvate thereof.

44. One embodiment relates to the compound as described in the paragraph above, wherein the compound is a substantially pure diastereomer having the structure:

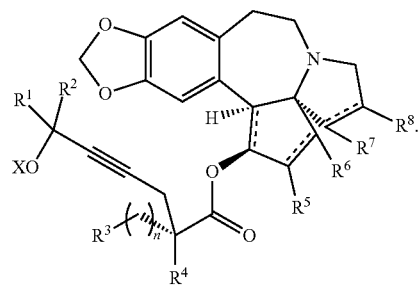

45. Another embodiment relates to the compound as described in embodiment 43 which has the formula (IIa):

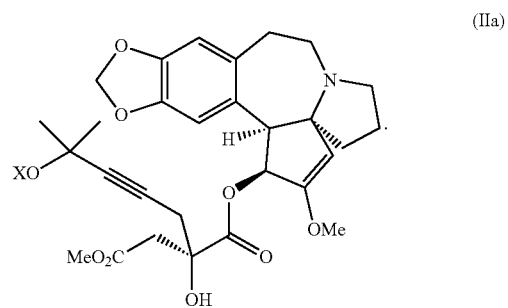

(IIa)

46. The present invention relates to a compound of formula (III):

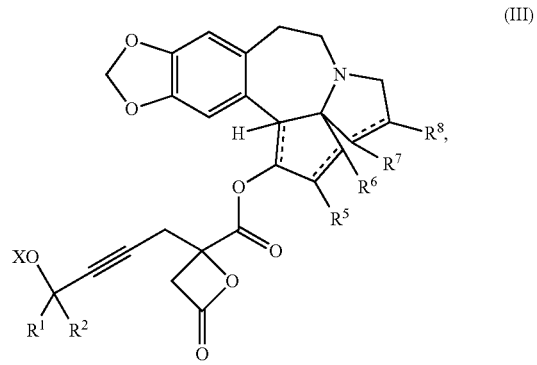

(III)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, C$_3$-C$_7$ cycloalkyl, C$_4$-C$_7$ cycloalkylalkyl, heterocycle, aryl, heteroaryl, —SO$_2$R$^{10}$, and —CO$_2$R$^{10}$; or R$^7$ and R$^8$ are taken together to form an optionally substituted 5- to 7-membered ring having 0-2 heteroatoms independently selected from nitrogen, oxygen, and sulfur;

each R$^{10}$ is independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or two R$^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with R$^{11}$;

R$^{11}$ is independently selected at each occurrence from a substituent in the group consisting of halogen, —NO$_2$, —OR$^{12}$, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, wherein each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted with 1 to 3 substituents independently selected at each occurrence from the group consisting of C$_1$-C$_4$ alkyl, C$_1$-C$_4$ alkoxy, halogen, Ar, —CN, and —NR$^{12}$R$^{13}$;

R$^{12}$ and R$^{13}$ are each independently hydrogen, C$_1$-C$_4$ alkyl, C$_1$-C$_4$ haloalkyl, C$_1$-C$_4$ alkoxyalkyl, C$_3$-C$_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, C$_1$-C$_4$ alkyl, C$_1$-C$_4$ haloalkyl, and C$_1$-C$_4$ alkoxy; or R$^{12}$ and R$^{13}$ are taken together with the nitrogen to which they are attached to form a piperidine, pyrrolidine, piperazine, N-methylpiperazine, morpholine, or thiomorpholine ring;

R$^{14}$ is C$_1$-C$_4$ alkyl, C$_1$-C$_4$ haloalkyl, or phenyl;

X is hydrogen or a protecting group;

m is an integer from 0 to 2; and each ═══ independently designates a single or double bond, or a pharmaceutically acceptable salt thereof, or a solvate thereof.

47. One embodiment relates to the compound as described in the paragraph above, wherein the compound is a substantially pure diastereomer having the structure:

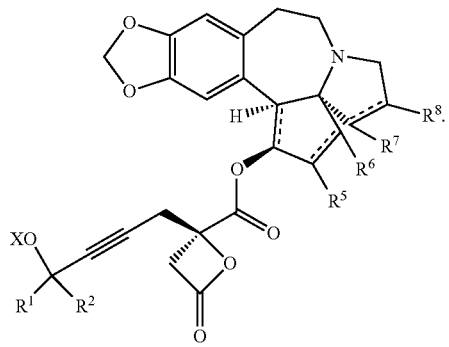

48. Another embodiment relates to the compound as described in embodiment 46 which has the formula (IIIa):

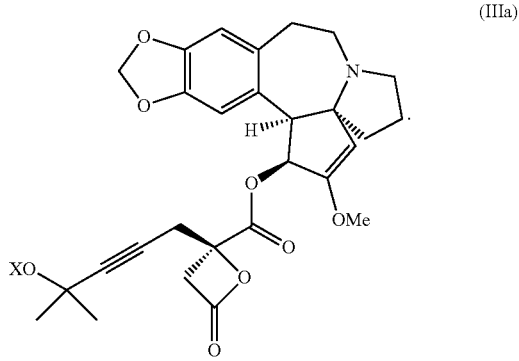

(IIIa)

49. The present invention relates to a compound of formula (IV):

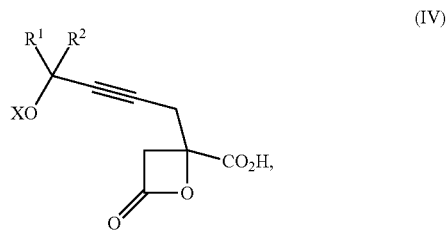

(IV)

wherein

R$^1$ and R$^2$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or R$^1$ and R$^2$ are taken together to form a carbonyl, thiocarbonyl, sulfoxide, or sulfone;

R$^{11}$ is independently selected at each occurrence from a substituent in the group consisting of halogen, —NO$_2$, —OR, —N$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, wherein each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted with 1 to 3 substituents independently selected at each occurrence from the group consisting of C$_1$-C$_4$ alkyl, C$_1$-C$_4$ alkoxy, halogen, Ar, —CN, and —NR$^{12}$R$^{13}$;

R$^{12}$ and R$^{13}$ are each independently hydrogen, C$_1$-C$_4$ alkyl, C$_1$-C$_4$ haloalkyl, C$_1$-C$_4$ alkoxyalkyl, C$_3$-C$_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, C$_1$-C$_4$ alkyl, C$_1$-C$_4$ haloalkyl, and C$_1$-C$_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

m is an integer from 0 to 2; and

X is hydrogen or a protecting group, or a pharmaceutically acceptable salt thereof, or a solvate thereof.

50. One embodiment relates to the compound as described in the paragraph above, wherein the compound is a substantially pure diastereomer having the structure:

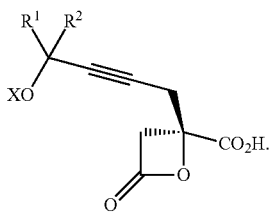

51. Another embodiment relates to the compound as described in embodiment 49 which has the formula (IVa):

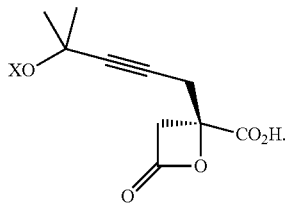

(IVa)

52. The present invention relates to a compound of formula (V):

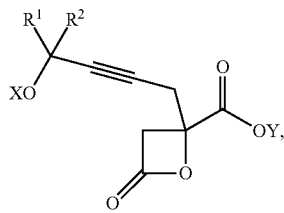

(V)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

m is an integer from 0 to 2; and

X and Y are each independently hydrogen or a protecting group, or a pharmaceutically acceptable salt thereof, or a solvate thereof.

53. One embodiment relates to the compound as described in the paragraph above, wherein the compound is a substantially pure diastereomer having the structure:

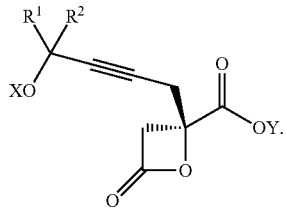

54. Another embodiment relates to the compound as described in embodiment 52 which has the formula (Va):

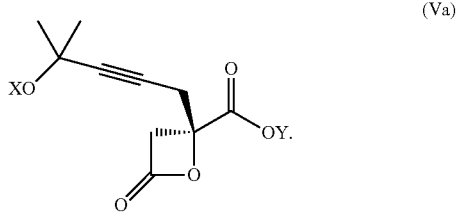

(Va)

55. The present invention relates to a compound of formula (VI):

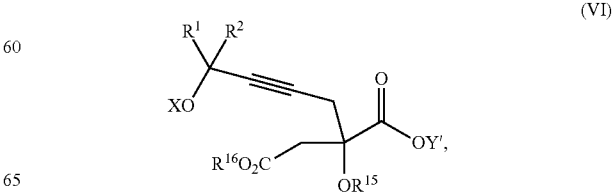

(VI)

wherein

R$^1$ and R$^2$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or R$^1$ and R$^2$ are taken together to form a carbonyl, thiocarbonyl, sulfoxide, or sulfone;

R$^9$ is hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, or heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$;

each R$^{10}$ is independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or two R$^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with R$^{11}$;

R$^{11}$ is independently selected at each occurrence from a substituent in the group consisting of halogen, —NO$_2$, —OR, —NR$^{12}$R$^{13}$, —NR$^{12}$C(O)$_2$R$^{13}$, —NR$^{12}$C(O)NR$^{13}$, —S(O)$_m$R$^{13}$, —CN, —C(O)R$^{13}$, —C(O)NR$^{12}$R$^{13}$, C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl, wherein each of C$_1$-C$_6$ alkyl, C$_2$-C$_6$ alkenyl, C$_2$-C$_6$ alkynyl, C$_3$-C$_6$ cycloalkyl, and C$_4$-C$_7$ cycloalkylalkyl is optionally substituted with 1 to 3 substituents independently selected at each occurrence from the group consisting of C$_1$-C$_4$ alkyl, C$_1$-C$_4$ alkoxy, halogen, Ar, —CN, and —NR$^{12}$R$^{13}$;

R$^{12}$ and R$^{13}$ are each independently hydrogen, C$_1$-C$_4$ alkyl, C$_1$-C$_4$ haloalkyl, C$_1$-C$_4$ alkoxyalkyl, C$_3$-C$_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, C$_1$-C$_4$ alkyl, C$_1$-C$_4$ haloalkyl, and C$_1$-C$_4$ alkoxy; or R$^{12}$ and R$^{13}$ are taken together with the nitrogen to which they are attached to form a piperidine, pyrrolidine, piperazine, N-methylpiperazine, morpholine, or thiomorpholine ring;

R$^{14}$ is C$_1$-C$_4$ alkyl, C$_1$-C$_4$ haloalkyl, or phenyl;

R$^{15}$ and R$^{16}$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^{10}$$_2$)(R$^9$)$_2$, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$;

m is an integer from 0 to 2; and

X and Y' are each independently hydrogen or a protecting group, or a pharmaceutically acceptable salt thereof, or a solvate thereof.

56. One embodiment relates to the compound as described in the paragraph above, wherein the compound is a substantially pure diastereomer having the structure:

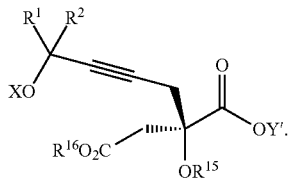

57. Another embodiment relates to the compound as described in embodiment 55 which has the formula (VIa):

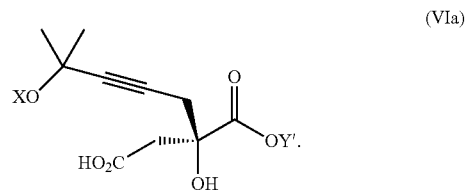

(VIa)

58. The present invention relates to a compound of formula (VII):

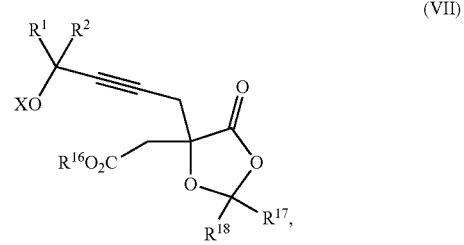

(VII)

wherein

R$^1$ and R$^2$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$; or R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or R$^1$ and R$^2$ are taken together to form a carbonyl, thiocarbonyl, sulfoxide, or sulfone;

R$^9$ is hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, or heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$;

each R$^{10}$ is independently selected from the group consisting of hydrogen, C$_1$-C$_6$ alkyl, C$_2$-C$_6$ alkenyl, C$_2$-C$_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, $-NO_2$, $-OR^{12}$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{16}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, $-CO_2R^9$, $-CON(R^9)_2$, $-COSR^9$, $-COR^9$, $-C(OH)(R^9)_2$, $-C(OR^{10})(R^9)_2$, $-C(NR^{10}{}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{17}$ is t-Bu, phenyl, naphthyl, $CF_3$, $CCl_3$, $CBr_3$, or $C_1$-$C_6$ alkoxy;

$R^{18}$ is H, Me, $CF_3$, $CCl_3$, $CBr_3$, or $C_1$-$C_6$ alkoxy; or $R^{17}$ and $R^{18}$ combine with the carbon to which they are attached to form an internally bridged cycloalkyl, wherein internally bridged cycloalkyl can be optionally substituted from 1 to 6 times with a substituent independently selected in each occurrence from $C_{1-6}$ alkyl and $C_{1-6}$ alkyl further substituted with $-SO_2N(C_{1-6}$ alkyl$)_2$; or $R^{17}$ and $R^{18}$ are taken together to form a carbonyl, thiocarbonyl, sulfoxide, or sulfone;

m is an integer from 0 to 2; and

X is hydrogen or a protecting group, or a pharmaceutically acceptable salt thereof, or a solvate thereof.

59. Another embodiment relates to the compound as described in the paragraph above, wherein the compound is a substantially pure diastereomer having the structure:

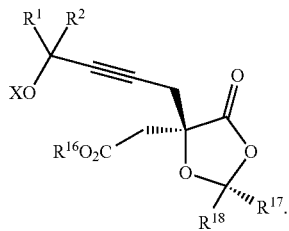

60. Another embodiment relates to the compound is described in embodiment 58 which has the formula (VIIa):

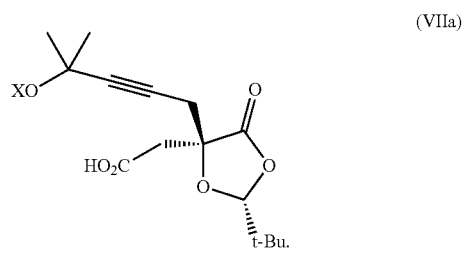

(VIIa)

61. Another embodiment relates to the compound as described in embodiment 58 which has the formula (VIIb):

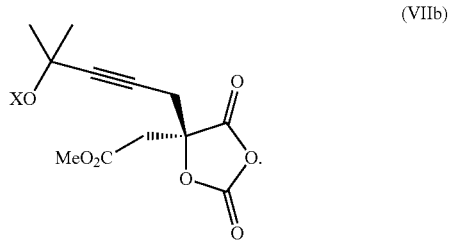

(VIIb)

62. The present invention relates to a process for preparation of a product compound of formula (IX):

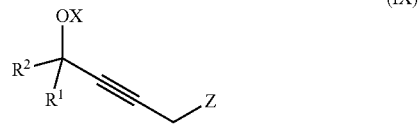

(IX)

wherein

X is hydrogen or a protecting group;

Z is selected from the group consisting of halogen, $-OSO_2R^{19}$, $-OSO_3R^{19}$, $-OCOR^{19}$, $-OCO_2R^{19}$, $-OCSR^{19}$, $-OCS_2R^{19}$, $-OCN(R^{19})_2$, $-OPO(R^{19})_2$, $-OPO(OR^{19})_2$, and $-N(R^{19})_3{}^+$;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, $-NO_2$, $-OR^{12}$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; and m is an integer from 0 to 2, or a pharmaceutically acceptable salt thereof, or a solvate thereof;

said method comprising:

providing an eighth intermediate compound of formula (X):

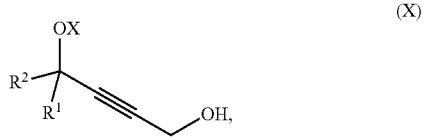

and forming the product compound of formula (IX) from the eighth intermediate compound.

63. Another embodiment relates to the process as described in the paragraph above, wherein said forming the product compound comprises:

subjecting the eighth intermediate compound to halogenation/deoxygenation conditions.

64. The process as described in embodiment 62 further comprising:

providing a ninth intermediate compound of formula (XI)

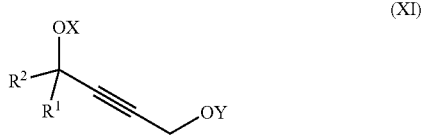

wherein Y is a protecting group, and forming the eighth intermediate compound of formula (X) from the ninth intermediate compound of formula (XI).

65. Another embodiment relates to the process as described in the paragraph above, wherein said forming the eighth intermediate compound comprises reacting the ninth intermediate compound with a protecting group removing agent.

66. Another embodiment relates to the process as described in embodiment 64, wherein the protecting group removing agent is n-$Bu_4NF$, $NH_4F$, HF, HF.pyridine, CsF, $LiBF_4$, $BF_3.OEt_2$, or HCl.

67. Another embodiment relates to the process as described in embodiment 64, wherein Y is a trisubstituted silyl group.

68. The process as described in embodiment 64 further comprising:

providing a tenth intermediate compound of formula (XII)

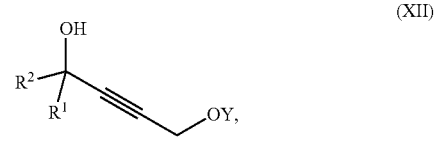

and forming the ninth intermediate compound of formula (XI) from the tenth intermediate compound of formula (XII).

69. Another embodiment relates to the process as described in the paragraph above, wherein said forming the ninth intermediate compound comprises subjecting the tenth intermediate compound to deprotonation in the presence of a base and a compound comprising X.

70. Another embodiment relates to the process as described in embodiment 62, wherein Z is a halogen.

71. Another embodiment relates to the process as described in embodiment 62, wherein X is an arylmethyl or heteroarylmethyl protecting group, optionally substituted from 1 to 3 times with $C_1$-$C_6$ alkyl.

72. Another embodiment relates to the process as described in embodiment 62, wherein $R^1$ and $R^2$ are each $C_1$-$C_6$ alkyl.

73. The present invention relates to a compound of formula (IX):

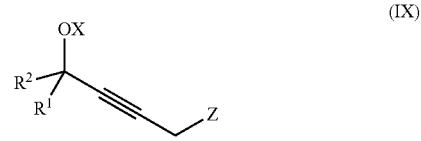

wherein

X is hydrogen or a protecting group;

Z is selected from the group consisting of halogen, $-OSO_2R^{19}$, $-OSO_3R^{19}$, $-OCOR^{19}$, $-OCO_2R^{19}$, $-OCSR^{19}$, $-OCS_2R^{19}$, $-OCN(R^{19})_2$, $-OPO(R^{19})_2$, $-OPO(OR^{19})_2$, and $-N(R^{19})_3^+$;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, $-NO_2$, $-OR^{12}$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl; $R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; and m is an integer from 0 to 2, or a pharmaceutically acceptable salt thereof, or a solvate thereof.

74. Another embodiment relates to the compound as described in the paragraph above, wherein Z is a halogen.

75. Another embodiment relates to the compound as described in embodiment 73, wherein X is an arylmethyl or heteroarylmethyl protecting group, optionally substituted from 1 to 3 times with $C_1$-$C_6$ alkyl.

76. Another embodiment relates to the compound as described in embodiment 73, wherein $R^1$ and $R^2$ are each $C_1$-$C_6$ alkyl.

77. The present invention relates to a compound of formula (XIII):

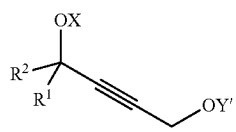

(XIII)

wherein
X is hydrogen or a protecting group;
Y' is hydrogen or a protecting group;
$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, $-NO_2$, $-OR^{12}$, $-NR^{12}R^{13}$, $-NR^{12}C(O)_2R^{13}$, $-NR^{12}C(O)NR^{12}R^{13}$, $-S(O)_mR^{13}$, $-CN$, $-C(O)R^{13}$, $-C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, $-CN$, and $-NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, $-C(O)R^{14}$, phenyl, or benzyl, wherein phenyl or benzyl is optionally substituted with 1 to 3 substituents independently selected at each occurrence from the group consisting of halogen, $-CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl; and
m is an integer from 0 to 2, or a pharmaceutically acceptable salt thereof, or a solvate thereof.

78. Another embodiment relates to the compound as described in the paragraph above, wherein X is an arylmethyl or heteroarylmethyl protecting group, optionally substituted from 1 to 3 times with $C_1$-$C_6$ alkyl.

79. Another embodiment relates to the compound as described in embodiment 77, wherein Y is a trisubstituted silyl group.

80. Another embodiment relates to the compound as described in embodiment 77, wherein $R^1$ and $R^2$ are each $C_1$-$C_6$ alkyl.

81. The present invention relates to a process for preparation of a product compound of formula (XIV):

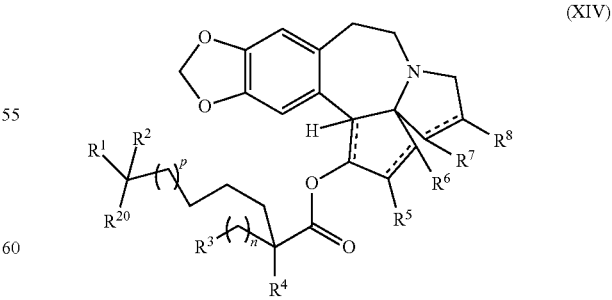

(XIV)

wherein
$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with substituents as defined below in $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^1$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each ═ independently designates a single or double bond; and n is an integer from 0 to 9;

m is an integer from 0 to 2;

p is an integer from 0 to 3, or a pharmaceutically acceptable salt thereof, or a solvate thereof, said process comprising:

providing an eleventh intermediate compound having the structure:

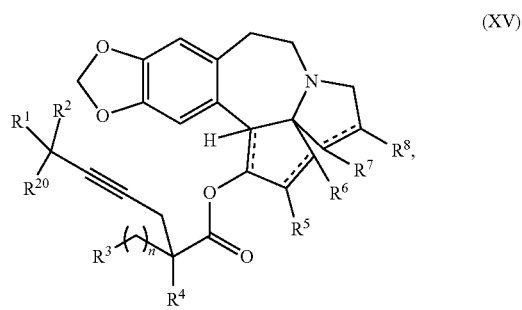

(XV)

and forming the product compound of formula (XIV) from the eleventh intermediate compound.

82. Another embodiment relates to the process as described in the paragraph above, wherein said forming the product compound comprises reacting the eleventh intermediate compound with a reducing agent under conditions effective to produce the product compound of formula (XIV).

83. Another embodiment relates to the process as described in embodiment 81, wherein the eleventh intermediate compound is provided as a substantially pure diastereomer having the structure:

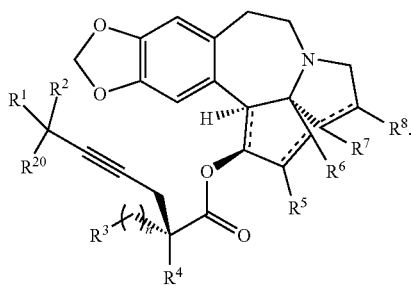

84. Another embodiment relates to the process as described in embodiment 81 further comprising:
providing a twelfth intermediate compound of formula (XVI)

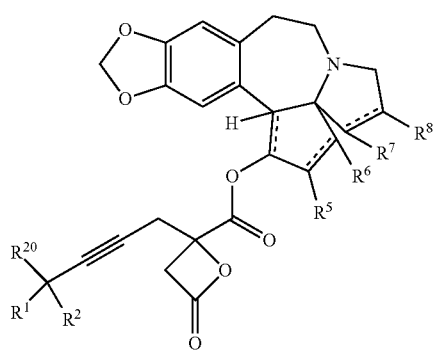
(XVI)

and forming the eleventh intermediate compound from the twelfth intermediate compound.

85. Another embodiment relates to the process as described in the paragraph above, wherein said forming the eleventh intermediate compound comprises reacting the twelfth intermediate compound with a base or under Lewis acid catalysis conditions effective to produce the eleventh intermediate compound.

86. Another embodiment relates to the process as described in embodiment 84, wherein the twelfth intermediate compound is provided as a substantially pure diastereomer having the structure:

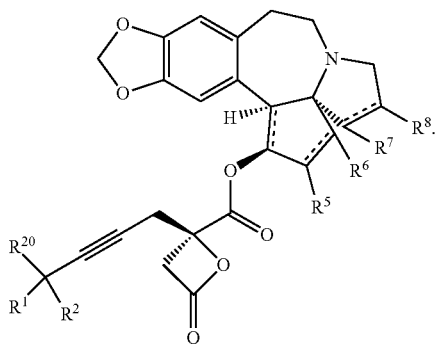

87. Another embodiment relates to the process as described in embodiment 84 further comprising:
providing a thirteenth intermediate compound of formula (XVII)

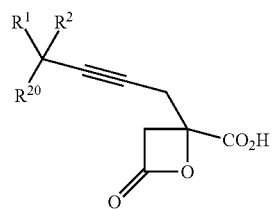
(XVII)

and forming the twelfth intermediate compound from the thirteenth intermediate compound.

88. Another embodiment relates to the process as described in the paragraph above, wherein said forming the twelfth intermediate compound comprises reacting the thirteenth intermediate compound with cephalotaxine or a derivative thereof under conditions effective to produce the twelfth intermediate compound.

89. Another embodiment relates to the process as described in embodiment 87, wherein the thirteenth intermediate compound is provided as a substantially pure diastereomer having the structure:

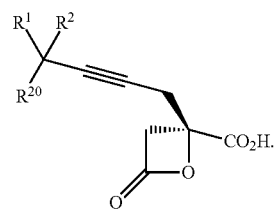

90. Another embodiment relates to the process as described in embodiment 87 further comprising:
providing a fourteenth intermediate compound of formula (XVIII)

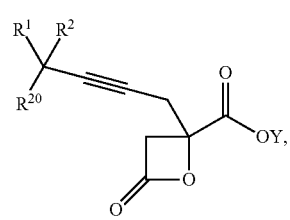
(XVIII)

wherein Y is a protecting group, and forming the thirteenth intermediate compound from the fourteenth intermediate compound.

91. Another embodiment relates to the process as described in the paragraph above, wherein said forming the thirteenth intermediate compound comprises reacting the fourteenth intermediate compound with a protecting group removing agent under conditions effective to produce the thirteenth intermediate compound.

92. Another embodiment relates to the process as described in the paragraph above, wherein the protecting group removing agent is n-Bu$_4$NF, NH$_4$F, HF, HF.pyridine, CsF, LiBF$_4$, BF$_3$.OEt$_2$, or HCl.

93. Another embodiment relates to the process as described in embodiment 90, wherein the fourteenth intermediate compound is provided as a substantially pure diastereomer having the structure:

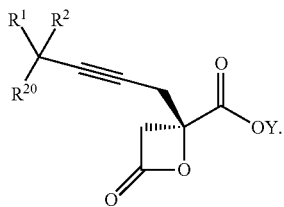

94. Another embodiment relates to the process as described in embodiment 90 further comprising:
providing a fifteenth intermediate compound of formula (XIX)

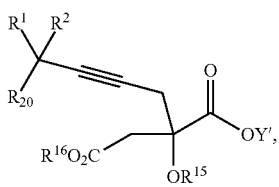

(XIX)

wherein

Y' is hydrogen or a protecting group; and $R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$, and forming the fourteenth intermediate compound from the fifteenth intermediate compound.

95. Another embodiment relates to the process as described in the paragraph above, wherein said forming the fourteenth intermediate compound comprises reacting the fifteenth intermediate compound with a reagent that activates the intermediate for substitution under conditions effective to produce the fourteenth intermediate compound.

96. Another embodiment relates to the process as described in the paragraph above, wherein the reagent is selected from the group consisting of BOP—Cl, CDI, alkyl chloroformates, thionyl chloride, $T_3P$, aroyl chlorides, and disubstitutedphosphoryl halides.

97. Another embodiment relates to the process as described in embodiment 94, wherein the fifteenth intermediate compound is provided as a substantially pure diastereomer having the structure:

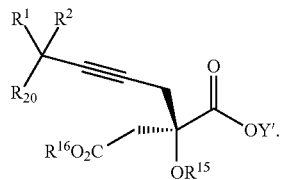

98. Another embodiment relates to the process as described in embodiment 94 further comprising:
providing a sixteenth intermediate compound of formula (XX)

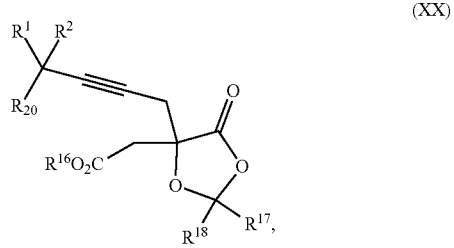

wherein $R^{17}$ is t-Bu, phenyl, naphthyl, $CF_3$, $CCl_3$, $CBr_3$, or $C_1$-$C_6$ alkoxy;

$R^{18}$ is H, Me, $CF_3$, $CCl_3$, $CBr_3$, or $C_1$-$C_6$ alkoxy;

or $R^{17}$ and $R^{18}$ combine with the carbon to which they are attached to form an internally bridged cycloalkyl, wherein internally bridged cycloalkyl can be optionally substituted from 1 to 6 times with a substituent independently selected in each occurrence from $C_{1-6}$ alkyl and $C_{1-6}$ alkyl further substituted with —$SO_2N(C_{1-6}$ alkyl$)_2$; or $R^{17}$ and $R^{18}$ are taken together to form a carbonyl, thiocarbonyl, sulfoxide, or sulfone, and forming the fifteenth intermediate compound from the sixteenth intermediate compound.

99. Another embodiment relates to the process as described in the paragraph above, wherein forming the fifteenth intermediate compound comprises reacting the sixteenth intermediate compound with a protecting group introducing agent under conditions effective to produce the fifteenth intermediate compound.

100. Another embodiment relates to the process as described in the paragraph above, wherein the protecting group introducing agent has the formula Y'—OH.

101 Another embodiment relates to the process as described in the paragraph above, wherein the protecting group introducing agent is TMS(CH$_2$)$_2$OH.

102. The process as described in embodiment 98, wherein the sixteenth intermediate compound is provided as a substantially pure diastereomer having the structure:

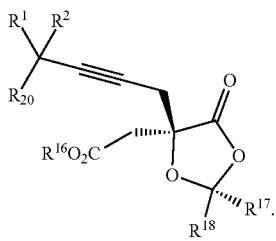

103. Another embodiment relates to the process as described in the paragraph above, wherein the substantially pure diastereomer is isolated by crystallization.

104. Another embodiment relates to the process as described in embodiment 98 further comprising:
providing a seventh intermediate compound of formula (VIII)

(VIII)

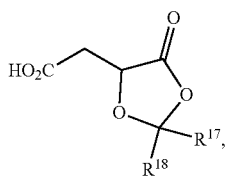

and
forming the sixteenth intermediate compound from the seventh intermediate compound.

105. Another embodiment relates to the process as described in the paragraph above, wherein said forming the sixteenth intermediate compound comprises reacting the seventh intermediate compound with a base and then with a compound of formula (XXI):

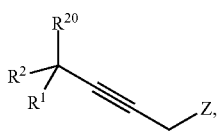

(XXI)

wherein Z is selected from the group consisting of halogen, —OSO$_2$R$^{19}$, —OSO$_3$R$^{19}$, —OCOR$^{19}$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, and —N(R$^{19}$)$_3^+$ and R$^{19}$ is selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$, under conditions effective to produce the sixth intermediate compound.

106. Another embodiment relates to the process as described in the paragraph above, wherein compound of formula (XXI) has the structure:

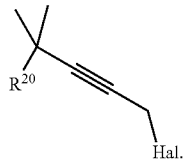

107. Another embodiment relates to the process as described in embodiment 81 further comprising:
providing a seventeenth intermediate compound of formula (XXII)

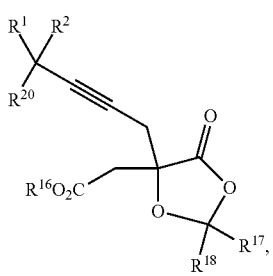

(XXII)

wherein
R$^{16}$ is selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^2$)(R$^9$)$_2$, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$;

R$^{17}$ is t-Bu, phenyl, naphthyl, CF$_3$, CCl$_3$, CBr$_3$, or C$_1$-C$_6$ alkoxy;

R$^{18}$ is H, Me, CF$_3$, CCl$_3$, CBr$_3$, or C$_1$-C$_6$ alkoxy; or

R$^{17}$ and R$^{18}$ combine with the carbon to which they are attached to form an internally bridged cycloalkyl, wherein the internally bridged cycloalkyl can be optionally substituted from 1 to 6 times with a substituent independently selected in each occurrence from C$_{1-6}$ alkyl and C$_{1-6}$ alkyl further substituted with —SO$_2$N(C$_{1-6}$ alkyl)$_2$; or R$^{17}$ and R$^{18}$ are taken together to form a carbonyl, thiocarbonyl, sulfoxide, or sulfone,
and
forming the eleventh intermediate compound from the seventeenth intermediate compound.

108. Another embodiment relates to the process as described in the paragraph above, wherein said forming the eleventh intermediate compound comprises reacting the seventeenth intermediate compound with cephalotaxine or a derivative thereof under conditions effective to produce the eleventh intermediate compound.

109. Another embodiment relates to the process as described in embodiment 107, wherein the seventeenth intermediate compound is provided as a substantially pure diastereomer having the structure:

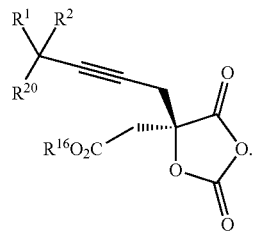

110. Another embodiment relates to the process as described in embodiment 107, wherein the seventeenth intermediate compound is provided as a substantially pure diastereomer having the structure:

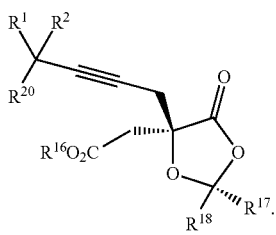

111. Another embodiment relates to the process as described in embodiment 107 further comprising:
providing an eighteenth intermediate compound of formula (XXIII)

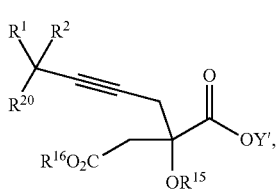

(XXIII)

wherein Y' is hydrogen or a protecting group; and
R$^{15}$ and R$^{16}$ are each independently selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^{10}$$_2$)(R$^9$)$_2$, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$, and forming the seventeenth intermediate compound from the eighteenth intermediate compound.

112. Another embodiment relates to the process as described in the paragraph above, wherein forming the seventeenth intermediate compound comprises reacting the eighteenth intermediate compound with trichloromethyl chloroformate, bis(trichloromethyl) carbonate, phosgene, sulfuryl chloride, carbonyl diimidazole, thiocarbonyl diimidazole, sulfuryl diimidazole or thiourea under conditions effective to produce the seventeenth intermediate compound.

113. Another embodiment relates to the process as described in the paragraph above, further comprising reacting the eighteenth intermediate compound with a protecting group removing agent prior to said reacting step.

114. Another embodiment relates to the process as described in the paragraph above, wherein the protecting group removing agent is n-Bu$_4$NF, NH$_4$F, HF, HF.pyridine, CsF, LiBF$_4$, BF$_3$.OEt$_2$, or HCl.

115. Another embodiment relates to the process as described in embodiment 111, wherein the eighteenth intermediate compound is provided as a substantially pure diastereomer having the structure:

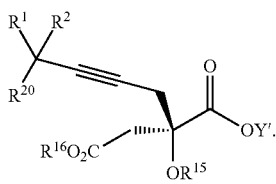

116. Another embodiment relates to the process as described in embodiment 107, wherein the compound of formula (XIV) has the following structure:

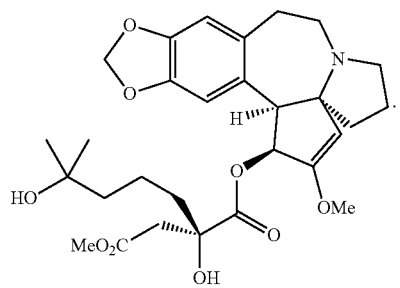 [SMILES: COC(=O)C[C@](O)(CCCC(C)(C)O)C(=O)O[C@@H]1C(OC)=C[C@]23CCCN2CCc2cc4c(cc2[C@H]13)OCO4]

117. Another embodiment relates to the process as described in embodiment 81, wherein the compound of formula (XIV) has the following structure:

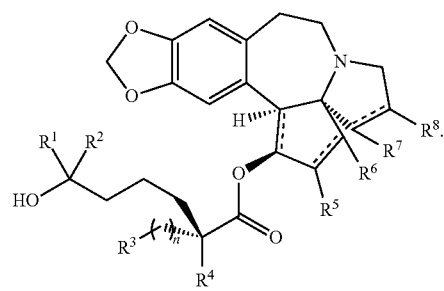

118. Another embodiment relates to the process as described in the paragraph above, wherein the compound of formula (I) has the following structure:

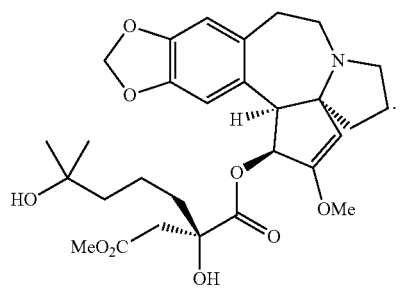 [SMILES: COC(=O)C[C@](O)(CCCC(C)(C)O)C(=O)O[C@@H]1C(OC)=C[C@]23CCCN2CCc2cc4c(cc2[C@H]13)OCO4]

119. The present invention relates to a compound of formula (XV):

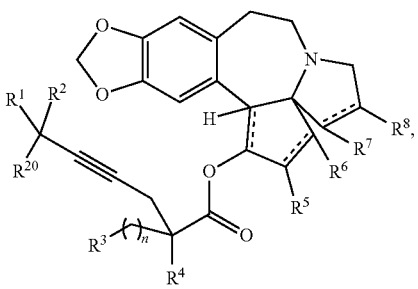

(XV)

wherein
R$^1$ and R$^2$ are each independently selected from the group consisting of hydrogen, C$_1$-C$_6$ alkyl, C$_2$-C$_6$ alkenyl, C$_2$-C$_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and $NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each ⚌ independently designates a single or double bond;
n is an integer from 0 to 9; and
m is an integer from 0 to 2,
or a pharmaceutically acceptable salt thereof, or a solvate thereof.

120. Another embodiment relates to the compound as described in the paragraph above, wherein the compound is a substantially pure diastereomer having the structure:

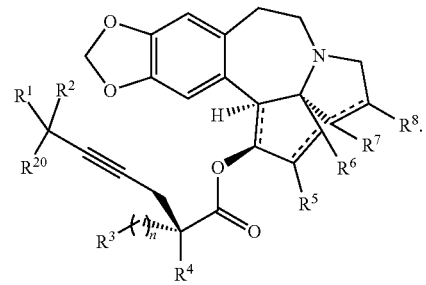

121. The present invention relates to a compound of formula (XVI):

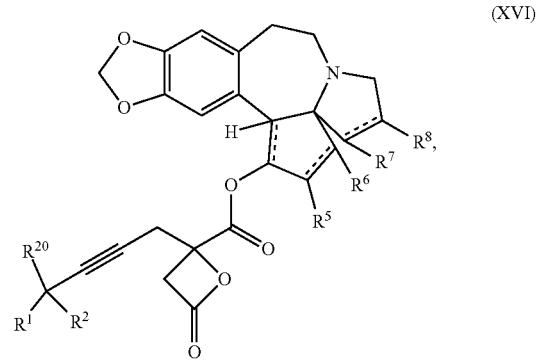

(XVI)

wherein
$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^5$ is hydrogen, —$OR^{10}$, or =O;

$R^6$ is hydrogen, —$OR^{10}$, —$OCO_2R^{10}$, —$OCOR^{10}$, —$OCOSR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —$CN$, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —$CN$, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —$CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —$CN$, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

m is an integer from 0 to 2; and each ═══ independently designates a single or double bond, or a pharmaceutically acceptable salt thereof, or a solvate thereof.

122. Another embodiment relates to the compound as described in the paragraph above, wherein the compound is a substantially pure diastereomer having the structure:

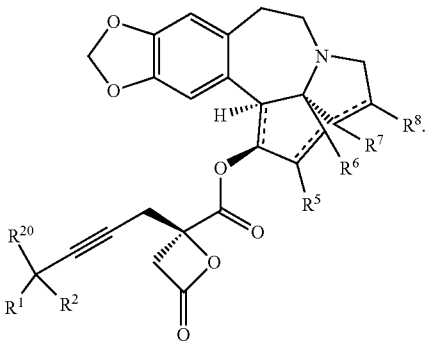

123. The present invention relates to a compound of formula (XVII):

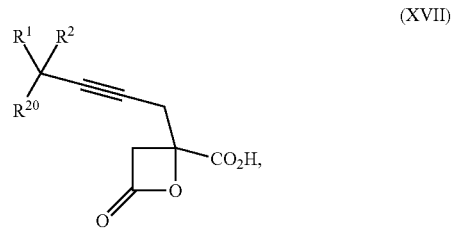

(XVII)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{12}R^{13}$, —$S(O)_mR^{13}$, —$CN$, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —$CN$, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —$CN$, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring; and $R^{14}$ is $C_1$-$C_4$ alkyl, $C_1$-$C_4$ haloalkyl, or phenyl;

$R^{20}$ is hydrogen, halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

m is an integer from 0 to 2;

or a pharmaceutically acceptable salt thereof, or a solvate thereof.

124. Another embodiment relates to the compound as described in the paragraph above, wherein the compound is a substantially pure diastereomer having the structure:

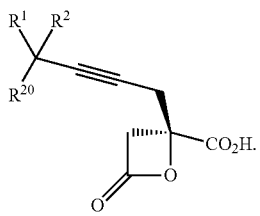

125. The present invention relates to a compound of formula (XVIII):

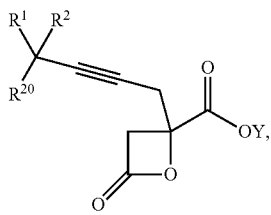

(XVIII)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{1R3}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

m is an integer from 0 to 2; and

Y is hydrogen or a protecting group, or a pharmaceutically acceptable salt thereof, or a solvate thereof.

126. Another embodiment relates to the compound as described in the paragraph above, wherein the compound is a substantially pure diastereomer having the structure:

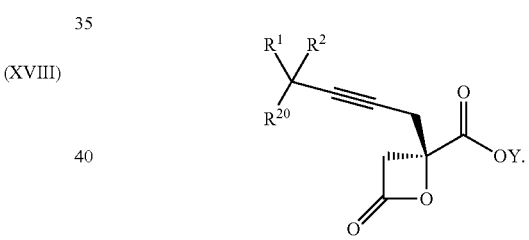

127. The present invention relates to a compound of formula (XIX):

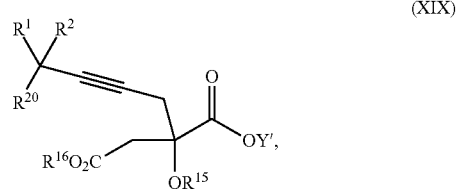

(XIX)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^{20}$ is hydrogen, halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

m is an integer from 0 to 2; and

Y' is hydrogen or a protecting group, or a pharmaceutically acceptable salt thereof, or a solvate thereof.

128. Another embodiment relates to the compound as described in the paragraph above, wherein the compound is a substantially pure diastereomer having the structure:

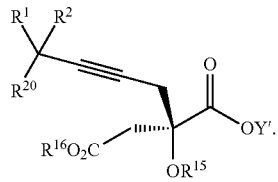

129. The present invention relates to a compound of formula (XX):

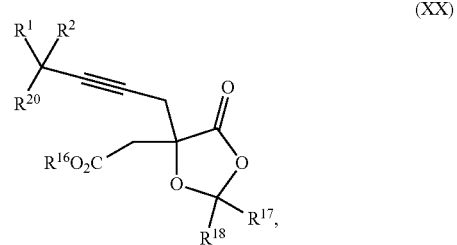

(XX)

wherein $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —NR$^{12}$R$^{13}$;

R$^{12}$ and R$^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or R$^{12}$ and R$^{13}$ are taken together with the nitrogen to which they are attached to form a piperidine, pyrrolidine, piperazine, N-methylpiperazine, morpholine, or thiomorpholine ring;

R$^{14}$ is $C_1$-$C_4$ alkyl, $C_1$-$C_4$ haloalkyl, or phenyl;

R$^{16}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^{10}$$_2$)(R$^9$)$_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with R$^{11}$;

R$^{17}$ is t-Bu, phenyl, naphthyl, CF$_3$, CCl$_3$, CBr$_3$, or $C_1$-$C_6$ alkoxy;

R$^{18}$ is H, Me, CF$_3$, CCl$_3$, CBr$_3$, or $C_1$-$C_6$ alkoxy; or

R$^{17}$ and R$^{18}$ combine with the carbon to which they are attached to form an internally bridged cycloalkyl, wherein the internally bridged cycloalkyl can be optionally substituted from 1 to 6 times with a substituent independently selected in each occurrence from $C_{1-6}$ alkyl and $C_{1-6}$ alkyl further substituted with —SO$_2$N($C_{1-6}$ alkyl)$_2$; or R$^{17}$ and R$^{18}$ are taken together to form a carbonyl, thiocarbonyl, sulfoxide, or sulfone;

R$^{20}$ is hydrogen, halogen, —NO$_2$, —OR$^{12}$, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with R$^{11}$; and m is an integer from 0 to 2,
or a pharmaceutically acceptable salt thereof, or a solvate thereof.

130. Another embodiment relates to the compound as described in the paragraph above, wherein the compound is a substantially pure diastereomer having the structure:

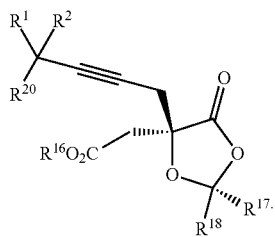

131. The present invention relates to a process for preparation of a product compound of formula (XXI):

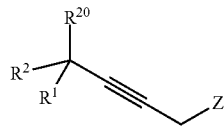

(XXI)

wherein

Z is selected from the group consisting of halogen, —OSO$_2$R$^{19}$, —OSO$_3$R$^{19}$, —OCOR$^{19}$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, and —N(R$^{19}$)$_3$$^+$;

R$^1$ and R$^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with R$^{11}$; or R$^1$ and R$^2$ are taken together to form a 5- to 7-membered ring having 0-2 heteroatoms independently selected from the group consisting of nitrogen, oxygen, and sulfur, optionally substituted from 1 to 3 times with R$^{11}$; or R$^1$ and R$^2$ are taken together to form a carbonyl, thiocarbonyl, sulfoxide, or sulfone;

R$^{11}$ is independently selected at each occurrence from a substituent in the group consisting of halogen, —NO$_2$, —OR$^{12}$, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —NR$^{12}$R$^{13}$;

R$^{12}$ and R$^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or R$^{12}$ and R$^{13}$ are taken together with the nitrogen to which they are attached to form a piperidine, pyrrolidine, piperazine, N-methylpiperazine, morpholine, or thiomorpholine ring;

R$^{14}$ is $C_1$-$C_4$ alkyl, $C_1$-$C_4$ haloalkyl, or phenyl;

R$^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with R$^{11}$;

R$^{20}$ is hydrogen, halogen, —NO$_2$, —OR$^{12}$, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with R$^{11}$; and m is an integer from 0 to 2,
or a pharmaceutically acceptable salt thereof, or a solvate thereof;
said method comprising:
providing a nineteenth intermediate compound of formula (XXIV):

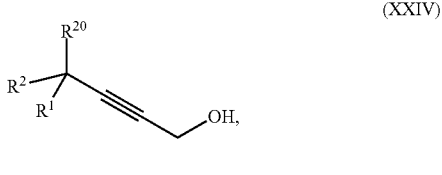

and
forming the product compound of formula (XXI) from the nineteenth intermediate compound.

132. Another embodiment relates to the process as described in the paragraph above, wherein said forming the product compound comprises:
subjecting the nineteenth intermediate compound to halogenation/deoxygenation conditions.

133. Another embodiment relates to the process as described in embodiment 131 further comprising:
providing a twentieth intermediate compound of formula (XXV)

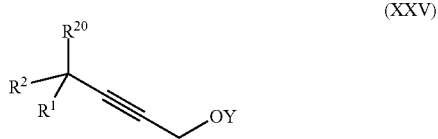

wherein Y is a protecting group, and forming the nineteenth intermediate compound of formula (XXIV) from the twentieth intermediate compound of formula (XXV).

134. Another embodiment relates to the process as described in the paragraph above, wherein said forming the nineteenth intermediate compound comprises reacting the twentieth intermediate compound with a protecting group removing agent.

135. Another embodiment relates to the process as described in embodiment 133, wherein the protecting group removing agent is n-Bu$_4$NF, NH$_4$F, HF, HF.pyridine, CsF, LiBF$_4$, BF$_3$.OEt$_2$, or HCl.

136. Another embodiment relates to the process as described in embodiment 133, wherein Y is a trisubstituted silyl group.

137. Another embodiment relates to the process as described in embodiment 133 further comprising:
providing a tenth intermediate compound of formula (XIV)

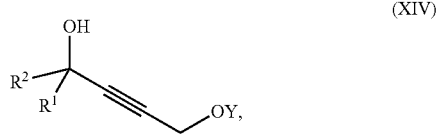

and
forming the twentieth intermediate compound of formula (XXV) from the tenth intermediate compound of formula (XIV).

138. Another embodiment relates to the process as described in embodiment 131, wherein Z is a halogen.

139. Another embodiment relates to the process as described in embodiment 131, wherein $R^1$ and $R^2$ are each $C_1$-$C_6$ alkyl.

140. The present invention relates to a compound of formula (IX):

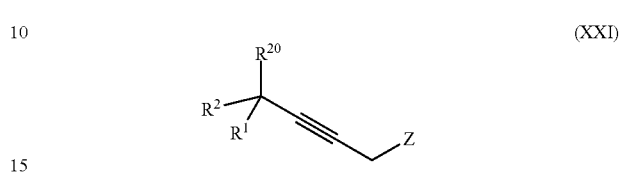

wherein
Z is selected from the group consisting of halogen, —OSO$_2$R$^{19}$, —OSO$_3$R$^{19}$, —OCOR$^{19}$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, —N(R$^{19}$)$_3^+$;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —NO$_2$, —OR$^{12}$, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —NR$^{12}$R$^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —C(O)R$^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl; $R^{19}$ is selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted with $R^{11}$ $R^{20}$ is hydrogen, halogen, —NO$_2$, —OR$^{12}$, —NR$^{12}$R$^{13}$, —NR$^{12}$C(O)$_2$R$^{13}$, —NR$^{12}$C(O)NR$^{12}$R$^{13}$, —S(O)$_m$R$^{13}$, —CN, —C(O)R$^{13}$, —C(O)NR$^{12}$R$^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; and m is an integer from 0 to 2, or a pharmaceutically acceptable salt thereof, or a solvate thereof.

141. Another embodiment relates to the compound as described in the paragraph above, wherein Z is a halogen.

142. Another embodiment relates to the compound as described in embodiment 140, wherein $R^1$ and $R^2$ are each $C_1$-$C_6$ alkyl.

143. The present invention relates to a compound of formula (XXVI):

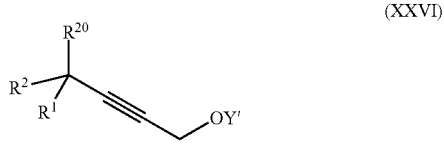

wherein

Y' is hydrogen or a protecting group;

$R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together to form a carbonyl, thiocarbonyl, sulfoxide, or sulfone;

$R^{11}$ is independently selected at each occurrence from a substituent in the group consisting of halogen, —$NO_2$, —OR, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring; and $R^{14}$ is $C_1$-$C_4$ alkyl, $C_1$-$C_4$ haloalkyl, or phenyl;

$R^{20}$ is hydrogen, halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; and m is an integer from 0 to 2, or a pharmaceutically acceptable salt thereof, or a solvate thereof.

144. Another embodiment relates to the compound as described in the paragraph above, wherein Y is a trisubstituted silyl group.

145. Another embodiment relates to the compound as described in embodiment 143, wherein $R^1$ and $R^2$ are each $C_1$-$C_6$ alkyl.

EXAMPLES

The following examples are provided to illustrate embodiments of the present technology, but they are by no means intended to limit the scope.

Example 1—Preparation of {[(5-Bromo-2-methyl-pent-3-yn-2-yl)oxy]methyl}benzene (6)

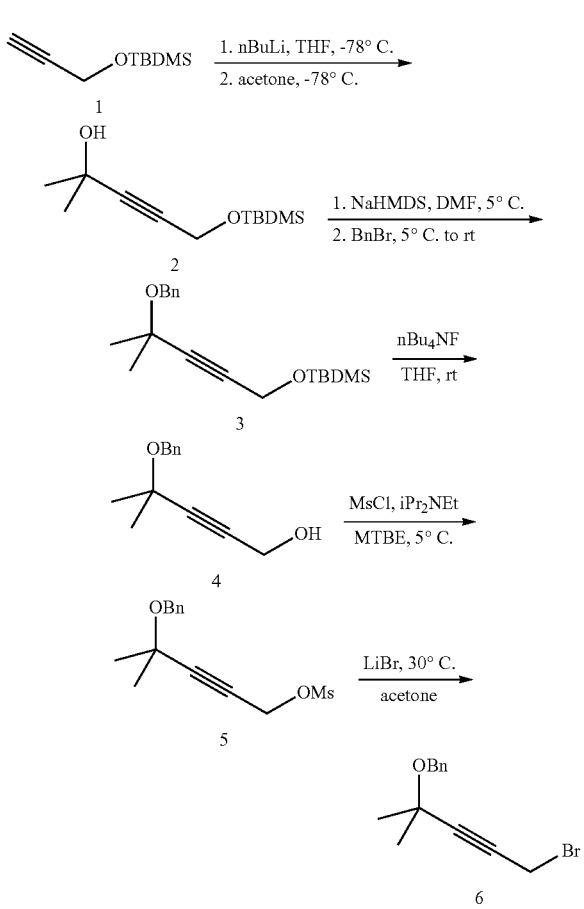

Step One. 5-[(Tert-Butyldimethylsilyl)oxy]-2-methylpent-3-yn-2-ol (2)

n-Butyllithium (167.2 mL, 451.6 mmol, 1.0 equiv, 2.7 M in heptanes) was added to a solution of tert-butyldimethyl (prop-2-yn-1-yloxy)silane (1, 76.93 g, 451.6 mmol) in anhydrous THF (600 mL) at −78° C. under nitrogen at a rate which maintained the internal reaction mixture below −66° C., after which the mixture was stirred at −78° C. for 25 minutes. Acetone (45 mL, 612.8 mmol, 1.35 equiv) was then added at a rate which maintained the internal reaction mixture below −66° C., after which the mixture was stirred at −78° C. for 20 minutes. The mixture was treated with saturated aqueous ammonium chloride solution (38 mL) and allowed to warm to room temperature. Water (200 mL) was added and the mixture was extracted with ethyl acetate (1×300 mL, 1×100 mL). The combined organic extracts were dried with sodium sulfate, filtered and the solvents were removed under reduced pressure to afford crude 2 as a light yellow oil that was suitable for use in the next step without further purification (108 g): $^1$H NMR (500 MHz, CDCl$_3$) δ 4.33 (s, 2H), 1.51 (s, 6H), 0.92 (s, 9H), 0.11 (s, 6H) ppm.

Step Two. {[4-(Benzyloxy)-4-methylpent-2-yn-1-yl]oxy}(tert-butyl)dimethylsilane (3)

Sodium bis(trimethylsilyl)amide (225 mL, 449.3 mmol, 1.1 equiv, 2.0 M in THF) was added to a solution of 5-[(tert-butyldimethylsilyl)oxy]-2-methylpent-3-yn-2-ol (2, 93.3 g, 408.8 mmol) in anhydrous DMF (500 mL) at 0-5° C. under nitrogen at a rate which maintained the internal reaction mixture between 0-5° C., after which the mixture was stirred at 0-5° C. for 30 minutes. Benzyl bromide (58.3 mL, 490.5 mmol, 1.2 equiv) was added at a rate which maintained the internal reaction mixture between 5-25° C., after which the mixture was stirred at 20-25° C. for 4 hours. The mixture was treated with additional sodium bis(trimethylsilyl)amide (29.6 mL, 59.2 mmol, 0.15 equiv, 2.0 M in THF) in a single portion, after which the mixture was stirred at 20-25° C. for 30 minutes. The mixture was treated with water (250 mL) followed by MTBE (500 mL), after which the MTBE layer was collected. The aqueous layer was extracted with MTBE (250 mL) and the combined organic extracts were washed with water (250 mL) and the solvents were removed under reduced pressure to afford crude 3 as a light yellow oil that was suitable for use in the next step without further purification (145 g): $^1$H NMR (300 MHz, CDCl$_3$) δ 7.36-7.29 (m, 4H), 7.27-7.21 (m, 1H), 4.61 (s, 2H), 4.38 (s, 2H), 1.51 (s, 6H), 0.92 (s, 9H), 0.11 (s, 6H) ppm.

Step Three. 4-Benzyloxy-4-methylpent-2-yn-1-ol (4)

Tetrabutylammonium fluoride (500 mL, 500.0 mmol, 1.2 equiv, 1.0 M in THF) was added to a solution of [(4-benzyloxy-4-methylpent-2-yn-1-yl)oxy](tert-butyl)dimethylsilane (3, 145 g, 408 mmol) in anhydrous THF (500 mL) at 18-25° C. under nitrogen, and the mixture was stirred at 18-25° C. for 3-18 hours. The mixture was treated with MTBE (500 mL), water (500 mL), and 2N HCl (250 mL) and the organic layer was collected. The aqueous layer was extracted with MTBE (400 mL), after which the organic extracts were combined and the solvents were removed under reduced pressure to afford a cloudy orange oil. This oil was dissolved in acetonitrile (500 mL) and the mixture was washed with heptanes (3×400 mL). The orange acetonitrile layer was collected and the solvent was removed under reduced pressure to afford crude 4 as a clear orange oil that was suitable for use in the next step without further purification (71.0 g, 85% over two steps): $^1$H NMR (500 MHz, CDCl$_3$) δ 7.55 (br s, 1H), 7.37-7.30 (m, 4H), 7.27-7.23 (m, 1H), 4.62 (s, 2H), 4.30 (s, 2H), 1.56 (s, 6H) ppm.

Step Four. 4-Benzyloxy-4-methylpent-2-yn-1-yl methanesulfonate (5)

Diisopropylethylamine (59 mL, 339 mmol, 1.5 equiv) was added in one portion to a solution of 4-benzyloxy-4-methylpent-2-yn-1-ol (4, 42.6 g, 226 mmol) in anhydrous MTBE (250 mL) at 5-10° C. under nitrogen, after which methanesulfonyl chloride (19.6 mL, 254 mmol, 1.13 equiv) was added at a rate which maintained the internal batch temperature below 15° C. The mixture was stirred for 15 minutes after which the mixture was washed with water (125 mL), 2N HCl (125 mL), saturated aqueous sodium hydrogen carbonate solution (125 mL), and brine (125 mL). The solvents were removed under reduced pressure to afford crude 5 as a clear orange oil that was suitable for use in the next step without further purification (65.7 g): $^1$H NMR (500 MHz, CDCl$_3$) δ 7.35-7.32 (m, 4H), 7.28-7.25 (m, 1H), 4.90 (s, 2H), 4.61 (s, 2H), 3.08 (s, 3H), 1.58 (s, 6H) ppm.

Step Five. {[(5-Bromo-2-methylpent-3-yn-2-yl)oxy]methyl}benzene (6)

Lithium bromide (39.2 g, 452 mmol, 2.0 equiv) was added portion-wise over 10 min to a solution of 4-benzyloxy-4-methylpent-2-yn-1-yl methanesulfonate (5, 63.8 g, 226 mmol) in anhydrous acetone (190 mL) at room temperature under nitrogen, after which the mixture was heated at 30° C. and stirred for 30 minutes. Water (100 mL) and MTBE (200 mL) were added and the aqueous layer was discarded. The organic extract was washed with saturated aqueous sodium hydrogen carbonate solution (100 mL) and water (100 mL), after which the solvents were removed under reduced pressure. The residue was diluted with additional MTBE (100 mL) and again the solvent was removed under reduced pressure. The residue was purified by short-path distillation under reduced pressure (100-105° C. at 0.26 Torr) to afford 6 as a clear pale yellow oil (56.2 g, 93% over two steps): $^1$H NMR (500 MHz, CDCl$_3$) δ 7.37-7.31 (m, 4H), 7.28-7.25 (m, 1H), 4.61 (s, 2H), 3.96 (s, 2H), 1.53 (s, 6H) ppm.

Example 2—Preparation of {[(5-Iodo-2-methylpent-3-yn-2-yl)oxy]methyl}benzene (7)

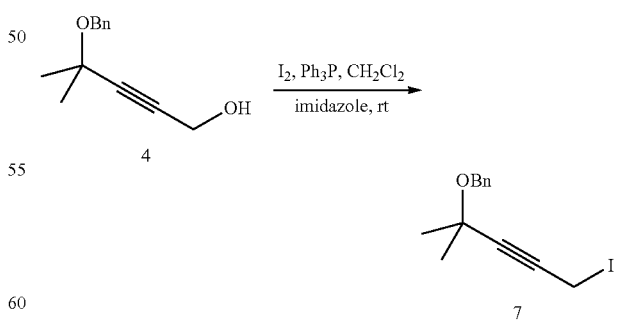

Iodine crystals (34.8 g, 137 mmol, 1.4 equiv) were added portion-wise to a solution of triphenylphosphine (33.4 g, 127 mmol, 1.3 equiv) and imidazole (9.3 g, 137 mmol, 1.4 equiv) in anhydrous dichloromethane (950 mL) at room temperature under nitrogen, after which the mixture was stirred at room temperature for 10 minutes. A solution of 4 (20.0 g, 98 mmol) in anhydrous dichloromethane (50 mL) was added, after which the mixture was stirred at room temperature for 3.5 hours. The mixture was diluted with saturated aqueous sodium thiosulfate solution (500 mL) and stirred for 5 minutes, after which the organic later was collected and the solvent was removed under reduced pressure to a volume of about 500 mL. The mixture was diluted with heptanes (500 mL) and again the solvent was removed under reduced pressure to a volume of about 400 mL. The solids were removed by filtration under reduced pressure and the filter cake was washed with heptanes (2×50 mL). The filtrate extracts were combined and the solvents were removed under reduced pressure to afford 7 as a pale yellow oil that was suitable for use in the next step without further purification (31.6 g): $^1$H NMR (300 MHz, CDCl$_3$) δ 7.40-7.23 (m, 5H), 4.61 (s, 2H), 3.74 (s, 2H), 1.51 (s, 6H) ppm.

Example 3—Route I Preparation of Cephalotaxine 3-[4-Methyl-(2R)-2-hydroxy-2-(4-hydroxy-4-methylpentyl)succinate] (15)

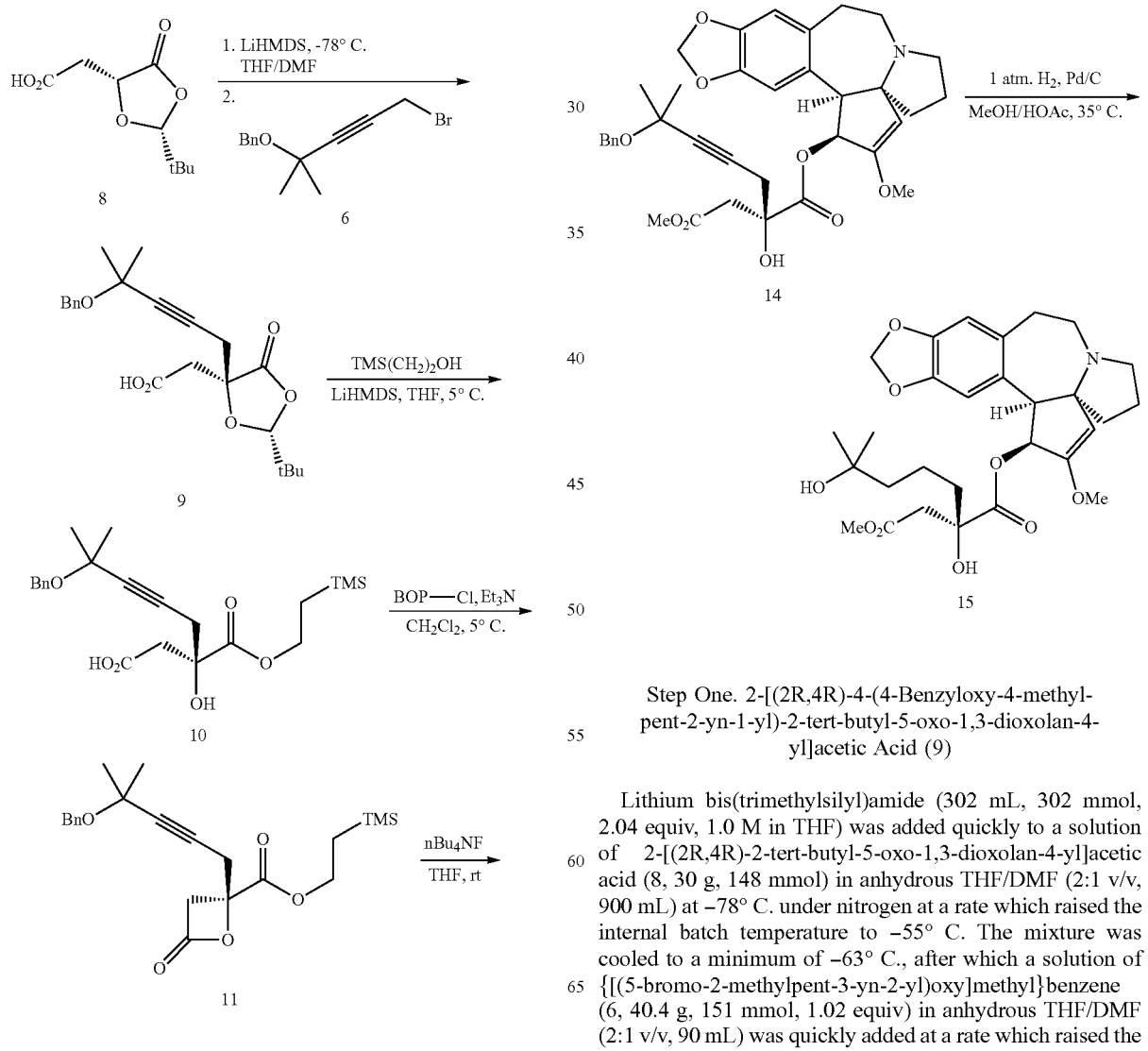

Step One. 2-[(2R,4R)-4-(4-Benzyloxy-4-methylpent-2-yn-1-yl)-2-tert-butyl-5-oxo-1,3-dioxolan-4-yl]acetic Acid (9)

Lithium bis(trimethylsilyl)amide (302 mL, 302 mmol, 2.04 equiv, 1.0 M in THF) was added quickly to a solution of 2-[(2R,4R)-2-tert-butyl-5-oxo-1,3-dioxolan-4-yl]acetic acid (8, 30 g, 148 mmol) in anhydrous THF/DMF (2:1 v/v, 900 mL) at −78° C. under nitrogen at a rate which raised the internal batch temperature to −55° C. The mixture was cooled to a minimum of −63° C., after which a solution of {[(5-bromo-2-methylpent-3-yn-2-yl)oxy]methyl}benzene (6, 40.4 g, 151 mmol, 1.02 equiv) in anhydrous THF/DMF (2:1 v/v, 90 mL) was quickly added at a rate which raised the internal batch temperature to −50° C. The resulting cream-colored suspension was stirred for 1 hour during which time the internal reaction temperature was maintained below −65° C., after which the mixture was allowed to slowly warm to −30 to −20° C. The mixture was treated over 5-10 minutes with 2N HCl (300 mL), after which MTBE (600 mL) and heptanes (600 mL) were added. The mixture was agitated for 5 minutes, after which the layers were allowed to separate for a minimum of 15 minutes. The aqueous layer was discarded and the organic layer was washed with water (2×300 mL) and the solvents were removed under reduced pressure to produce a yellow-orange oil. The residue was dissolved in dichloromethane (60 mL) and rapidly diluted with heptanes (900 mL), resulting in a flocculent white suspension that gradually became more stirrable over time. The suspension was stirred at 18-25° C. for 2-24 hours, after which the solids were collected under reduced pressure, washing the filter cake with dichloromethane/heptanes (1:19, 2×90 mL). The cake was conditioned for 2 hours after which the crude product was dissolved in dichloromethane (400 mL) and any suspended solids were removed by filtration through a pad of diatomaceous earth under reduced pressure. The filtrate solvents were removed under reduced pressure to give a cream colored solid residue that was then dissolved in dichloromethane (40 mL) and rapidly diluted with heptanes (600 mL). The resulting suspension was warmed to 30° C. and then cooled to 18-25° C. for 2-24 hours, at which point the solids were collected under reduced pressure, washing the cake with dichloromethane/heptanes (1:19, 2×90 mL). The cake was conditioned for 2 hours and then dried overnight to afford 9 as a bright white solid (16.4 g, 29%): $^1$H NMR (500 MHz, CDCl$_3$) δ 10.1 (br s, 1H), 7.36-7.30 (m, 4H), 7.26-7.24 (m, 1H), 5.44 (s, 1H), 4.60 (s, 2H), 2.93-2.87 (m, 2H), 2.84-2.77 (m, 2H), 1.52 (s, 6H), 0.95 (s, 9H) ppm.

Step Two. (R)-7-Benzyloxy-3-hydroxy-7-methyl-3-{[2-(trimethylsilyl)ethoxy]carbonyl}oct-5-ynoic Acid (10)

2-(Trimethylsilyl)ethanol (8.27 mL, 57.6 mmol, 1.5 equiv) was added to a solution of 2-[(2R,4R)-4-(4-benzyloxy-4-methylpent-2-yn-1-yl]-2-tert-butyl-5-oxo-1,3-dioxolan-4-yl]acetic acid (9, 14.9 g, 38.3 mmol) in anhydrous THF (300 mL) at 0-5° C. under nitrogen, after which lithium bis(trimethylsilyl)amide (96.2 mL, 96.2 mmol, 2.5 equiv, 1.0 M in THF) was added at a rate which maintained the internal reaction temperature below 10° C. The mixture was warmed to 20° C. and stirred for 1-1.5 hours, after which the mixture was cooled to 0-5° C. and treated rapidly with 1N HCl (288 mL, 288 mmol). The mixture was further treated with MTBE (300 mL) and water (300 mL) and the organic layer was collected. The aqueous layer was extracted with MTBE (150 mL) and the combined organic extracts were dried with sodium sulfate, filtered and the solvents were removed under reduced pressure. The residue was purified by column chromatography on silica gel, eluting with methanol/dichloromethane (1:19), to provide a light yellow oil that was further triturated with heptanes to afford 10 as a white solid (13.9 g, 86%): $^1$H NMR (500 MHz, CDCl$_3$) δ 9.72 (br s, 1H), 7.36-7.30 (m, 4H), 7.26-7.23 (m, 1H), 4.59 (s, 2H), 4.28 (m, 2H), 3.87 (br s, 1H), 3.01 (d, J=16.5 Hz, 1H), 2.82 (d, J=16.5 Hz, 1H), 2.67 (s, 2H), 1.51 (s, 6H), 1.03 (m, 2H), 0.03 (s, 9H) ppm.

Step Three. (R)-2-(Trimethylsilyl)ethyl-2-(4-benzyloxy-4-methylpent-2-yn-1-yl)-4-oxooxetane-2-carboxylate (11)

Triethylamine (12.94 mL, 92.8 mmol, 2.8 equiv) was added to a solution of bis(2-oxo-3-oxazolidinyl)phosphinic chloride (10.97 g, 43.0 mmol, 1.3 equiv) in anhydrous dichloromethane (420 mL) at 5° C. under nitrogen, after which a solution of (R)-7-benzyloxy-3-hydroxy-7-methyl-3-{[2-(trimethylsilyl)ethoxy]carbonyl}oct-5-ynoic acid (10, 13.9 g, 33.3 mmol) in anhydrous dichloromethane (210 mL) was added over 1.5 hours. The mixture was stirred at 5° C. for 2-2.5 hours and then treated with water (150 mL). The organic layer was collected and the aqueous layer was extracted with dichloromethane (150 mL). The combined organic extracts were dried with sodium sulfate, filtered and the solvents were removed under reduced pressure. The residue was purified by column chromatography on silica gel, eluting with dichloromethane, to afford 11 as an amber oil (5.56 g, 42%): $^1$H NMR (500 MHz, CDCl$_3$) δ 7.36-7.31 (m, 4H), 7.27-7.23 (m, 1H), 4.58 (m, 2H), 4.32 (m, 2H), 3.70 (d, J=16 Hz, 1H), 3.62 (d, J=16 Hz, 1H), 3.07 (m, 2H), 1.52 (s, 6H), 1.05 (m, 2H), 0.05 (s, 9H) ppm.

Step Four. (R)-2-(4-Benzyloxy-4-methylpent-2-yn-1-yl)-4-oxooxetane-2-carboxylic Acid (12)

Tetrabutylammonium fluoride (15.1 mL, 15.1 mmol, 1.1 equiv, 1.0 M in THF) was added to a solution of (R)-2-(trimethylsilyl)ethyl-2-(4-benzyloxy-4-methylpent-2-yn-1-yl)-4-oxooxetane-2-carboxylate (11, 5.56 g, 13.8 mmol) in anhydrous THF (111 mL) at 20° C. under nitrogen, after which the mixture was stirred for 1 hour. The mixture was treated with water (80 mL), 1N HCl (16 mL), and MTBE (100 mL) and the organic layer was collected. The aqueous layer was extracted with MTBE (50 mL) and the combined organic extracts were dried with sodium sulfate, filtered and the solvents were removed under reduced pressure. The residue was purified by column chromatography on silica gel, eluting with methanol/dichloromethane (1:19), to afford 12 as an amber oil (3.15 g, 74%): $^1$H NMR (500 MHz, CDCl$_3$) δ 7.35-7.31 (m, 4H), 7.26-7.24 (m, 1H), 6.42 (br s, 1H), 4.58 (s, 2H), 3.71 (m, 2H), 3.09 (m, 2H), 1.53 (s, 6H) ppm.

Step Five. (R)-2-(4-Benzyloxy-4-methylpent-2-yn-1-yl)-4-oxooxetane-2-cephalotaxyl Carboxylate (13)

2,4,6-Trichlorobenzoyl chloride (0.40 mL, 2.56 mmol, 2.25 equiv) was added to a solution of (R)-2-(4-benzyloxy-4-methylpent-2-yn-1-yl)-4-oxooxetane-2-carboxylic acid (12, 0.74 g, 2.44 mmol, 2.15 equiv) and triethylamine (0.51 mL, 3.65 mmol, 3.20 equiv) in anhydrous dichloromethane (19 mL) at 20° C. under nitrogen, after which the mixture was stirred for 1 hour. 4-Dimethylaminopyridine (0.33 g, 2.70 mmol, 2.35 equiv) was added, after which the mixture was stirred for 5 minutes. (−)-Cephalotaxine (0.36 g, 1.14 mmol) was added, and the mixture was stirred for an additional 70 minutes. The reaction mixture was concentrated to about a fifth of the volume and the mixture was directly purified by column chromatography on silica gel, eluting with methanol/dichloromethane (1:9), to afford 13 as an amber oil (0.69 g, 94%): $^1$H NMR (500 MHz, CDCl$_3$) δ

7.35-7.30 (m, 4H), 7.26-7.23 (m, 1H), 6.62 (s, 1H), 6.58 (s, 1H), 5.87 (m, 3H), 5.09 (s, 1H), 4.54 (m, 2H), 3.81 (d, J=9.5 Hz, 1H), 3.68 (s, 3H), 3.33 (d, J=16 Hz, 1H), 3.07 (m, 2H), 2.95 (d, J=16 Hz, 1H), 2.92 (m, 1H), 2.70 (d, J=18 Hz, 1H), 2.60 (d, J=18 Hz, 1H), 2.59 (m, 2H), 2.36 (m, 1H), 2.03 (m, 1H), 1.90 (m, 1H), 1.75 (m, 2H), 1.49 (s, 6H) ppm.

Step Six. (R)-1-Cephalotaxyl 4-Methyl-2-(benzyloxy-4-methylpent-2-yn-1-yl)-2-hydroxysuccinate (14)

Sodium methoxide (1.36 mL, 0.68 mmol, 0.5 M in methanol) was added to a mixture of (R)-2-(4-benzyloxy-4-methylpent-2-yn-1-yl)-4-oxooxetane-2-cephalotaxyl carboxylate (13, 0.43 g, 0.71 mmol, 1.20 equiv) in anhydrous methanol (6.5 mL) at 0-5° C. under nitrogen, and the mixture was stirred for 25 minutes. Saturated aqueous ammonium chloride solution (12 mL) was added, followed by dichloromethane (30 mL). The organic layer was collected and the aqueous layer was extracted with dichloromethane (30 mL). The combined organic extracts were dried with sodium sulfate, filtered and the solvents were removed under reduced pressure. The residue was purified by column chromatography on silica gel, eluting with methanol/dichloromethane (1:9), to afford 14 as an amber oil (0.17 g, 38%): $^1$H NMR (500 MHz, CDCl$_3$) δ 7.37-7.30 (m, 4H), 7.26-7.23 (m, 1H), 6.61 (s, 1H), 6.54 (s, 1H), 5.94 (m, 1H), 5.86 (m, 2H), 5.03 (s, 1H), 4.59 (s, 2H), 3.77 (d, J=10 Hz, 1H), 3.65 (s, 3H), 3.63 (s, 1H), 3.59 (s, 3H), 3.10 (m, 2H), 2.93 (m, 1H), 2.58 (m, 2H), 2.45 (d, J=16 Hz, 1H), 2.38 (m, 1H), 2.35 (s, 2H), 2.07 (d, J=16 Hz, 1H), 2.02 (m, 1H), 1.89 (m, 1H), 1.75 (m, 2H), 1.50 (s, 6H) ppm.

Step Seven. Cephalotaxine 3-[4-Methyl-(2R)-2-hydroxy-2-(4-hydroxy-4-methylpentyl)succinate] (15)

5% Palladium on carbon (340 mg, 50 wt %) was added to a solution of (R)-1-cephalotaxyl 4-methyl-2-(benzyloxy-4-methylpent-2-yn-1-yl)-2-hydroxysuccinate (14, 0.68 g, 1.07 mmol) in anhydrous methanol (25 mL) and acetic acid (2.5 mL), after which the reaction vessel was evacuated and refilled with an atmosphere of hydrogen gas. The evacuation/refill procedure was repeated two more times, after which the mixture was heated to 35° C. and stirred for 2 hours. The mixture was filtered through a pad of diatomaceous earth under reduced pressure, and the solvents were removed under reduced pressure. The residue was dissolved in dichloromethane (20 mL), washed with 1.25 N aqueous ammonium hydroxide solution (10 mL) and the solvent was removed under reduced pressure. This residue was purified by column chromatography on silica gel, eluting with methanol/dichloromethane (1:4), to afford the product as a white foam (0.45 g, 76%), which was then recrystallized from diethyl ether/heptanes to afford 15 as a white solid (0.33 g, 57%): $^1$H NMR (500 MHz, CDCl$_3$) δ 6.62 (s, 1H), 6.54 (s, 1H), 6.00 (m, 1H), 5.86 (m, 2H), 5.05 (s, 1H), 3.77 (d, J=9.5 Hz, 1H), 3.68 (s, 3H), 3.57 (s, 3H), 3.51 (s, 1H), 3.10 (m, 2H), 2.94 (m, 1H), 2.59 (m, 2H), 2.38 (m, 1H), 2.26 (d, J=16 Hz, 1H), 2.03 (m, 1H), 1.91 (d, J=16 Hz, 1H), 1.90 (m, 1H), 1.75 (m, 2H), 1.47-1.35 (m, 5H), 1.29-1.20 (m, 2H), 1.19 (s, 3H), 1.18 (s, 3H) ppm.

Example 4—Route II Preparation of (R)-1-Cephalotaxyl 4-Methyl-2-(benzyloxy-4-methylpent-2-yn-1-yl)-2-hydroxysuccinate (14)

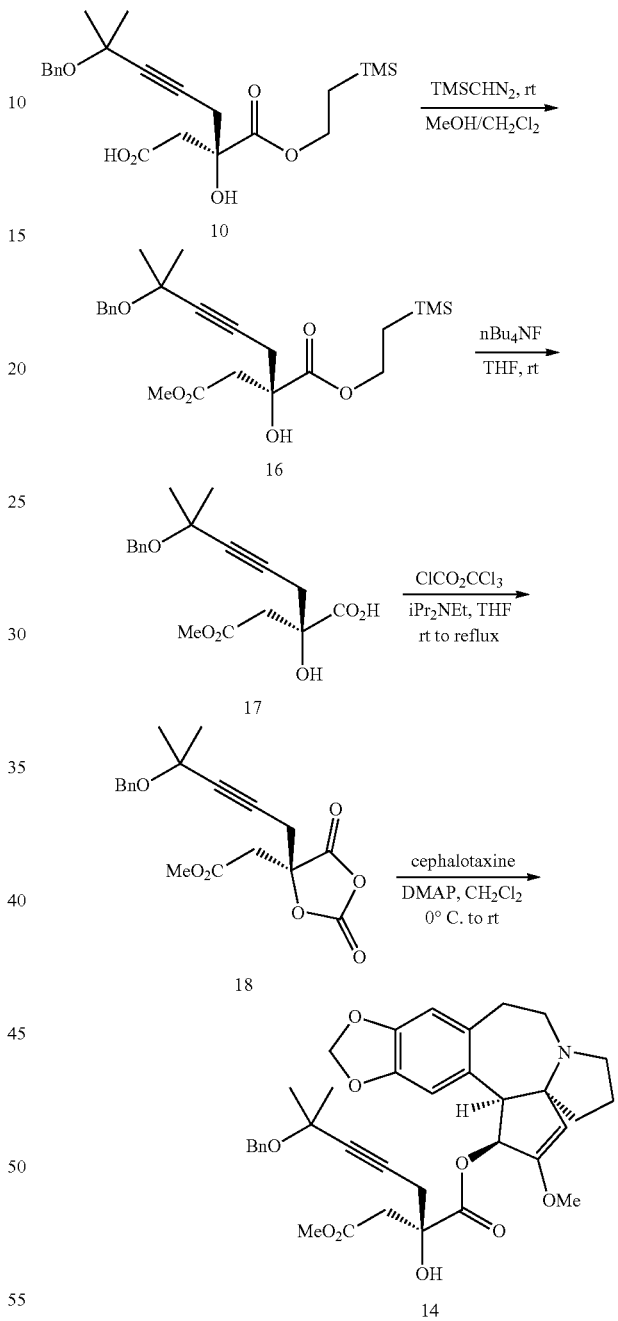

Step One. (R)-4-Methyl 1-[2-(trimethylsilyl)ethyl] 2-(4-Benzyloxy-4-methylpent-2-yn-1-yl)-2-hydroxysuccinate (16)

(Trimethylsilyl)diazomethane (1.4 mL, 2.9 mmol, 1.5 equiv, 2.0 M in hexanes) was added drop-wise to a solution of (R)-7-benzyloxy-3-hydroxy-7-methyl-3-{[2-(trimethylsilyl)ethoxy]carbonyl}oct-5-ynoic acid (10, 810 mg, 1.9 mmol) in anhydrous methanol (2.0 mL) and anhydrous dichloromethane (8.0 mL) at room temperature under nitrogen, after which the mixture was stirred at room temperature for 30 minutes. The solvents were removed under reduced pressure and the residue was purified by column chromatography on silica gel, eluting with ethyl acetate/heptanes (1:4), to provide 16 as a light amber oil (394 mg, 47%): $^1$H NMR (300 MHz, CDCl$_3$) δ 7.39-7.22 (m, 5H), 4.59 (s, 2H), 4.32-4.25 (m, 2H), 3.69 (s, 3H), 2.87 (dd, J=15.9, 59.6 Hz, 2H), 2.66 (s, 2H), 1.51 (s, 6H), 1.07-1.01 (m, 2H), 0.02 (s, 9H) ppm.

Step Two. (R)-6-Benzyloxy-2-hydroxy-2-(2-methoxy-2-oxoethyl)-6-methylhept-4-ynoic Acid (17)

Tetrabutylammonium fluoride (1.4 mL, 1.4 mmol, 1.5 equiv, 1.0 M in THF) was added drop-wise to a solution of (R)-4-methyl 1-[2-(trimethylsilyl)ethyl] 2-(4-benzyloxy-4-methylpent-2-yn-1-yl)-2-hydroxysuccinate (16, 394 mg, 0.91 mmol) in anhydrous THF (8.0 mL) at room temperature under nitrogen, after which the mixture was stirred at room temperature for 2.5 hours. The mixture was diluted with MTBE (100 mL), washed with 1N HCl (100 mL) and brine (50 mL). The organic extract was dried with sodium sulfate, filtered and the solvents were removed under reduced pressure to afford crude 17 as a yellow oil that was suitable for use in the next step without further purification (303 mg): $^1$H NMR (300 MHz, CDCl$_3$) δ 7.39-7.31 (m, 4H), 7.28-7.24 (m, 1H), 4.60 (s, 2H), 3.72 (s, 3H), 2.93 (dd, J=16.4, 67.1 Hz), 2.70 (s, 2H), 1.52 (s, 6H) ppm.

Step Three. (R)-Methyl 2-[4-(4-Benzyloxy-4-methylpent-2-yn-1-yl)-2, 5-dioxo-1,3-dioxolan-4-yl]acetate (18)

Diisopropylethylamine (0.39 mL, 2.2 mmol, 2.45 equiv) was added to a solution of (R)-6-benzyloxy-2-hydroxy-2-(2-methoxy-2-oxoethyl)-6-methylhept-4-ynoic acid (17, 303 mg, 0.90 mmol) from the previous step in anhydrous THF (4.0 mL) at room temperature under nitrogen. A solution of trichloromethyl chloroformate (0.31 mL, 1.8 mmol, 1.0 equiv) in anhydrous THF (1.0 mL) was added, after which the mixture was heated to 60-65° C. and stirred for 90 minutes. The solvents were removed from the cooled mixture under reduced pressure, and the residue was purified by column chromatography on silica gel, eluting with ethyl acetate/heptanes (1:1), to provide 18 as a colorless oil (180 mg, 26% over two steps): $^1$H NMR (300 MHz, CDCl$_3$) δ 7.36-7.33 (m, 4H), 7.29-7.26 (m, 1H), 4.56 (s, 2H), 3.76 (s, 3H), 3.10 (dd, J=18.0, 26.8 Hz, 2H), 2.88 (s, 2H), 1.52 (s, 6H) ppm.

Step Four. (R)-1-Cephalotaxyl 4-Methyl-2-(benzyloxy-4-methylpent-2-yn-1-yl)-2-hydroxysuccinate (14)

A solution of (R)-methyl 2-[4-(4-benzyloxy-4-methylpent-2-yn-1-yl)-2,5-dioxo-1,3-dioxolan-4-yl]acetate (18, 180 mg, 0.50 mmol, 1.5 equiv) in anhydrous dichloromethane (1.0 mL) was added drop-wise to a solution of cephalotaxine (105 mg, 0.33 mmol) in anhydrous dichloromethane (2.0 mL) at 0-5° C. under nitrogen. 4-Dimethylaminopyridine (41 mg, 0.33 mmol, 1.0 equiv) was added in one portion, after which the mixture was slowly warmed to room temperature, stirring for a total of 3 hours. The mixture was directly purified by column chromatography on silica gel, eluting with methanol/dichloromethane (1:19), to provide 14 as an amber oil (62 mg, 30%).

A final step to obtain cephalotaxine 3-[4-Methyl-(2R)-2-hydroxy-2-(4-hydroxy-4-methylpentyl)succinate] 15 can be carried out as described in Example 3.

Example 5—Route III Preparation of (R)-1-Cephalotaxyl 4-Methyl-2-(benzyloxy-4-methylpent-2-yn-1-yl)-2-hydroxysuccinate (14)

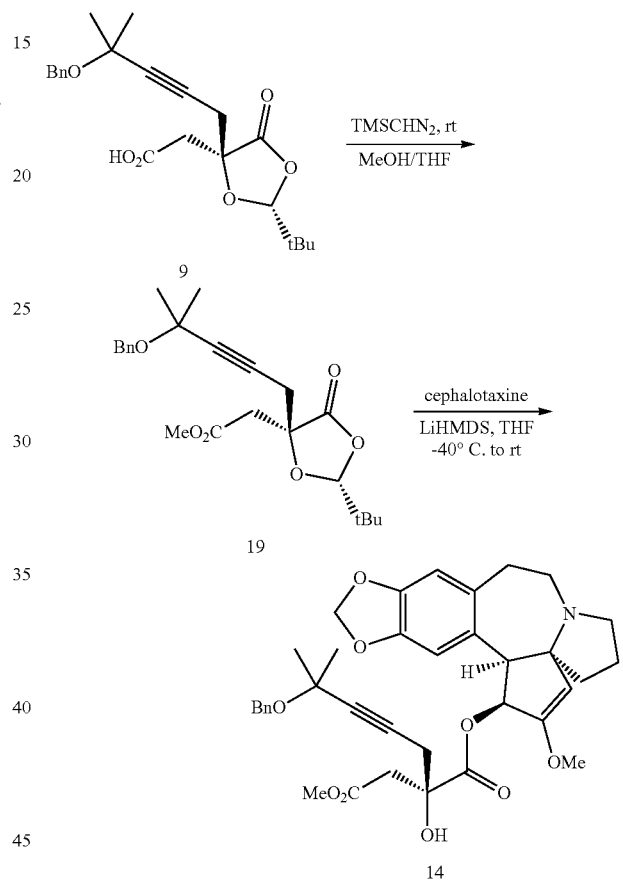

Step One. Methyl 2-[(2R,4R)-4-(4-Benzyloxy-4-methylpent-2-yn-1-yl)-2-tert-butyl-5-oxo-1,3-dioxolan-4-yl]acetate (19)

(Trimethylsilyl)diazomethane (0.38 mL, 0.76 mmol, 1.45 equiv, 2.0 M in hexanes) was added drop-wise to a solution of 2-[(2R,4R)-4-(4-benzyloxy-4-methylpent-2-yn-1-yl)-2-tert-butyl-5-oxo-1,3-dioxolan-4-yl]acetic acid (9, 200 mg, 0.52 mmol) in anhydrous methanol (0.8 mL) and anhydrous THF (5.0 mL) at room temperature under nitrogen, after which the mixture was stirred at room temperature for 1 hour. The solvents were removed under reduced pressure and the residue was purified by column chromatography on silica gel, eluting with ethyl acetate/heptanes (1:3), to provide 17 as a light amber oil (173 mg, 83%): $^1$H NMR (500 MHz, CDCl$_3$) δ 7.37-7.30 (m, 4H), 7.26-7.23 (m, 1H), 5.44 (s, 1H), 4.60 (s, 2H), 3.69 (s, 3H), 2.89 (d, J=7.2 Hz, 2H), 2.83 (d, J=17.4 Hz, 2H), 1.52 (s, 6H), 0.94 (s, 9H) ppm.

Step Two. (R)-1-Cephalotaxyl 4-Methyl-2-(benzyloxy-4-methylpent-2-yn-1-yl)-2-hydroxysuccinate (14)

Lithium bis(trimethylsilyl)amide (0.43 mL, 0.43 mmol, 1.5 equiv, 1.0 M in THF) was added drop-wise to a solution of cephalotaxine (90 mg, 0.28 mmol) in anhydrous THF (1.5 mL) at −40° C. under nitrogen, after which the mixture was stirred at −40° C. for 15 minutes. A solution of methyl 2-[(2R,4R)-4-(4-benzyloxy-4-methylpent-2-yn-1-yl)-2-tert-butyl-5-oxo-1,3-dioxolan-4-yl]acetate (19, 173 mg, 0.43 mmol, 1.5 equiv) in anhydrous THF (0.7 mL), after which the mixture was slowly warmed to room temperature, stirring for a total of 12 hours. The mixture was diluted with saturated aqueous ammonium chloride solution (10 mL) and extracted with ethyl acetate (3×30 mL). The combined organic extracts were dried with sodium sulfate, filtered and the solvents were removed under reduced pressure. The residue was purified by column chromatography on silica gel, eluting with methanol/dichloromethane (1:9), to afford 14 as an amber oil (19 mg, 11%).

A final step to obtain cephalotaxine 3-[4-Methyl-(2R)-2-hydroxy-2-(4-hydroxy-4-methylpentyl)succinate] 15 can be carried out as described in Example 3.

Example 6—Route IV Preparation of Cephalotaxine 3-[4-Methyl-(2R)-2-hydroxy-2-(4-hydroxy-4-methylpentyl)succinate] (15)

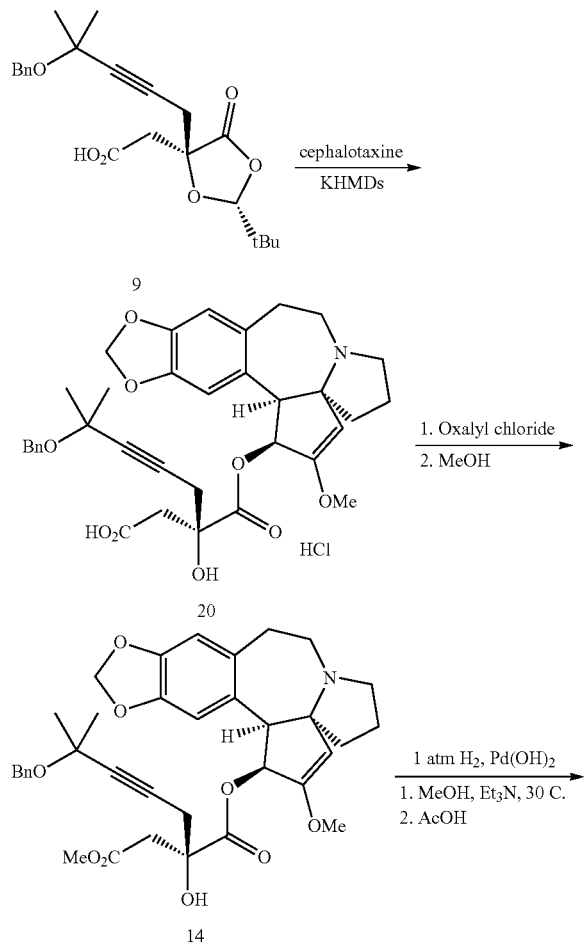

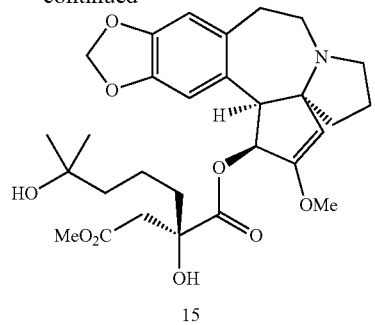

15

Step One. Preparation of (R)-7-(benzyloxy)-3-hydroxy-3-(((((11bS,12S,14aR)-13-methoxy-2,3,5,6,11b,12-hexahydro-1H-[1,3]dioxolo[4',5':4,5]benzo[1,2-d]cyclopenta[b]pyrrolo[1,2-a]azepin-12-yl)oxy)carbonyl)-7-methyloct-5-ynoic acid hydrochloride (20)

(−)-Cephalotaxine (11.1 g, 35.2 mmol) and 2-((2R,4R)-4-(4-(benzyloxy)-4-methylpent-2-yn-1-yl)-2-(tert-butyl)-5-oxo-1,3-dioxolan-4-yl)acetic acid) (9, 16.21 g, 42.2 mmol, 1.2 equiv) were dissolved in anhydrous THF (300 mL, 27 Vol) and maintained at room temperature. To this solution was rapidly added KHMDS (1 M THF, 73.9 mL, 73.9 mmol, 2.1 equiv) over 10-20 minutes. The solution was allowed to stir at room temperature for an additional 25 minutes then quenched by adding to a separate flask containing precooled (5-15° C.) 1 M HCl (aq, 218 mL, 20 Vol). The rate of transfer was set so as to maintain an internal batch temperature <30° C. The batch was stirred at 15-30° C. for an additional 5-15 minutes then n-heptane (440 mL, 40 Vol) was added and stirring continued for an additional 10 minutes. After allowing the batch to settle for 20 minutes, the bottom aqueous layer was removed and washed a second time with n-heptane (440 mL, 40 Vol). The n-heptane layers were discarded and the combined aqueous layers were extracted with 90:10 dichloromethane:methanol (555 mL, 50 Vol). After stirring for 5 minutes, saturated sodium chloride (aq, 5.6 mL, 0.5 Vol) was added, stirring was continued for an additional 5 min and the layers allowed to settle for 10-30 minutes. The organic layer was removed and concentrated under reduced pressure to near dryness. Dichloromethane (40 mL, 3.6 Vol) was added and the solution passed through a 1 μm in-line filter. THF (500 mL, 45 Vol) was added followed by seed crystals (100 mg). The batch was agitated at room temperature for 1-20 hours then the resulting solids were collected on a Buchner funnel and the cake washed with THF/DCM (90:10, 110 mL, 10 Vol) followed by MTBE (110 mL, 10 Vol). The cake was conditioned under nitrogen for 2 hours then dried under vacuum at room temperature for 24 hours or until constant weight was obtained. The title compound was isolated as a white solid (8.70 g, 38.2%). $^1$H NMR (500 MHz, CDCl$_3$, δ ppm): 12.01 (s, 0.5 H), 10.32 (s, 0.5 H), 7.37-7.29 (m, 4H), 7.25-7.22 (m, 1H), 6.72-6.60 (m, 2H), 5.97-5.84 (m, 3H), 5.38 (s, 0.5H), 4.96 (s, 0.5H), 4.57 (s, 2H), 4.57 (s, 2H), 4.04-3.91 (m, 1H), 3.80-3.72 (br s, 3H), 3.65-3.42 (m, 2H), 3.27-3.16 (m, 0.5 H), 3.13-3.02 (m, 0.5H), 3.00-2.89 (m, 1H), 2.77-2.45 (m, 3H), 2.45-2.28 (m, 3H), 2.28-1.75 (m, 3H), 1.48 (s, 6H).

Step Two. (R)-1-((11bS,12S,14aR)-13-methoxy-2,3, 5,6,11b,12-hexahydro-1H-[1,3]dioxolo[4',5':4,5] benzo[1,2-d]cyclopenta[b]pyrrolo[1,2-a]azepin-12-yl) 4-methyl 2-(4-(benzyloxy)-4-methylpent-2-yn-1-yl)-2-hydroxysuccinate hydrochloride (14)

Under an inert nitrogen atmosphere, (R)-7-(benzyloxy)-3-hydroxy-3-((((11bS,12S,14aR)-13-methoxy-2,3,5,6,11b, 12-hexahydro-1H-[1,3]dioxolo[4',5':4,5]benzo[1,2-d]cyclopenta[b]pyrrolo[1,2-a]azepin-12-yl)oxy)carbonyl)-7-methyloct-5-ynoic acid hydrochloride (20, 6.75 g, 10.9 mmol) was dissolved in a mixture of dichloromethane (68 mL, 10 Vol) and dimethylformamide (135 uL, 0.02 Vol). The resulting solution was cooled to 0-5° C. and oxalyl chloride (1.05 mL) was added over 10 minutes maintaining an internal batch temperature <15° C. The reaction mixture was allowed to stir at 0-5° C. for an additional 1-3 hours until HPLC analysis (aliquot quench into methanol) confirmed complete formation of the acyl chloride. The reaction mixture was transferred via cannula to a separate reactor charged with methanol (270 mL, 40 Vol, precooled to 5-15° C.) maintaining an internal batch temperature <30° C. The reaction mixture was allowed to stir at 15-25° C. for an additional 1-24 hours until HPLC (aliquot quench into acetonitrile) showed formation of title compound. The reaction mixture was concentrated under reduced pressure to near dryness, redissolved in ethyl acetate (270 mL, 40 Vol) and concentrated under reduced pressure to near dryness. The residue was redissolved with ethyl acetate (270 mL, 40 Vol), passed through a 1 am in-line filter and concentrated to a final ethyl acetate volume of 3-5 Vol. Solids gradually formed within 15 minutes, the resulting slurry was maintained at room temperature for 1-3 hours, after which time the slurry was further cooled to 0-5° C. for an additional 1 hour. The solids were collected on a Buchner funnel and the cake was washed with ethyl acetate (27 mL, 4 Vol) followed by methyl tert-butylether (27 mL, 4 Vol). The cake was conditioned under nitrogen for 30 min then dried under vacuum at room temperature for 10-24 hours or until constant weight was obtained. The title compound was isolated as a white solid (6.57 g, 90%). $^1$H NMR (500 MHz, CDCl$_3$, δ ppm): 12.45 (s, 0.5 H), 11.21 (s, 0.5 H), 7.38-7.29 (m, 4H), 7.26-7.23 (m, 1H), 6.67-6.61 (m, 2H), 5.99-5.95 (m, 2H), 5.94-5.90 (m, 1H), 5.43 (s, 0.5H), 4.96 (s, 0.5H), 4.57 (s, 2H), 4.11-4.05 (m, 0.5 H), 4.01 (d, J=9.6 Hz, 0.5H), 3.78 (s, 2H), 3.76 (s, 2H), 3.75-3.61 (m, 1H), 3.60 (s, 3H), 3.54-3.50 (m, 1H), 3.48-3.39 (m, 0.5 H), 3.31-3.21 (m, 0.5H), 3.13-2.99 (m, 0.5H), 2.94-2.88 (m, 0.5H), 2.81-2.50 (m, 2.5H), 2.48-2.35 (m, 1H), 2.34-2.16 (m, 3.5H), 2.15-2.07 (m, 1H), 2.06-1.96 (m, 0.5H), 1.94-1.85 (0.5H), 1.83-1.75 (m, 0.5H), 1.49 (s, 6H). m/z: [M+H]$^+$=632.2.

Step Three. (R)-1-((11bS,12S,14aR)-13-methoxy-2, 3,5,6,11b,12-hexahydro-1H-[1,3]dioxolo[4',5':4,5] benzo[1,2-d]cyclopenta[b]pyrrolo[1,2-a]azepin-12-yl) 4-methyl 2-hydroxy-2-(4-hydroxy-4-methylpentyl)succinate (15)

(R)-1-((11bS,12S,14aR)-13-methoxy-2,3,5,6,11b,12-hexahydro-1H-[1,3]dioxolo[4',5':4,5]benzo[1,2-d]cyclopenta[b]pyrrolo[1,2-a]azepin-12-yl) 4-methyl 2-(4-(benzyloxy)-4-methylpent-2-yn-1-yl)-2-hydroxysuccinate hydrochloride (14, 0.300 g, 0.45 mmol) was dissolved in MeOH (3.0 mL, 10 Vol) and palladium hydroxide (29 mg, 0.1 equiv, 50 wt %) was added followed by triethylamine (0.22 mL, 3.5 equiv) and the vessel was evacuated then sparged with hydrogen gas (1-2 psig) and heated to 29-31° C. After 3-4 hours mass spectral analysis indicated nearly complete conversion to the fully saturated intermediate at which time acetic acid (4.2 mL, 14 Vol) was then added maintaining both temperature and hydrogen atmosphere for an additional 1-2 hours. The mixture was filtered through a pad of diatomaceous earth to remove the catalyst and concentrated under reduced pressure to give crude 15 which was taken up in toluene (4.5 mL), concentrated to near dryness two times, dissolved in toluene (6.0 mL), and washed with 1.25 N ammonium hydroxide solution (6 mL). The aqueous layer was extracted with an additional portion of toluene (6 mL) and the combined organic layers were passed through a pad of diatomaceous earth and concentrated under reduced pressure to near dryness. The residue was dissolved in toluene (15 mL), concentrated to near dryness, dissolved in toluene (5 mL), concentrated to near dryness and finally crystallized from toluene (2 mL) to provide crude 15 as a white solid. Purification by column chromatography (silica gel, DCM to 20% MeOH in DCM) provided 15 (0.251 g, 76%) as a foam. Alternatively, purification by reverse phase chromatography was achieved using a Biotage KP-C18-HS column eluting with a mixture of a pH 3 buffer (triethylamine/phosphoric acid) and THF. The fractions containing the product were combined, basified with dilute ammonium hydroxide and extracted with methylene chloride to provide the product after removal of the solvent at reduced pressure. Final crystallization from toluene or isopropylacetate provided 15 (0.210 g, 57%) as a white solid. $^1$H NMR (500 MHz, CDCl$_3$, δ ppm): 6.62 (s, 1H), 6.54 (s, 1H), 6.00 (m, 1H), 5.86 (m, 2H), 5.05 (s, 1H), 3.77 (d, J=9.5 Hz, 1H), 3.68 (s, 3H), 3.57 (s, 3H), 3.51 (s, 1H), 3.10 (m, 2H), 2.94 (m, 1H), 2.59 (m, 2H), 2.38 (m, 1H), 2.26 (d, J=16 Hz, 1H), 2.03 (m, 1H), 1.91 (d, J=16 Hz, 1H), 1.90 (m, 1H), 1.75 (m, 2H), 1.47-1.35 (m, 5H), 1.29-1.20 (m, 2H), 1.19 (s, 3H), 1.18 (s, 3H). m/z: [M+H]$^+$=546.2.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A process for preparation of a product compound of formula XIV:

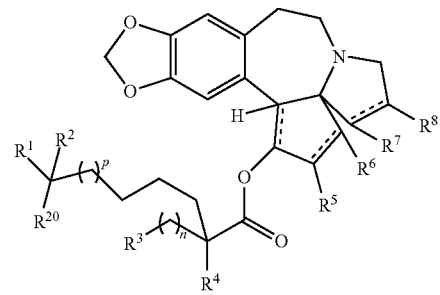

(XIV)

wherein
  $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with substituents as defined below in $R^{11}$; or $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or $R^1$ and $R^2$ are taken together with the atom to which they are attached to form a carbonyl, thiocarbonyl, sulfoxide, or sulfone;

$R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

$R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, or heteroaryl, wherein each of $C_1$-$C_6$ alkyl, $C_2$-$C_6$ alkenyl, alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;

$R^5$ is hydrogen, —$OR^{10}$, or =O;

$R^6$ is hydrogen, —$OR^{10}$, —$OCO_2R^{10}$, —$OCOR^{10}$, or —$OCON(R^{10})_2$;

$R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or $R^7$ and $R^8$ are taken together to form an optionally substituted 5- to 7-membered ring having 0-2 heteroatoms independently selected from nitrogen, oxygen, and sulfur;

$R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;

$R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;

$R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or $R^{12}$ and $R^{13}$ are taken together with the nitrogen to which they are attached to form a piperidine, pyrrolidine, piperazine, N-methylpiperazine, morpholine, or thiomorpholine ring;

$R^{14}$ is $C_1$-$C_4$ alkyl, $C_1$-$C_4$ haloalkyl, or phenyl;

$R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;

X is a protecting group;

each ~~~~~~ independently designates a single or double bond; and n is an integer from 0 to 9;

m is an integer from 0 to 2;

p is an integer from 0 to 3, or a pharmaceutically acceptable salt thereof, said process comprising:

providing intermediate compound XVa having the structure:

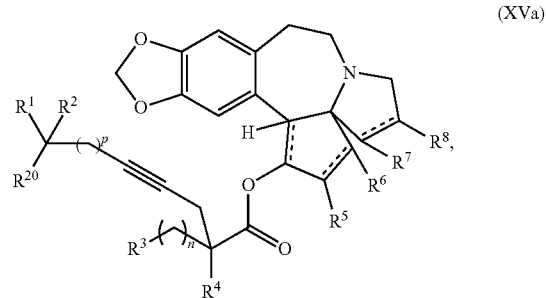

(XVa)

and reacting intermediate compound XVa with a reducing agent under conditions effective to produce the product compound of formula XIV, wherein the heterocycle is a stable monocyclic or multi-cyclic 3 to 18 membered ring which consists of carbon atoms and one to five heteroatoms selected from the group of nitrogen, oxygen, and sulfur and the heteroaryl is an aromatic monocyclic or multi-cyclic ring system of about 5 to about 19 ring atoms in which one or more atoms in the ring system are elements other than carbon.

2. The process according to claim 1, wherein the compound of formula XIV has the following structure:

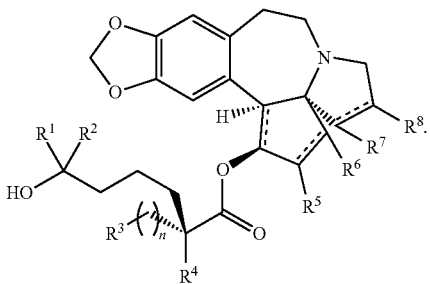

3. The process according to claim 2, wherein the compound of formula XIV has the following structure:

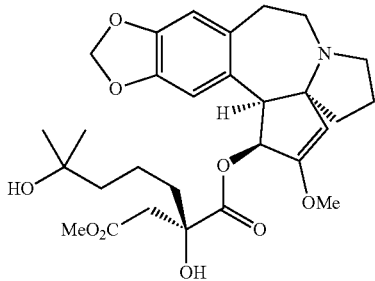

4. The process according to claim 1, wherein X is an arylmethyl or heteroarylmethyl protecting group, optionally substituted from 1 to 3 times with $C_1$-$C_6$ alkyl.

5. The process according to claim 1, wherein X is selected from the group consisting of alkanoyl, aryloyl, benzyloxycarbonyl, allyloxycarbonyl, (β-trimethylsilyilethoxy)carbonyl, (dialkylamino)carbonyl, triphenylmethyl, benzyl, 1-ethoxyethyl, methoxymethyl, 4-methoxyphenylmethyl, methoxyethoxymethyl, benzyloxymethyl, (β-trimethylsilylethoxy)methyl, tetrahydropyranyl, 2,2,2-trichloroethoxycarbonyl, t-butyl(diphenyl)silyl, trialkylsilyl, trichloromethoxycarbonyl, 2,2,2-trichloroethoxymethyl, alkansulfonyl, arylsulfonyl, and aryloxysulfonyl.

6. The process according to claim 1, wherein $R^{20}$ is —OX and said reacting intermediate compound XVa with a reducing agent is followed by removal of any protecting group.

7. The process according to claim 1, wherein intermediate compound XVa is provided as a substantially pure diastereomer having the structure:

(XV-A)

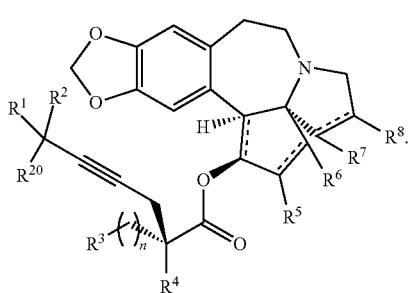

8. The process according to claim 1 further comprising: providing intermediate compound XXa having the structure:

(XXa)

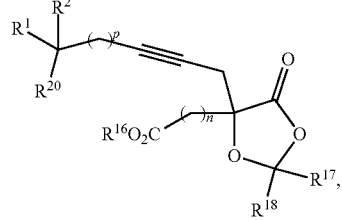

wherein $R^{16}$ is hydrogen;

$R^{17}$ is t-Bu, phenyl, naphthyl, $CF_3$, $CCl_3$, $CBr_3$, or $C_1$-$C_6$ alkoxy;

$R^{18}$ is H, Me, $CF_3$, $CCl_3$, $CBr_3$, or $C_1$-$C_6$ alkoxy; or $R^{17}$ and $R^{18}$ combine with the carbon to which they are attached to form an internally bridged cycloalkyl, wherein the internally bridged cycloalkyl can be optionally substituted front 1 to 6 times with a substituent independently selected in each occurrence from $C_{1-6}$ alkyl and $C_{1-6}$ alkyl further substituted with —$SO_2N(C_{1-6}$ alkyl$)_2$; or $R^{17}$ and $R^{18}$ are taken together with the atom to which they are attached to form a carbonyl, thiocarbonyl, sulfoxide, or sulfone, and reacting intermediate compound XXa with cephalotaxine followed by reaction with an alcohol in the presence of an activating agent to form intermediate compound XVa.

9. The process according to claim 1 further comprising:

providing intermediate compound XVIa having the formula:

(XVIa)

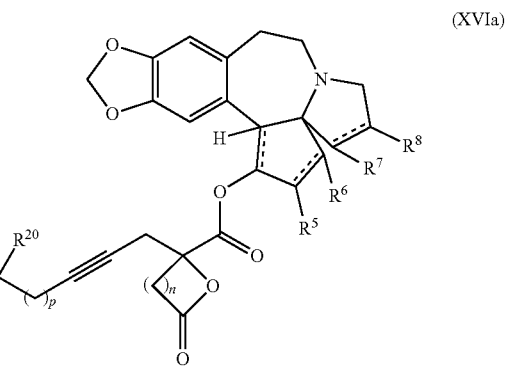

and reacting intermediate compound XVIa with a base to form intermediate compound XVa.

10. The process according to claim 1, further comprising purifying compound XIVa by crystallization and chromatography.

11. The process according to claim 10, further comprising isolating compound XIVa at a purity of at least 99%.

12. A compound of formula XV:

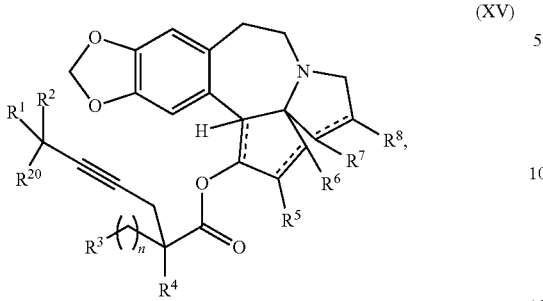

wherein
- $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or
- $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or
- $R^1$ and $R^2$ are taken together with the atom to which they are attached to form a carbonyl, thiocarbonyl, sulfoxide, or sulfone;
- $R^3$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;
- $R^4$ is hydrogen, —$N(R^{10})_2$, —$OR^{10}$, —$SR^{10}$, acyl, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}_2)(R^9)_2$, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or
- $R^3$ and $R^4$ are taken together to form a 5- to 7-membered ring having 0-2 heteroatoms independently selected from the group consisting of nitrogen, oxygen, and sulfur, optionally substituted from 1 to 3 times with $R^{11}$;
- $R^5$ is hydrogen, —$OR^{10}$, or =O;
- $R^6$ is hydrogen, —$OR^{10}$, —$OCO_2R^{10}$, —$OCOR^{10}$, —$OCOSR^{10}$, or —$OCON(R^{10})_2$;
- $R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or
- $R^7$ and $R^8$ are taken together to form an optionally substituted 5- to 7-membered ring having 0-2 heteroatoms independently selected from nitrogen, oxygen, and sulfur;
- $R^9$ is hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;
- each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;
- $R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;
- $R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or
- $R^{12}$ and $R^{13}$ are taken together with the nitrogen to which they are attached to form a piperidine, pyrrolidine, piperazine, N-methylpiperazine, morpholine, or thiomorpholine ring;
- $R^{14}$ is $C_1$-$C_4$ alkyl, $C_1$-$C_4$ haloalkyl, or phenyl;
- $R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;
- X is a protecting group;
- each ~~~~~~ independently designates a single or double bond;
- n is an integer from 0 to 9; and
- m is an integer from 0 to 2, or a pharmaceutically acceptable salt thereof, wherein the heterocycle is a stable monocyclic or multi-cyclic 3 to 18 membered ring which consists of carbon atoms and one to five heteroatoms selected from the group of nitrogen, oxygen, and sulfur and the heteroaryl is an aromatic monocyclic or multi-cyclic ring system of about 5 to about 19 ring atoms in which one or more atoms in the ring system are elements other than carbon.

13. A compound of formula XVI:

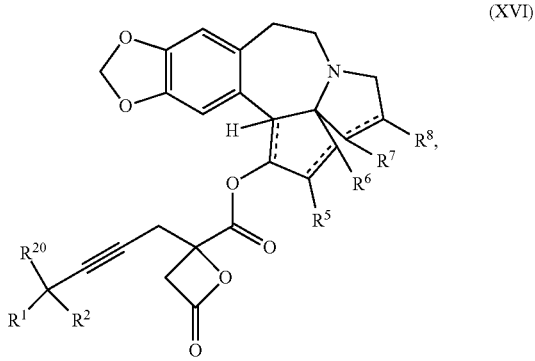

(XVI)

wherein
- $R^1$ and $R^2$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$; or
- $R^1$ and $R^2$ are taken together to form a 5- to 7-membered ring having 0-2 heteroatoms independently selected from the group consisting of nitrogen, oxygen, and sulfur, optionally substituted from 1 to 3 times with $R^{11}$; or
- $R^1$ and $R^2$ are taken together with the atom, to which they are attached to form a carbonyl, thiocarbonyl, sulfoxide, or sulfone;
- $R^5$ is hydrogen, —$OR^{10}$, or =O;
- $R^6$ is hydrogen, —$OR^{10}$, —$OCO_2R^{10}$, —$OCOR^{10}$, —$OCOSR^{10}$, or —$OCON(R^{10})_2$;
- $R^7$ and $R^8$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, heteroaryl, —$SO_2R^{10}$, and —$CO_2R^{10}$; or
- $R^7$ and $R^8$ are taken together to form an optionally substituted 5- to 7-membered ring having 0-2 heteroatoms independently selected from nitrogen, oxygen, and sulfur;
- each $R^{10}$ is independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl $C_4$-$C_7$ cycloalkylalkyl, heterocycle, aryl, and heteroaryl is optionally substituted from 1 to 3 times with $R^{11}$; or two $R^{10}$ on the same nitrogen are taken with the nitrogen to which they are attached to form a 4- to 7-membered heterocyclic ring having 1-2 heteroatoms independently selected from nitrogen, oxygen, and sulfur, optionally substituted from 1 to 3 times with $R^{11}$;
- $R^{11}$ is independently selected at each occurrence from a substituent in the group consisting of halogen, —$NO_2$, —$OR^{12}$, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_6$ cycloalkyl, and $C_4$-$C_7$ cycloalkylalkyl, wherein each of $C_1$-$C_6$ alkyl $C_2$-$C_6$ alkenyl, $C_2$-$C_6$ alkynyl, $C_3$-$C_6$ cycloalkyl, and $C_4$-$C_7$ cycloalkylalkyl is optionally substituted with 1 to 3 substituents independently selected at each occurrence from the group consisting of $C_1$-$C_4$ alkyl, $C_1$-$C_4$ alkoxy, halogen, Ar, —CN, and —$NR^{12}R^{13}$;
- $R^{12}$ and $R^{13}$ are each independently hydrogen, $C_1$-$C_4$ alkyl, $C_1$-$C_4$ haloalkyl, $C_1$-$C_4$ alkoxyalkyl, $C_3$-$C_6$ cycloalkyl, —$C(O)R^{14}$, phenyl, or benzyl, wherein phenyl or benzyl is optionally substituted with 1 to 3 substituents independently selected at each occurrence from the group consisting of halogen, —CN, $C_1$-$C_4$ alkyl, $C_1$-$C_4$ haloalkyl, and $C_1$-$C_4$ alkoxy; or
- $R^{12}$ and $R^{13}$ are taken together with the nitrogen to which they are attached to form a piperidine, pyrrolidine, piperazine, N-methylpiperazine, morpholine, or thiomorpholine ring;
- $R^{14}$ is $C_1$-$C_4$ alkyl, $C_1$-$C_4$ haloalkyl, or phenyl;
- $R^{20}$ is hydrogen, halogen, —$NO_2$, —$OR^{12}$, —OX, —$NR^{12}R^{13}$, —$NR^{12}C(O)_2R^{13}$, —$NR^{12}C(O)NR^{12}R^{13}$, —$S(O)_mR^{13}$, —CN, —$C(O)R^{13}$, —$C(O)NR^{12}R^{13}$, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, or heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$;
- X is a protecting group;
- m is an integer from 0 to 2; and
- each ≈≈≈≈ independently designates a single or double bond, or a pharmaceutically acceptable salt thereof, wherein the heterocycle is a stable monocyclic or multi-cyclic 3 to 18 membered ring which consists of carbon atoms and one to five heteroatoms selected from the group of nitrogen, oxygen, and sulfur and the heteroaryl is an aromatic monocyclic or multi-cyclic ring system of about 5 to about 19 ring atoms in which one or more atoms in the ring system are elements other than carbon.

14. The process according to claim 8 further comprising:
providing intermediate compound XXIIIa having the formula:

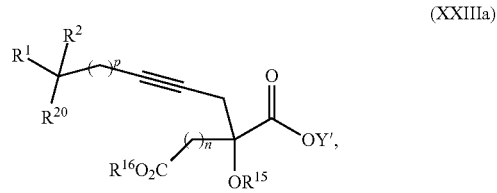

(XXIIIa)

wherein Y' is hydrogen or a protecting group; and
- $R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$,) —$C(NR^{10}_2)(R^9$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$, and
reacting intermediate compound XXIIIa with an activating agent under conditions effective to produce intermediate compound XXa, wherein the activating agent is selected from the group consisting of trichloromethyl chloroformate, bis(trichloromethyl) carbonate, phosgene, sulfuryl chloride, thionyl chloride, carbonyl diimidazole, thiocarbonvl diimiclazole, sulfuryl diimidazole, thiourea, and 1-propanephosphonic anhydride.

15. The process according to claim 9 further comprising:
providing intermediate compound XVIIa having the formula:

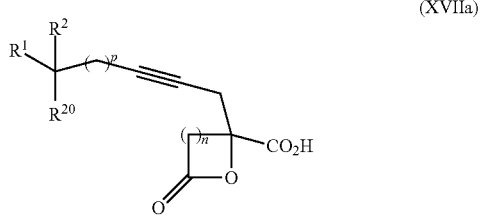

(XVIIa)

and
reacting intermediate compound XVIIa with cephalotaxine or a derivative thereof under conditions effective to produce
intermediate compound XVIa.

16. The process according to claim 15 further comprising:
providing intermediate compound XVIIIa having the formula:

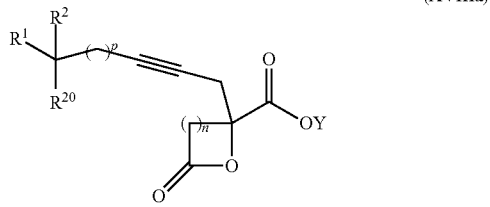

(XVIIIa)

wherein Y is a protecting group, and
reacting intermediate compound XVIIIa with a protecting group removing agent under conditions effective to produce intermediate compound XVIIa.

17. The process according to claim 16 further comprising:
providing intermediate compound XIXa having the formula:

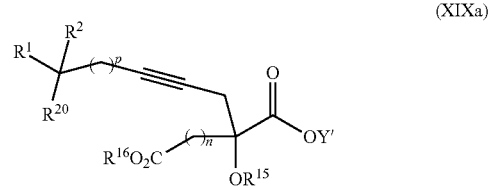

(XIXa)

wherein
Y' is hydrogen or a protecting group; and
$R^{15}$ and $R^{16}$ are each independently selected from the group consisting of hydrogen, $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, —$CO_2R^9$, —$CON(R^9)_2$, —$COSR^9$, —$COR^9$, —$C(OH)(R^9)_2$, —$C(OR^{10})(R^9)_2$, —$C(NR^{10}{}_2)(R^9)_2$, heterocycle, aryl, and heteroaryl, wherein each of $C_1$-$C_6$ alkyl, $C_2$-$C_6$ alkenyl, $C_2$-$C_6$ alkynyl, $C_3$-$C_7$ cycloalkyl, $C_4$-$C_7$ cycloalkylalkyl, heterocycle, aryl, and heteroaryl is optionally substituted from 1 to 3 times with $R^{11}$, and reacting intermediate compound XIXa with a reagent that activates the intermediate compound XIXa for substitution under conditions effective to produce intermediate compound XVIIIa, wherein the reagent that activates the intermediate for substitution is selected from the group consisting of BOP—Cl, CDI, alkyl chloroforrnates, thionyl chloride, $T_3P$, aroyl chlorides, and disubstitutedphosphoryl halides.

18. The process according to claim 17 further comprising:
providing intermediate compound XXa having the formula:

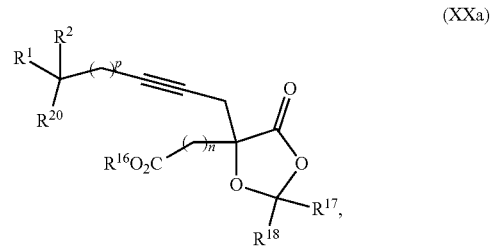

(XXa)

wherein
$R^{17}$ is t-Bu, phenyl, naphthyl, $CF_3$, $CCl_3$, $CBr_3$, or $C_1$-$C_6$ alkoxy;
$R^{18}$ is H, Me, $CF_3$, $CCl_3$, $CBr_3$, or $C_1$-$C_6$ alkoxy;
or $R^{17}$ and $R^{18}$ combine with the carbon to which they are attached to form an internally bridged cycloalkyl, wherein the internally bridged cycloalkyl can be optionally substituted from 1 to 6 times with a substituent independently selected in each occurrence from $C_{1-6}$ alkyl and $C_{1-6}$ alkyl further substituted with —$SO_2N(C_{1-6}$ alkyl$)_2$; or
$R^{17}$ and $R^{18}$ are taken together with the atom to which they are attached to form a carbonyl, thiocarbonyl, sulfoxide, or sulfone, and
reacting intermediate compound XXa with a protecting group introducing agent under conditions effective to produce
intermediate compound XIXa.

19. The process according to claim 18 further comprising:
providing intermediate compound VIIIa having the formula:

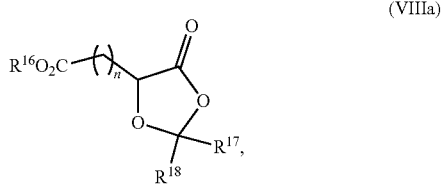

(VIIIa)

and
reacting intermediate compound VIIIa with a base and then with a compound of formula XXIa:

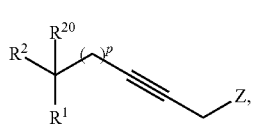
(XXIa)

wherein Z is selected from the group consisting of halogen, —OSO$_2$R$^{19}$, —OSO$_3$R$^{19}$, —OCOR$^{19}$, —OCO$_2$R$^{19}$, —OCSR$^{19}$, —OCS$_2$R$^{19}$, —OCN(R$^{19}$)$_2$, —OPO(R$^{19}$)$_2$, —OPO(OR$^{19}$)$_2$, —N(R$^{19}$)$_3$$^+$ and R$^{19}$ is selected from the group consisting of hydrogen C$_1$-C$_6$ alkyl C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, heterocycle, aryl, and heteroaryl is optionally substituted from 1 to 3 times with R$^{11}$, under conditions effective to produce the intermediate compound XXa.

20. The process according to claim 1 further comprising:
providing intermediate compound XXa having the structure:

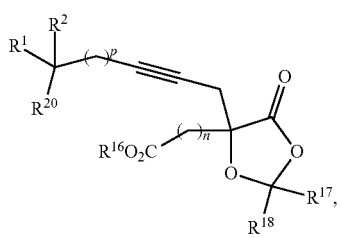
(XXa)

wherein
R$^{16}$ is selected from the group consisting of hydrogen, C$_1$-C$_6$ alkyl, C$_2$-C$_6$ alkenyl, C$_2$-C$_6$ alkynyl, C$_3$-C$_7$ cycloalkyl, C$_4$-C$_7$ cycloalkylalkyl, —CO$_2$R$^9$, —CON(R$^9$)$_2$, —COSR$^9$, —COR$^9$, —C(OH)(R$^9$)$_2$, —C(OR$^{10}$)(R$^9$)$_2$, —C(NR$^{10}$$_2$)(R$^9$)$_2$, heterocycle, aryl, and heteroaryl, wherein each of C$_1$-C$_6$ alkyl, C$_2$-C$_6$ alkenyl, C$_2$-C$_6$ alkynyl, C$_3$-C$_7$ cycloalldyl C$_4$-C$_7$ cycloalkylalkyl, heterocycle, aryl, and heteroaryl is optionally substituted from 1 to 3 times with R$^{11}$;
R$^{17}$ is t-Bu, phenyl, naphthyl, CF$_3$, CCl$_3$, CBr$_3$, or C$_1$-C$_6$ alkoxy;
R$^{18}$ is H, Me, CF$_3$, CCl$_3$, CBr$_3$, or C$_1$-C$_6$ alkoxy; or
R$^{17}$ and R$^{18}$ combine with the carbon to which they are attached to form an internally bridged cycloalkyl, wherein the internally bridged cycloalkyl can be optionally substituted from 1 to 6 times with a substituent independently selected in each occurrence from C$_{1-6}$ alkyl and C$_{1-6}$ alkyl further substituted with —SO$_2$N(C$_{1-6}$ alkyl)$_2$; or
R$^{17}$ and R$^{18}$ are taken together with the atom to which they are attached to form a carbonyl, thiocarbonyl, sulfoxide, or sulfone, and
reacting compound XXa with cephalotaxine or a derivative thereof in the presence of a base to form intermediate compound XVa.

21. The process according to claim 1 further comprising:
providing intermediate compound XVIa having the formula:

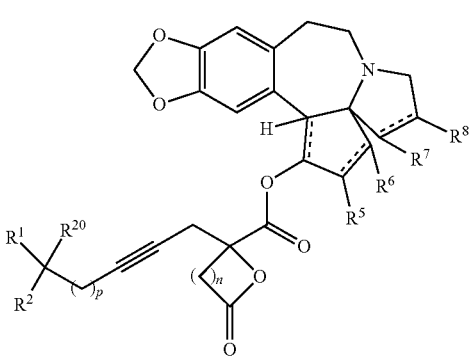
(XVIa)

and
reacting intermediate compound XVIa under Lewis acid catalysis conditions effective to produce compound XVa.

22. The process according to claim 1, wherein
R$^1$ and R$^2$ are each independently selected from C$_1$-C$_6$ alkyl, wherein each of C$_1$-C$_6$ alkyl is optionally substituted from 1 to 3 times with substituents as defined below in R$^{11}$; or
R$^3$ is —CO$_2$R$^9$ or —COSR$^9$;
R$^4$ is —OR$^{10}$;
R$^5$ is —OR$^{10}$;
R$^6$ is hydrogen;
R$^7$ is hydrogen;
R$^8$ is hydrogen;
R$^9$ is hydrogen, C$_1$-C$_6$ alkyl, C$_2$-C$_6$ alkenyl, C$_2$-C$_6$ alkenyl, C$_4$-C$_7$ cycloalkylalkyl, or aryl, wherein each of C$_1$-C$_6$ alkyl and C$_2$-C$_6$ alkenyl is optionally substituted from 1 to 3 times with R$^{11}$;
each R$^{10}$ is independently selected from the group consisting of hydrogen, C$_1$-C$_6$ alkyl, and C$_4$-C$_7$ cycloalkylalkyl;
R$^{11}$ is independently selected at each occurrence from a substituent in the group consisting of halogen, —OR$^{12}$, C$_1$-C$_6$ alkyl, and C$_2$-C$_6$ alkenyl;
R$^{12}$ and R$^{13}$ are each independently hydrogen, C$_1$-C$_4$ alkyl, —C(O)R$^{14}$, or benzyl;
R$^{14}$ is C$_1$-C$_4$ alkyl or phenyl;
R$^{20}$ is hydrogen, halogen, or —OR$^{12}$;
each ══════ independently designates a single or double bond; and
n is 1;
p is 0 or 1,
or a pharmaceutically acceptable salt thereof,
said process comprising:
providing intermediate compound XVa having the structure:

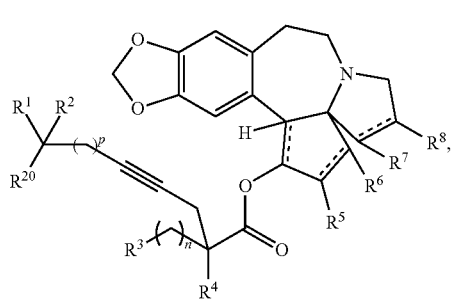
(XVa)

and
reacting intermediate compound XVa with a reducing agent under conditions effective to produce the product compound of formula XIV.

\* \* \* \* \*

UNITED STATES PATENT AND TRADEMARK OFFICE
CERTIFICATE OF CORRECTION

PATENT NO. : 10,597,401 B2
APPLICATION NO. : 15/572372
DATED : March 24, 2020
INVENTOR(S) : Herr et al.

It is certified that error appears in the above-identified patent and that said Letters Patent is hereby corrected as shown below:

In the Claims

In Claim 1, Column 153, Line 25, delete "alkynyl" and insert --$C_2$-$C_6$ alkynyl-- in its place.

In Claim 1, Column 153, Line 35, insert -- —OCOSR$^{10}$,-- after "—OCOR$^{10}$,".

In Claim 1, Column 153, Line 61, delete "haying" and insert --having-- in its place.

In Claim 5, Column 155, Lines 36-37, delete "(β-trimethylsilyilethoxy)carbonyl" and insert --(β-trimethylsilylethoxy)carbonyl-- in its place.

In Claim 8, Column 156, Line 24, delete "front" and insert --from-- in its place.

In Claim 12, Column 157, Line 22, delete "C $_1$-$C_6$ alkyl" and insert --$C_1$-$C_6$ alkyl-- in its place.

In Claim 13, Column 159, Line 33, delete "," after "atom".

In Claim 14, Column 160, Line 58, delete "—C(OR$^{10}$)(R$^9$)$_2$,)" and insert -- —C(OR$^{10}$)(R$^9$)$_2$,-- in its place.

In Claim 14, Column 160, Line 59, delete "—C(NR$^{10}$$_2$)(R$^9$" and insert -- —C(NR$^{10}$$_2$)(R$^9$)$_2$-- in its place.

In Claim 14, Column 161, Line 4, delete "thiocarbonvl diimiclazole" and insert --thiocarbonyl diimidazole-- in its place.

In Claim 17, Column 162, Lines 10-11, delete "chloroforrnates" and insert --chloroformates-- in its place.

Signed and Sealed this
Twenty-eighth Day of July, 2020

Andrei Iancu
*Director of the United States Patent and Trademark Office*

CERTIFICATE OF CORRECTION (continued)
U.S. Pat. No. 10,597,401 B2

In Claim 17, Column 162, Line 12, delete "disubstitutedphosphoryl" and insert --disubstituted phosphoryl-- in its place.

In Claim 20, Column 163, Line 44, delete "$C_3$-$C_7$ cycloalldyl" and insert --$C_3$-$C_7$ cycloalkyl-- in its place.

In Claim 22, Column 164, Lines 32-33, delete "$C_2$-$C_6$ alkenyl" and insert --$C_2$-$C_6$ alkynyl-- in its place.